(12) United States Patent
Huang

(10) Patent No.: US 8,067,454 B2
(45) Date of Patent: Nov. 29, 2011

(54) THIO-SUBSTITUTED ANTHRA [1, 2-D] IMIDAZOLE- 6, 11-DIONE DERIVATIVES, PREPARATION METHOD AND APPLICATION THEREOF

(75) Inventor: Hsu-Shan Huang, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 12/712,526

(22) Filed: Feb. 25, 2010

(65) Prior Publication Data
US 2011/0207727 A1    Aug. 25, 2011

(51) Int. Cl.
*C07D 235/02* (2006.01)
(52) U.S. Cl. ..................... 514/395; 548/300.4
(58) Field of Classification Search .............. 548/300.4
See application file for complete search history.

(56) References Cited

OTHER PUBLICATIONS

Golub et al., Molecular Classification of Cancer: Class Discovery and Class Prediction by Gene Expression Monitoring, Science, vol. 286, Oct. 15, 1999, p. 531-537.*

Targeted Cancer Therapies, http://www.cancer.gov/cancertopics/factsheet/therapy/targeted, accessed Jan. 12, 2011.*
Bel-Ghacham, Synthesis and complexing properties of new polyether heterocycles containing anthraquinonic sulfur system, 2008, Journal Marocain de Chimie Heterocyclique, vol. 7, No. 1, p. 62-69.*

* cited by examiner

*Primary Examiner* — Andrew D Kosar
*Assistant Examiner* — Karen Cheng
(74) *Attorney, Agent, or Firm* — Muncy, Geissler, Olds & Lowe, PLLC

(57) ABSTRACT

A series of novel thio-substituted anthra[1,2-d]imidazole-6, 11-dione derivatives, and the preparation method and application of said derivatives, said application having a pharmaceutical composition containing said derivatives with therapeutically effective amount for treating cancer, and said application involves effects of said derivatives for inhibiting telomerase activity, inhibiting the growth of cancer cell, treating cancer and the like.

23 Claims, 24 Drawing Sheets fl-5
 fl-9
 fl-12
 fl-18
 fl-19
 fl-21 f2-1 f2-2 f2-3 f2-6 f3-1 f1-17 f2-1 f2-6

THIO-SUBSTITUTED ANTHRA [1, 2-D] IMIDAZOLE- 6, 11-DIONE DERIVATIVES, PREPARATION METHOD AND APPLICATION THEREOF

BACKGROUND OF THE INVENTION

1. Field of the Invention

The present invention relates to development of cancer drug, in particular, the development of the telomerase inhibitor.

2. Description of the Prior Art

Telomere

A telomere is a region of repetitive DNA at the end of a chromosome, which protects the end of the chromosome from deterioration, recombination, and end-to-end fusion. A telomere is composed of short and repeated DNA sequences. A high percentage of guanine (G) is present in this DNA sequence from the 5'-end to the 3'-end. The telomere DNA sequence (TTAGGG)n is conserved among vertebrates, including humans.

In a normal somatic cell, the terminal end of the chromosome will lose a part of the RNA primer after each replication, and will shorten off about 50-60 bp after each cell division. When the telomere is shortened to a certain extent, a cell will go to apoptosis; this phenomenon is called an end-replication problem of a cell.

Telomerase

Telomerase is the enzyme that synthesizes telomeric DNA, the terminal DNA at chromosome ends which, together with telomere-binding proteins, confers stability to chromosomes. In most organisms, replication and maintenance of the length of telomere has to rely on telomerase. The telomerase is composed of RNA and protein subunits. At present, part of the important telomerase subunits has been identified. The composition of human telomerase comprises human telomerase reverse transcriptase (hTERT) having reverse transciptase activity, human telomerase RNA component used as a template, and some telomere-binding proteins such as human telomerase-associated protein, p23, hsp90, hsp40, hsp70 and the like.

Many research studies have indicated that the activity of human telomerase can only be detected in cells having a high proliferation ability such as, for example, germ cells, hemopoietic cells, part of stem cells, most of immortalized cells and most of tumor cells. In the somatic cell, the telomere will be shortened gradually as the number of cell divisions increase, which may be considered as the mitotic clock for counting the number of cell divisions. When a telomere is shortened to a certain extent, a cell will stop division and entering an aging stage, stay at this stage for a period of time, and then go to death. This period of time is called mortality stage 1 (M1 stage). When a tumor suppressor gene such as p53 or Rb is mutated within M1 stage, the cell might escape from the aging stage and continue cell division in a period of time which is called mortality stage 2 (M2 stage). If a cell lacks telomerase activity during this period, the length of a telomere will be reduced still and the telomere will not be able to protect the terminal end of the chromosome. This might result in instability of the chromosome, as well as the cell being unable to transfer genetic information completely and entering apoptosis in the end. Therefore, M2 stage is also called a crisis stage. Most of cells will die in the M2 stage, except a small portion of cells with telomerase activity will survive. This small portion of cells will continue to divide without limitation and become an immortalized cell (or a cancer cell).

In view of the foregoing, it is thought generally that the activation of telomerase can maintain the length of a telomere so as to prevent a cell from entering the aging stage; or that the inhibition of telomerase activity can be used to limit the division of a cancer cell. Both possibilities may become key factors in the development of a cell toward immortalization or cancerization. In summary, using the telomerase inhibitors to treat the cancer have been considered as a novel cancer-specific therapy, as most tumor cells have high expression of telomerase, whereas most normal somatic cells express low or undetectable levels of telomerase and is therefore an attractive target for the design of anticancer agents.

Anthraquinone-containing extracts from different plant sources such as senna, cascara, aloe, frangula, and rhubarb have been found to have wide variety of pharmacological activities such as anti-inflammatory, wound healing, analgesic, antipyretic, antimicrobial, and antitumor activities. Some of the anthraquinone derivatives have also shown antitumor activity. Therefore, many investigators consider them as highly promising lead candidates in drug design.

In view of the importance of the development of cancer therapy drugs, the invention provides inventive thio-substituted[1,2-d]anthra[1,2-d]imidazole-6,11-dione derivatives, preparation method and application thereof.

SUMMARY OF THE INVENTION

One object of the invention is to provide a series of novel thio-substituted[1,2-d]anthra[1,2-d]imidazole-6,11-dione derivatives, said thio-substituted[1,2-d]anthra[1,2-d]imidazole-6,11-dione derivatives represented by formula I, wherein $R_a$ is defined herein.

Another object of the invention is to provide a method for preparing novel thio-substituted[1,2-d]anthra[1,2-d]imidazole-6,11-dione derivatives represented by formula I, wherein $R_a$ is defined herein.

In addition, another object of the invention is to provide a pharmaceutical composition containing said novel thio-substituted[1,2-d]anthra[1,2-d]imidazole-6,11-dione derivatives as represented by formula I (wherein $R_a$ is defined herein), said pharmaceutical composition is used to treat cancer.

In order to achieve the above-described objects of the invention, the inventor used commercial 1,2-diaminoanthraquinone as the reaction starting materials (S) to carry out modification on various functional groups through chemical synthetic reaction, so as to produce a series of novel thio-substituted[1,2-d]anthra[1,2-d]imidazole-6,11-dione derivatives, namely, compounds f1-0 to f1-23, f2-1 to f2-9 and f3-1.

In addition, the invention evaluates the inhibition effect of thio-substituted[1,2-d]anthra[1,2-d]imidazole-6,11-dione derivatives on telomerase, so as to provide inhibition effect on the growth of tumor cell or cancer cell, and further treat cancer.

These features and advantages of the present invention will be fully understood and appreciated from the following detailed description of the accompanying drawings.

DETAILED DESCRIPTION OF THE PREFERRED EMBODIMENT

Figure 1:
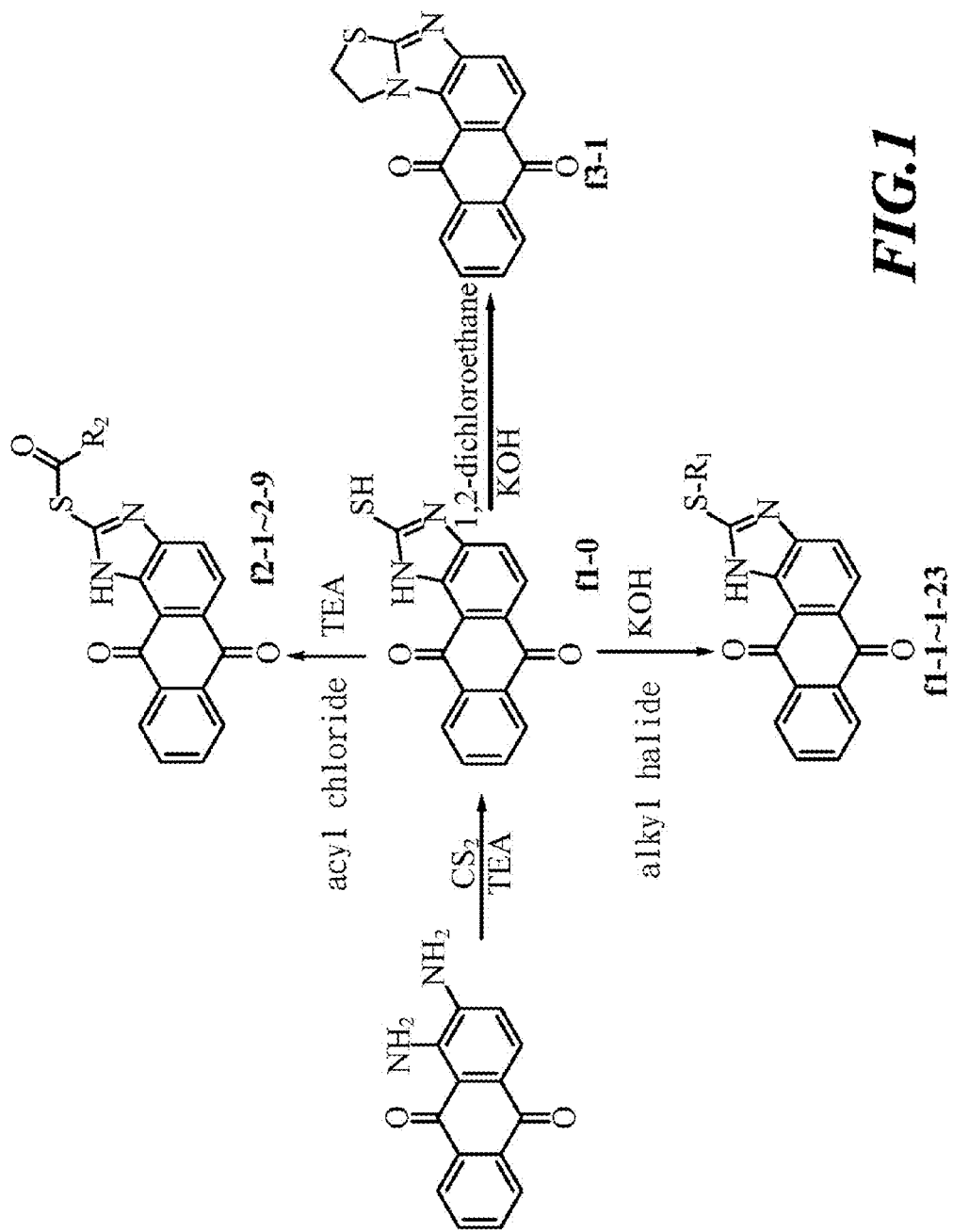
FIG. 1 depicts the preparation process of compound f1-0 to f1-23, f2-1 to f2-9 and f3-1.

The invention provides a series of novel thio-substituted[1,2-d]anthra[1,2-d]imidazole-6,11-dione derivatives as represented by formula I, wherein $R_a$ is as defined herein; and further provides a pharmaceutical composition, wherein said pharmaceutical composition comprises at least one treating effective amount compound as represented by general formula I and a pharmaceutically acceptable excipient, wherein $R_a$ is defined herein:

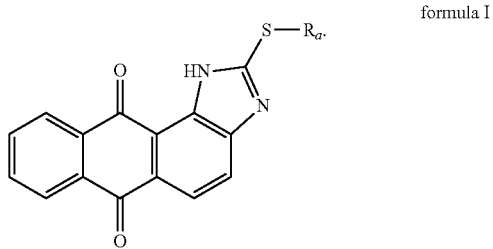

formula I

Said pharmaceutical composition with therapeutically effective amount is to be used for treating cancer, inhibiting the growth of tumor and cancer cells; and further, said pharmaceutical composition possesses inhibition activity of telomerase, which comprises of inhibiting telomerase activity, or a biological activity for stabilizing the structure of a telomere; wherein said cancer includes but not limited to leukemia, renal cancer and the like.

The excipient that can be used in the invention comprises, but is not limited to, diluent, filler, binder, disintegrating agent, lubricant and the like. Further, said excipient include, but not limited to microcrystalline cellulose, polyvinylpyrrolidone (PVP), corn starch, modified starches, sodium carboxymethylstarch, resin, gelatinized starches, sugars, polyethylene glycol (PEG), polyvinyl alcohol, hydroxypropyl cellulose, methyl cellulose, hydroxymethyl cellulose, hydroxypropyl methyl cellulose and the like.

The term "treating effective amount" or "pharmaceutically effective dosage" refers to the amount of a compound or a combination of compounds used to treat disease (such as cancer), to improve, attenuate or eliminate one or more symptoms of a particular disease (such as cancer), or to inhibit or delay the outbreak of one or more symptoms caused by growth or proliferation of cancer cells.

The term "pharmaceutically acceptable" is intended to mean that a substance or a combination has to be compatible with other components in the same formulation, and also has to be not harmful or cause no other side effect to a patient.

The invention will be illustrated with the examples as follows, without the intention that the invention is limited thereto. The substance or material herein are easily obtained, the source of material is not limited to following examples.

Example 1

Source of Material

From Merck:
 TLC 60 F254, absolute ethanol, methanol, 95% ethyl alcohol, dichloromethane, pyridine, DMSO-d6, N-N-dimethylformamide, DMF, chloroform-d, potassium bromide (KBr).

From Aldrich:
 Iodoethane, 1-chloropropane, 1-chlorobutane, 1-(chloromethyl)-2-methylbenzene, methyl 4-chlorobutanoate, (E)-methyl-4-chlorobut-2-enoate, 3-bromoprop-1-yne, 1,4-dichlorobutane, 1,5-dibromopentane, 1,6-dichlorohexane, 1-(2-chloroethyl)pyrrolidine, 1-(2-chloroethyl)piperidine, 4-(2-chloroethyl)morpholine, 1-(3-chloropropyl)piperidine, 3-chloro-N,N-dimethylpropan-1-amine, 3-bromoprop-1-ene, 2-nitrobenzoyl chloride, morpholine-4-carbonyl chloride, 4-methylpiperazine-1-carbonyl chloride, 3-phenylpropanoyl chloride, 2,5-dinitrobenzoyl chloride, 2,5-dimethylfuran-3-carbonyl chloride, pyrrolidine-1-carbonyl chloride, piperidine-1-carbonyl chloride, diethylcarbamic chloride, 1,2-dichloroethane.

From Acros:
 Morpholine, pyrrolidine, diethylamine, dipropylamine.

Example 2

Chemical Synthesis

Chemical synthetic procedures described hereinafter can be referred to FIG. 1 and the following description of the procedures:

2-1. Procedure for the synthesis of thioether-substituted anthra[1,2-d]imidazole-6,11-dione derivatives A. Cyclizing Procedure:
 Compound 1, 2-diaminoanthraquinone was dissolved in N,N-dimethylformamide, and thereto was added with carbon disulfide ($CS_2$), and then with triethylamine (TEA) under stirring. Then, the mixed solution was heated under reflux. After completion of reaction, the mixed solution was cooled down, filtered to collect the precipitate, and finally, the precipitate was rinsed with ethanol to obtain a red compound f1-0.

B. Alkylation Reaction

Compound f1-0 was dissolved in N,N-dimethylformamide, and thereto was added with alkyl halide (RX), and potassium hydroxide (KOH) under stirring. After completion of reaction, the mixed solution was cooled down, filtered to collect the precipitate, and finally, the precipitate was recrystallized in ethanol (EtOH) to obtain compounds f1-1 to f1-23 as represented by formula I, wherein $R_a$ is defined as $R_1$ in Table 1, respectively.

2-2. Synthetic procedure for thioester-substituted anthra[1,2-d]imidazole-6,11-dione derivatives Synthetic Procedure:
A. Cyclizing Procedure:

The cyclizing procedure is the same as described in Example 2 2-1. A. cyclizing procedure.

B. Thioester Reaction

Compound f1-0 was dissolved in N,N-dimethylformamide, and thereto was added with acyl chloride (ClCOR), and then with TEA under stirring. After completion of reaction, the mixed solution was cooled down, filtered to collect the precipitate, and finally, the precipitate was recrystallized in EtOH to obtain compounds f2-1 to f2-9 as represented by formula I, wherein $R_a$ is represented by formula II:

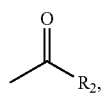

formula II formula II, wherein $R_2$ is defined in Table 1, respectively.

2-3. Synthetic procedure for thio-substituted anthra[1,2-d]imidazole-6,11-dione derivatives A. Cyclizing Procedure:

The cyclizing procedure is same as described in Example 2 2-1. A. cyclizing procedure.

B. Alkylation Reaction

Compound f1-0 was dissolved in N,N-dimethylformamide, and thereto was added with 1,2-dichloroethane, and then KOH under stirring. after completion of reaction, the mixed solution was cooled down, filtered to collect the precipitate, and finally, the precipitate was recrystallized in EtOH to obtain compound f3-1 as represented by formula III in Table 1.

Example 3

Telomerase Activity Assays 3-1. Screen of the Telomerase Inhibitor

Telomeric Repeat Amplification Protocol (TRAP) Assay:

Telomerase activity was detected by a modified version of the general TRAP protocol. Telomerase products were resolved by 10% polyacrylamide gel electrophoresis and visualized by staining with SYBER Green. As a source of telomerase, the total cell lysates derived from lung cancer cell line H1299 cells were used. Protein concentration of the lysates was assayed using Bio-Rad protein assay kit using BSA standards.

3-2. MTT Assay

MTT assay is a method often used to determine cell survival rate or proliferation, which is described briefly as followed:

Cell Line for Screening:

The tumor cell (cancer cell) GBM890, GBM18401 and human brain astroglia SVGP-P1 cell line are obtained from laboratory of Veterans General Hospital.

The above-described cells are cultured in a 96-well plate, to which was added with 25 µl MTT solution, and cultured in a 37° C. carbon dioxide incubator for 4 hours. Then, 100 µl Lysis buffer is added and incubated in a 37° C. carbon dioxide incubator overnight. An ELISA reader (Bio-Rad Model 450) is used to read optical density (O.D.) at 550 nm.

3-3. The National Cancer Institute (NCI)'s Anticancer Drug Screen

In brief, cellular protein levels were determined after 48 hours of drug exposure by sulforhodamine B colorimetry. Through the use of a time 0 cell control, the cell growth can be determined for each cell line thus allowing calculations of the 50% growth inhibitory concentration ($GI_{50}$), the total growth inhibition (TGI), and the 50% lethal concentration ($LC_{50}$). Comparison to plates not exposed to drug permits determination of concentration and times of exposure conferring 50% net growth inhibition ($GI_{50}$), TGI, and 50% cell kill ($LC_{50}$). These data are then plotted as mean bar graphs and as dose-response curves.

From the data analysis it follows that approximately 95% of the actives (potent anticancer drugs) from the 60 cell line screen can be identified. By these criteria, 6 compounds (each with its certification number, refer to Table 2) of the invention were reported that having anticancer activity.

Synthesis and Analysis of Each Compound:

The chemical synthetic procedure of thio-substituted[1,2-d]anthra[1,2-d]imidazole-6,11-dione derivatives described in Example 2 was disclosed further in following examples.

Testing Instruments:

Melting point determination was carried out on a Büchi 545 melting point tester. IR (Kbr) was recorded on a Perkin-Elmer 983G spectrometer. MS was determined in National Chiao Tung University Instrument Center. $^1$H-NMR and $^{13}$C-NMR were recoded on Varian GEMINI-300 (300 MHz).

Example 4

2-Mercapto-1(3)H-anthra[1,2-d]imidazole-6,11-dione (f1-0)

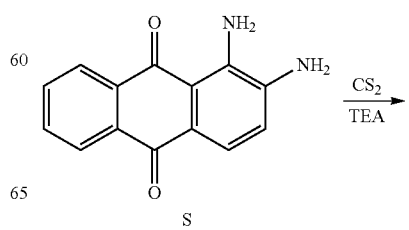

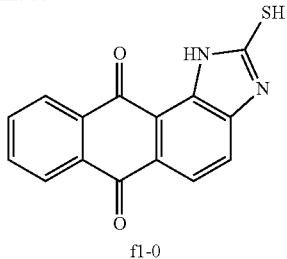

Compound (S) 1,2-diaminoanthraquinone (1.19 g, 5 mmole) was dissolved in 30 mL N,N-dimethylformamide, added thereto successively with carbon disulfide (0.4 g, 5 mmol) and triethylamine (3 mL) under stirring at room temperature. The well-mixed mixture was under reflux for 10 hours. After completion of reaction, the mixed solution was poured into ice-water (200 mL). Then, the mixture was filtered to collect the precipitate. Finally, the precipitate was recrystallized in ethanol to obtain an earth red compound f1-0.

Mol. Wt.: 280.0306 ($C_{15}H_8N_2O_2S$); Rf: 0.80 (ethyl acetate:dichloromethane=1:4); Yield: 80%; mp: 407~409° C. (EtOH); IR (KBr) cm$^{-1}$: 3221 (NH), 3192 (NH), 1665 (CO); EI MS m/z: 280 (82.25, M), 279 (32.53, M−1), 282 (4.03, M+1), 50 (100); $^1$H-NMR (300 MHz, DMSO-d6) δ (ppm): 7.51 (d, J=8.1 Hz, 1H, Ar—H5), 7.99 (d, J=8.4 Hz, 1H, Ar—H4), 7.91-7.88 (m, 2H, Ar—H7,10), 8.18-8.16 (m, 2H, Ar—H8,9), 12.73 (1H, s, —NH), 13.29 (1H, s, —NH); $^{13}$C-NMR (75 MHz, DMSO-d6) δ (ppm): 113.89 ($C_3$), 115.27 ($C_4$), 122.41 ($C_1$), 126.26 ($C_1$), 126.76, 126.88, 130.95 ($C_8$), 132.89 ($C_5$), 133.06 ($C_7$), 134.25 ($C_6$), 134.47 ($C_1N$), 138.19 ($C_2N$), 172.89 (CS), 181.79 ($C_9O$), 182.46 ($C_{10}O$).

Example 5

2-(Ethylthio)-1H-anthra[1,2-d]imidazole-6,11-dione (f1-1)

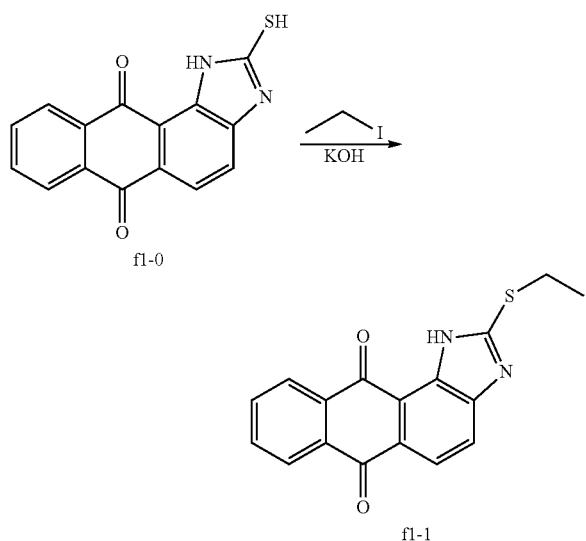

Compound f1-0 (1.4 g, 5 mmole) was dissolved in 30 mL N,N-dimethylformamide, added thereto successively with Iodoethane (1.17 g, 7.5 mmol) and $K_2CO_3$ (1.38 g, 10 mmol) under stirring at room temperature. The well-mixed mixture was under reflux for 12 hours. After completion of reaction, the mixture was filtered to collect the precipitate. The precipitate was separated by column chromatography with eluent (ethyl acetate:dichloromethane=1:6) to obtain a yellow brown compound f1-1.

Mol. Wt.: 308.35 ($C_{17}H_{12}N_2O_2S$); Rf: 0.6 (ethyl acetate: n-hexane=1:4); Yield: 65%; mp: 239° C. (EtOH); IR (KBr) cm$^{-1}$: 1680 (CO); EI-MS m/z: 307 (76.58, M−1), 309 (55.18, M+1), 279 (100), 275 (99.10); $^1$H-NMR (300 MHz, CDCl$_3$) δ (ppm): 1.53 (t, J=7.2, 7.8 Hz, 3H, —CH3), 3.44 (q, J=7.5, 7.2, 7.8 Hz, 2H, —CH$_2$—), 7.78~7.26 (m, 2H, Ar—H$_{6,7}$), 7.95 (d, J=8.4 Hz, 1H, Ar—H$_4$), 8.18 (d, J=8.4 Hz, 1H, Ar—H$_3$), 8.35~8.25 (m, 2H, Ar—H$_{5,8}$), 10.83 (br, 1H, —NH); $^{13}$C-NMR (300 MHz, CDCl3) δ (ppm): 13.55 (SCC), 34.44 (SC), 117.10 ($C_3$), 121.94 ($C_4$), 123.78, 126.78, 127.72, 127.77, 133.48 ($C_8$), 133.91 ($C_5$), 134.10 ($C_7$), 134.30 ($C_6$), 134.57 ($C_1N$), 149.64 ($C_2N$), 158.22 (CS), 182.90 ($C_{10}O$), 185.22 ($C_9O$).

Example 6

2-(propylthio)-1H-anthra[1,2-d]imidazole-6,11-dione (f1-2)

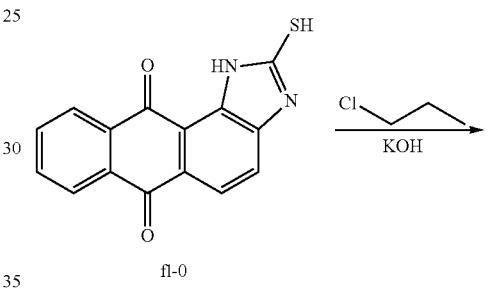

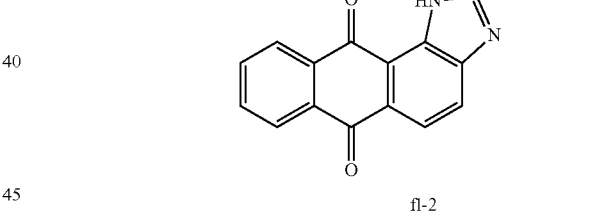

Compound f1-0 (1.4 g, 5 mmole) was dissolved in 30 mL N,N-dimethylformamide, added thereto successively with 1-chloropropane (0.59 g, 7.5 mmol) and KOH (1 equive, 10 mmol) under stirring for 13 hours at room temperature. After completion of reaction, the mixed solution was poured into ice-water (200 mL). Then, the mixture was filtered to collect the precipitate. The precipitate was rainsed with hot ethanol to obtain a brown compound f1-2.

Mol. Wt.: 322.07 ($C_{18}H_{14}N_2O_2S$); Rf: 0.6 (ethyl acetate: n-hexane=1:4); Yield: 55%; mp: 213.7° C. (EtOH); IR (KBr) cm$^{-1}$: 1780 (CO); ELMS m/z: 322 (13.88, M), 323 (2.36, M+1); $^1$H-NMR (300 MHz, CDCl$_3$) δ (ppm): 1.0 (t, J=7.2, 7.5 Hz, 3H, —CH3), 1.92-1.84 (m, 2H, —CH$_2$—), 3.41 (t, J=7.5, 6.9 Hz, 2H, —SCH2) (7.82-7.25 (m, 2H, Ar—H$_{6,7}$), 7.92 (d, J=8.4 Hz, 1H, Ar—H$_4$), 8.16 (d, J=8.4 Hz, 1H, Ar—H$_3$), 8.33-8.23 (m, 2H, Ar—H$_{5,8}$), 10.84 (br, 1H, —NH); $^{13}$C-NMR (300 MHz, CDCl$_3$) δ (ppm): 13.53 (SCCC), 23.05 (SCC), 34.44 (SC), 117.10 ($C_3$), 121.94 ($C_4$), 126.78, 127.72, 127.77, 133.48 ($C_8$), 133.91 ($C_5$), 134.10 ($C_7$), 134.30 ($C_6$), 134.57 ($C_2N$), 149.64 ($C_1N$), 158.22 (CS), 182.90 ($C_{10}O$), 185.22 ($C_9O$).

Example 7

2-(Butylthio)-1H-anthra[1,2-d]imidazole-6,11-dione (f1-3)

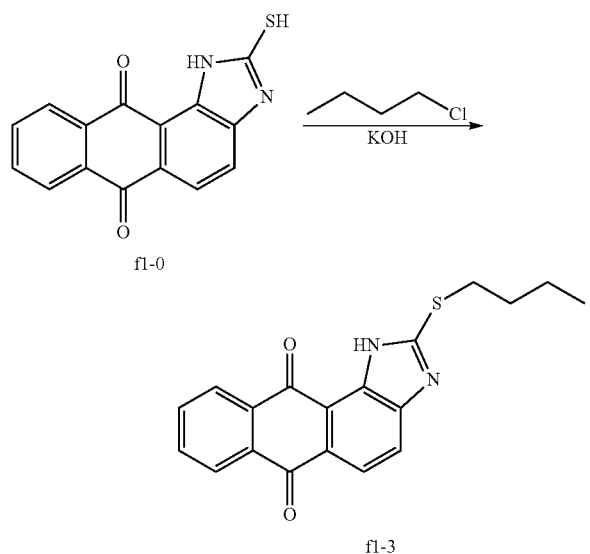

Compound f1-0 (1.4 g, 5 mmole) was dissolved in 30 mL N,N-dimethylformamide, added thereto successively with 1-chlorobutane (1.17 g, 7.5 mmol) and KOH (1 equive, 10 mmol) under stirring for 9 hours at room temperature. After completion of reaction, the mixed solution was poured into ice-water (200 mL). Then, the mixture was filtered to collect the precipitate. The precipitate was recrystallized in ethanol to obtain a brown compound f1-3.

Mol. Wt.: 336.41 (C19H16N2O2S); Rf: 0.6 (ethyl acetate: dichloromethane=1:6); Yield: 54%; mp: 227.6° C. (EtOH); IR (KBr) cm$^{-1}$: 1700 (CO); EI-MS m/z: 336 (17.23, M); $^1$H-NMR (300 MHz, CDCl3) δ (ppm): 0.96 (t, J=7.5 Hz, —CH3-), 1.57~1.49 (2H, m, —CH2-), 1.86~1.8 (m, 2H, —CH2-), 3.4 (t, J=7.2, 7.5, 2H, S—CH2-), 7.78-1.25 (m, 2H, Ar—H$_{6,7}$), 7.88 (d, J=8.4 Hz, 1H, Ar—H$_4$), 8.11 (d, J=8.4 Hz, 1H, Ar—H$_3$), 8.28-16 (m, 2H, Ar—H$_{5,8}$), 10.89 (br, 1H, —NH); $^{13}$C-NMR (75 MHz, CDCl$_3$) δ (ppm): 13.82 (SC-CCC), 22.10 (SCCC), 31.55 (SCC), 32.22 (SC), 117.04 (C$_3$), 121.89 (C$_4$), 123.69, 126.74, 127.65, 127.11, 133.40 (C$_8$), 133.84 (C$_5$), 134.04 (C$_7$), 134.22 (C$_6$), 134.53 (C$_2$N), 149.61 (C$_1$N), 158.31 (CS), 182.84 (C$_{10}$O), 185.13 (C$_9$O).

Example 8

2-(2-Methylbenzylthio)-1H-anthra[1,2-d]imidazole-6,11-dione (f1-4)

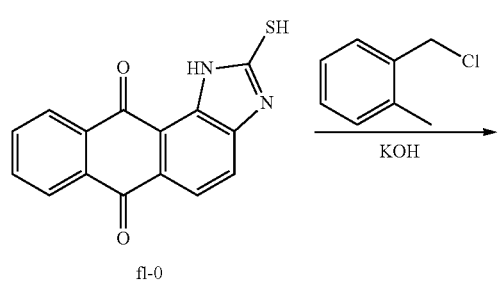

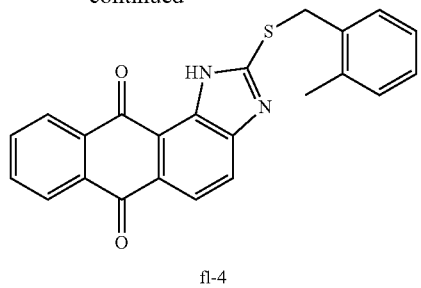

Compound f1-0 (1.4 g, 5 mmole) was dissolved in 30 mL N,N-dimethylformamide, added thereto successively with 1-(chloromethyl)-2-methylbenzene (1.05 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f1-4.

Mol. Wt.: 384.45 (C$_{23}$H$_{16}$N$_2$O$_2$S); Rf: 0.6 (ethyl acetate: dichloromethane=1:6); Yield: 60%; mp: 218° C. (EtOH); IR (KBr) cm$^{-1}$: 1700 (CO); EI-MS m/z: 384 (32.23, M), 386 (5.23, M+1), 352 (19.18, M−1), 76 (32.23), 105 (100); $^1$H-NMR (300 MHz, CDCl$_3$) δ (ppm): 2.47 (s, 3H, Ar'—CH$_3$), 4.7 (s, 3H, SCH$_2$), 7.24 (m, 3H, Ar'—H$_{1,2,3}$), 7.43 (d, J=6.9 Hz, 1H, Ar'—H$_4$), 7.81-7.78 (m, 2H, Ar—H$_{6,7}$), 7.99 (d, J=8.2 Hz, 1H, Ar—H$_4$), 7.81-8.20 (d, J=8.4 Hz, 1H, Ar—H$_3$), 8.35-8.24 (m, 2H, Ar—H$_{5,8}$), 10.85 (1H, br, —NH); $^{13}$C-NMR (75 MHz, CDCl3) δ (ppm): 35.17 (SC), 19.52 (PhC), 117.25, 122.03, 123.91, 126.67, 126.79, 127.77, 127.89, 128.62, 130.45, 130.97, 133.41 (C$_8$), 133.69 (C$_5$), 133.98, 134.06 (C$_7$), 134.24 (C$_6$), 134.61 (C$_2$N), 137.38 (C$_1$N), 149.49 (CS), 157.64, 182.88 (C$_{10}$O), 185.13 (C$_9$O).

Example 9

Methyl-(6,11-dioxo-6,11-dihydro-1H-anthra[1,2-d]imidazol-2-ylthio)butanoate (f1-5)

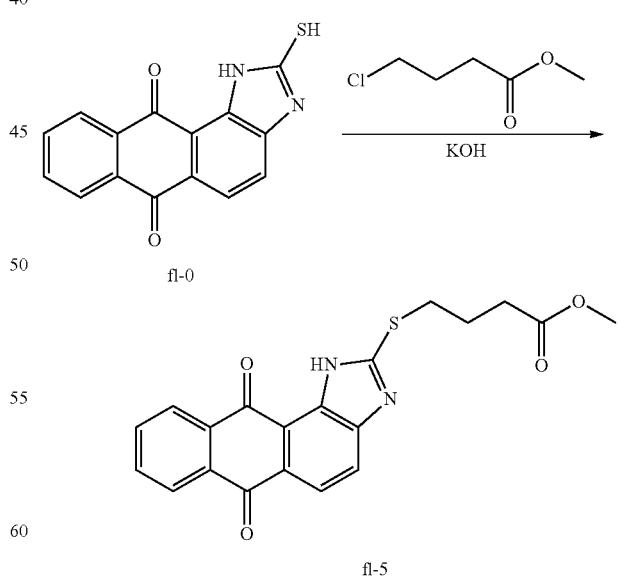

Compound f1-0 (1.4 g, 5 mmole) was dissolved in 30 mL N,N-dimethylformamide, added thereto successively with methyl 4-chlorobutanoate (1.02 g, 7.5 mmol) and KOH (1 equive, 10 mmol) under stirring for 15 hours at room temperature. After completion of reaction, the mixed solution was poured into ice-water (200 mL). Then, the mixture was filtered to collect the precipitate. The precipitate was recrystallized in ethanol to obtain a brown compound f1-5.

Mol. Wt.: 380.42 (C20H16N2O2S); Rf: 0.6 (ethyl acetate: dichloromethane=1:6); Yield: 65%; mp: 194° C. (EtOH); IR (KBr) cm$^{-1}$: 1780 (CO); EI-MS m/z: 380 (7.17, M), 307 (28.95), 280 (100); $^1$H-NMR (300 MHz, CDCl3) δ (ppm): 2.23-2.17 (m, 2H, —CH2-), 2.55 (t, J=7.2, 6.9 Hz, 2H, —CH2-), 3.48 (t, J=7.2 Hz, 2H, S—CH2-), 3.70 (s, 3H, O—CH3-), 7.83-7.76 (m, 2H, Ar—H$_{6,7}$), 7.93 (d, J=8.4 Hz, 1H, Ar—H$_4$), 8.18 (d, J=8.1 Hz, 1H, Ar—H$_3$), 8.35-8.25 (m, 2H, Ar—H$_{5,8}$), 10.83 (br, -1H, NH); $^{13}$C-NMR (75 MHz, CDCl$_3$) δ (ppm): 24.97 (SCCC=O), 29.92 (CC=O), 31.63 (C=O), 32.74 (SC), 52.07 (OC), 117.21, 121.98, 123.86, 126.81 (C$_3$), 127.83 (C$_4$), 133.45 (C$_8$), 133.95 (C$_5$), 134.21 (C$_7$), 134.25 (C$_6$), 134.62 (C$_2$N), 149.52 (C$_1$N), 157.43 (CS), 182.91 (C$_{10}$O), 185.17 (C$_9$O).

Example 10

(E)-methyl 4-(6,11-dioxo-6,11-dihydro-1H-anthra[1,2-d]imidazol-2-ylthio)but-2-enoate (f1-6)

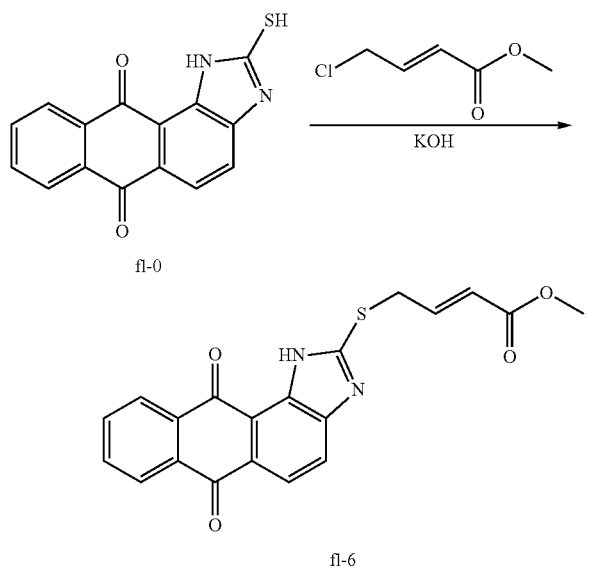

Compound f1-0 (1.4 g, 5 mmole) was dissolved in 30 mL N,N-dimethylformamide, added thereto successively with (E)-methyl 4-chlorobut-2-enoate (1.31 g, 7.5 mmol) and KOH (1 equive, 10 mmol) under stirring for 13 hours at room temperature. After completion of reaction, the mixed solution was poured into ice-water (200 mL). Then, the mixture was filtered to collect the precipitate. The precipitate was recrystallized in ethanol to obtain a yellow compound f1-6.

Mol. Wt.: 378.07 (C20H14N2O4S); Rf: 0.8 (ethyl acetate: n-hexane=3:1); Yield: 70%; mp: 221° C. (EtOH); IR (KBr) cm$^{-1}$: 1708 (CO); ELMS m/z: 378 (11.17, M), 306 (93.13), 281 (50.76), 164 (100); $^1$H-NMR (300 MHz, CDCl$_3$) δ (ppm): 3.72 (s, 3H, O—CH3-), 4.19 (d, J=5.7 Hz, 2H, S—CH2), 6.15 (d, J=14.7 Hz, 1H, C=CH), 7.12-7.07 (m, 1H, HC=C), 7.82-7.78 (m, 2H, Ar—H$_{6,7}$), 7.96 (d, J=8.1 Hz, 1H, Ar—H$_4$), 8.19 (d, J=8.4 Hz, 1H, Ar—H$_3$), 8.35-8.25 (m, 2H, Ar—H$_{5,8}$), 10.98 (1H, br, —NH); $^{13}$C-NMR (75 MHz, CDCl$_3$) δ (ppm):

32.92 (SC), 51.99 (OC), 122.06, 124.15, 124.15, 126.82, 127.83, 134.01 (C$_7$), 134.24 (C$_6$), 134.69 (C$_2$N), 141.92 (C$_1$N), 155.89 (CS), 182 (C$_{10}$O), 184 (C$_9$O).

Example 11

2-(prop-2-ynylthio)-1H-anthra[1,2-d]imidazole-6,11-dione (f1-7)

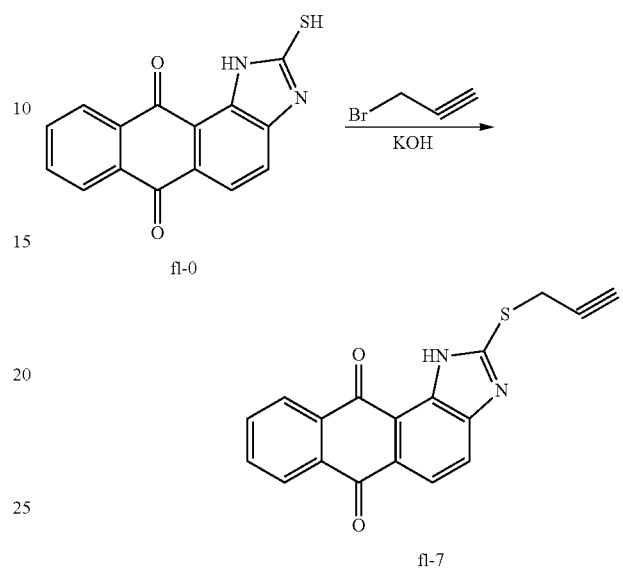

Compound f1-0 (1.4 g, 5 mmole) was dissolved in 30 mL N,N-dimethylformamide, added thereto successively with 3-bromoprop-1-yne (1.21 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a yellow compound f1-7.

Mol. Wt.: 318.35 (C$_{18}$H$_{10}$N$_2$O$_2$S); Rf: 0.8 (ethyl acetate: n-hexane=3:1); Yield: 41%; mp: 132° C. (EtOH); IR (KBr) cm$^{-1}$: 1654 (CO), 3354 (NH); EI-MS m/z: 319 (100, M+1), 320 (26.86, M+2), 317 (74.88, M-1), 281 (6.48); $^1$H-NMR (300 MHz, CDCl3) δ (ppm): 2.47 (s, 1H, —CH), 4.17 (s, 2H, S—CH$_2$), 7.82 (m, 2H, Ar—H$_{6,7}$), 8.0 (d, J=10.5 Hz, 1H, Ar—H$_4$), 8.27 (d, J=10.5 Hz, 1H, Ar—H$_3$), 8.33 (m, 2H, Ar—H$_{5,8}$), 10.83 (br, 1H, —NH); $^{13}$C-NMR (75 MHz, CDCl3) δ (ppm): 27.12 (SC), 68.88 (CC), 177.18, 121.98, 123.81, 126.79, 127.78, 133.45 (C$_8$), 133.95 (C$_5$), 134.12 (C$_7$), 134.25 (C$_6$), 134.62 (C$_2$N), 149.50 (C$_1$N), 157.62 (CS), 182.88 (C$_{10}$O), 185.19 (C$_9$O).

Example 12

2-(4-Chlorobutylthio)-1H-anthra[1,2-d]imidazole-6,11-dione (f1-8)

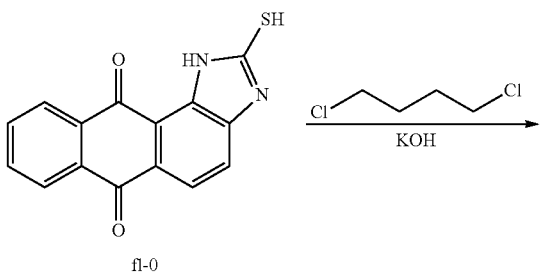

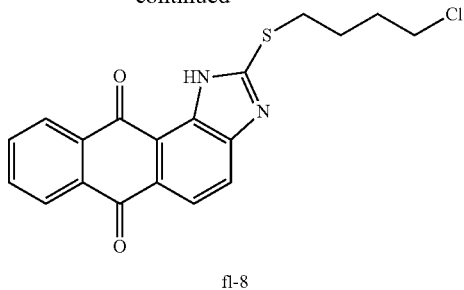

fl-8

Compound f1-0 (1.4 g, 5 mmole) was dissolved in 30 mL N,N-dimethylformamide, added thereto successively with 1,4-dichlorobutane (0.95 g, 7.5 mmol) and KOH (1 equive, 10 mmol) under stirring for 12 hours at room temperature. After completion of reaction, the mixed solution was poured into ice-water (200 mL). Then, the mixture was filtered to collect the precipitate. The precipitate was recrystallized in ethanol to obtain a yellow compound f1-8.

Mol. Wt.: 370.85 (C19H15N2O2SCl); Rf: 0.6 (ethyl acetate:dichloromethane=1:6); Yield: 52%; mp: 178° C. (EtOH); IR (KBr) cm$^{-1}$: 1660 (CO), 3356 (NH);

EI-MS m/z: 370 (7.66, M), 336 (41), 334 (13.5), 281 (100); $^1$H-NMR (300 MHz, CDCl3) δ (ppm): 1.66-1.59 (m, 4H, —CH2CH2-), 3.47 (t, J=6.9 Hz, 2H, S—CH2-), 3.61 (t, J=6.3 Hz, 2H, —CH2-Cl), 7.82-7.78 (2H, m, Ar—H$_{6,7}$), 7.95 (1H, d, J=8.4 Hz, Ar—H$_4$), 8.18 (1H, d, J=8.4 Hz, Ar—H$_3$), 8.35-8.25 (2H, m, Ar—H$_{5,8}$), 10.82 (1H, br, —NH); $^{13}$C-NMR (75 MHz, CDCl$_3$) δ (ppm):

27.02 (SCC), 31.58 (CCCl), 31.67 (SC), 44.45 (CCl), 117.18 (C$_3$), 121.98 (C$_4$), 123.81, 126.79, 127.78, 133.43 (C$_8$), 133.95 (C$_5$), 134.12 (C$_7$), 134.25 (C$_6$), 134.62 (C$_1$N), 149.50 (C$_2$N), 157.62 (CS), 182.88 (C$_{10}$O), 18819 (C$_9$O).

Example 13

2-(5-bromopentylthio)-1H-anthra[1,2-d]imidazole-6,11-dione (f1-9)

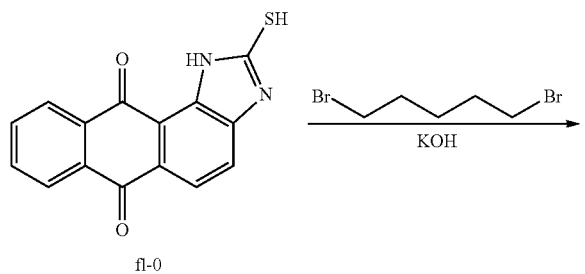

fl-0

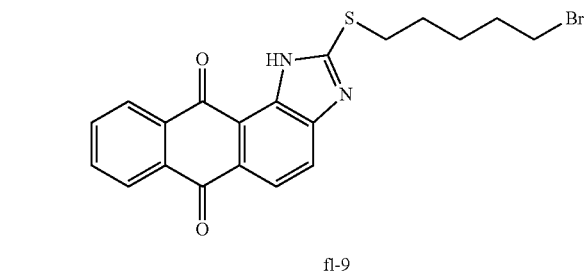

fl-9

Compound f1-0 (1.4 g, 5 mmole) was dissolved in 30 mL 1,4-dioxane, added thereto successively with 1,5-dibromopentane (1.72 g, 7.5 mmol) and KOH (1 equive, 10 mmol) under stirring for 13 hours at room temperature. After completion of reaction, the mixed solution was poured into ice-water (200 mL). Then, the mixture was filtered to collect the precipitate. The precipitate was rainsed with hot ethanol to obtain a brown compound f1-9.

Mol. Wt.: 428.01 (C20H17N2O2SBr); Rf: 0.6 (ethyl acetate:dichloromethane=1:6); Yield: 44%; mp: 222° C. (EtOH); IR (KBr) cm$^{-1}$: 1659 (CO); EI-MS m/z: 428 (6.38, M), 349 (63.64); $^1$H-NMR (300 MHz, CDCl3) δ (ppm): 1.68-1.62 (m, 4H, —CH2CH2-), 1.96-1.87 (m, 3.47-CH2CH2-), 3.44 (t, J=6.6, 6.3 Hz, 4H, S—CH2-CH2-Br), 7.8-7.78 (m, 2H, Ar—H$_{6,7}$), 7.93 (d, J=8.1 Hz, 1H, Ar—H$_4$), 8.34-8.24 (d, J=8.4 Hz, 1H, Ar—H$_3$), 8.34-8.29 (m, 2H, Ar—H$_{5,8}$), 10.85 (1H, br, —NH); $^{13}$C-NMR (75 MHz, CDCl$_3$) δ (ppm): 24.91 (SCCCCBr), 27.43 (SCC, CCBr), 32.33 (SC), 35.58 (CBr), 117.149, 121.97, 123.78 (C$_3$), 126.79 (C$_4$), 127.77 (C$_5$), 128.34 (C$_7$), 131.85 (C$_6$), 149.55 (C$_1$N), 150.21 (C$_2$N), 159.79 (CS), 182.87 (C$_{10}$O), 185.17 (C$_9$O).

Example 14

2-(6-Chlorohexylthio)-1H-anthra[1,2-d]imidazole-6,11-dione (f1-10)

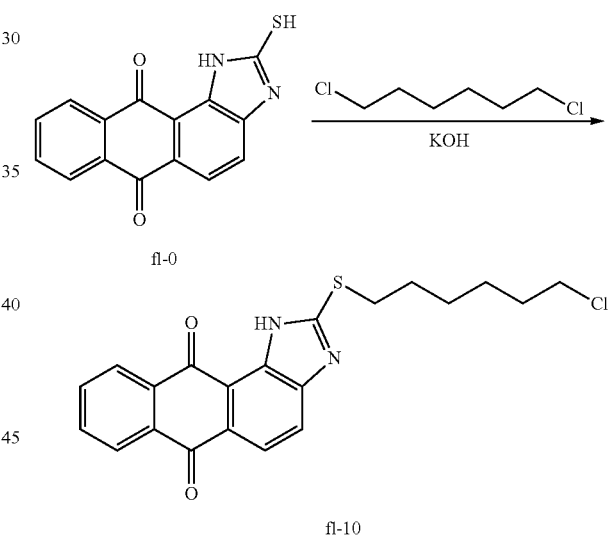

fl-0 fl-10

Compound f1-0 (1.4 g, 5 mmole) was dissolved in 30 mL N,N-dimethylformamide, added thereto successively with 1,6-dichlorohexane (1.163 g, 7.5 mmol) and KOH (1 equive, 10 mmol) under stirring for 13 hours at room temperature. After completion of reaction, the mixed solution was poured into ice-water (200 mL). Then, the mixture was filtered to collect the precipitate. The precipitate was rainsed with hot ethanol to obtain a brown compound f1-10.

Mol. Wt.: 398.91 (C21H19N2O2SCl); Rf: 0.6 (ethyl acetate:dichloromethane=1:6); Yield: 56%; mp: 159° C. (EtOH); IR (KBr) cm$^{-1}$: 1659 (CO), 3353 (NH);

EI-MS m/z: 399 (4.15, M+1), 397 (2.2, M−1), 364 (7.37), 362 (4.46), 281 (100);

$^1$H-NMR (300 MHz, CDCl3) δ (ppm): 1.57-1.54 (m, 4H, —CH2CH2-), 1.85-1.78 (m, 4H, —CH2-CH2-), 3.44 (t, J=7.2, 7.5 Hz, 2H, S—CH2-), 3.54 (t, J=6.6 Hz, 2H, —CH2-Cl), 7.83-7.66 (m, 2H, Ar—H$_{6,7}$), 7.94 (d, J=8.4 Hz, 1H, Ar—H$_4$), 8.17 (d, J=8.1 Hz, 1H, Ar—H$_3$), 8.34-8.24 (m, 2H, Ar—H$_{5,8}$), 10.81 (1H, br, —NH);

$^{13}$C-NMR (75 MHz, CDCl3) δ (ppm): 26.59 (SCCC), 28.17 (CCCCl), 29.43 (SCC), 32.33 (CCCl), 32.61 (SC), 45.15 (CCl), 117.13 (C$_3$), 121.97 (C$_4$), 123.78, 126.79, 127.78, 133.46 (C$_8$), 133.93 (C$_5$), 134.12 (C$_7$), 134.28 (C$_6$), 134.62 (C$_1$N), 149.61 (C$_2$N), 158.03 (CS), 182.91 (C$_{10}$O), 185.23 (C$_9$O).

Example 15

2-(2-(Piperidin-1-yl)ethylthio)-1H-anthra[1,2-d]imidazole-6,11-dione (f1-11)

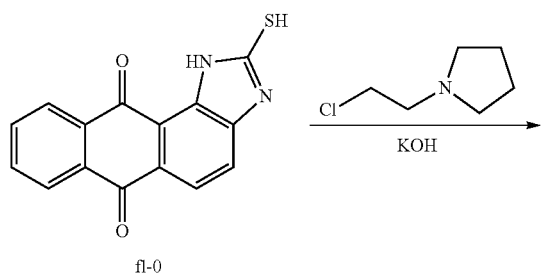

Compound f1-0 (1.4 g, 5 mmole) was dissolved in 30 mL N,N-dimethylformamide, added thereto successively with 1-(2-chloroethyl)pyrrolidine (1.27 g, 7.5 mmol) and KOH (1 equive, 10 mmol) under stirring for 14 hours at room temperature. After completion of reaction, the mixed solution was poured into ice-water (200 mL). Then, the mixture was filtered to collect the precipitate. The precipitate was recrystallized in ethanol to obtain a yellow compound f1-11.

Mol. Wt.: 377.19 (C21H19N3O2S); Rf: 0.8 (ethyl acetate: n-hexane=3:1); Yield: 36%; mp: 159° C. (EtOH); IR (KBr) cm$^{-1}$: 1665.2 (CO), 3356 (NH);

EI-MS m/z: 377 (4.19, M), 281 (8.25), 96 (100); $^1$H-NMR (300 MHz, CDCl3) δ (ppm): 1.99 (m, 4H, —CH2CH2-), 2.86 (m, 2H, N—(CH2)2-), 3.10 (t, J=5.7, 5.4 Hz, 2H, N—CH2-), 3.38 (t, J=5.4, 5.7 Hz, 2H, S—CH2-), 7.81-7.25 (m, 2H, Ar—H$_{6,7}$), 7.92 (d, J=8.1 Hz, 1H, Ar—H$_4$), 8.16 (d, J=8.1 Hz, 1H, Ar—H$_3$), 8.33-8.20 (m, 2H, Ar—H$_{5,8}$), 10.18 (br, 1H, —NH); $^{13}$C-NMR (75 MHz, CDCl3) δ (ppm): 23.84 (NCC), 31.90 (SC), 55.10 (NC), 58.83 (CN), 117.74 (C$_3$), 121.77 (C$_4$), 126.44, 126.64, 127.57, 127.66, 133.48 (C$_8$), 133.801 (C$_5$), 134.13 (C$_7$), 134.22 (C$_6$), 134.28 (C$_1$N), 134.39 (C$_2$N), 159.06 (CS), 183.20 (C$_{10}$O), 184.41 (C$_9$O).

Example 16

2-(2-(Piperidin-1-yl)ethylthio)-1H-anthra[1,2-d]imidazole-6,11-dione (f1-12)

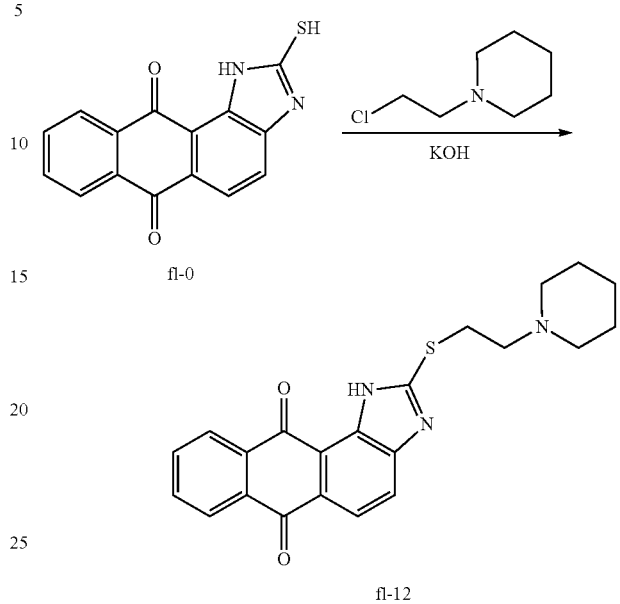

Compound f1-0 (1.4 g, 5 mmole) was dissolved in 30 mL N,N-dimethylformamide, added thereto successively with 1-(2-chloroethyl)piperidine (1.38 g, 7.5 mmol) and KOH (1 equive, 10 mmol) under stirring for 9 hours at room temperature. After completion of reaction, the mixed solution was poured into ice-water (200 mL). Then, the mixture was filtered to collect the precipitate. The precipitate was recrystallized in ethanol to obtain a yellow compound f1-12.

Mol. Wt.: 391.49 (C22H21N3O2S); Rf: 0.8 (ethyl acetate: n-hexane=3:1); Yield: 56%; mp: 162° C. (EtOH); IR (KBr) cm$^{-1}$: 1659.8 (CO) 3354.5 (NH);

EI-MS m/z: 391 (1.04, M), 392 (1.72, M+1), 393 (0.52, M), 111 (100);

$^1$H-NMR (300 MHz, CDCl3) δ (ppm): 1.67-1.63 (m, 2H, —CH2-), 2.62 (t, J=5.1, 5.4 Hz, 4H—CH2-CH2-), 2.87 (t, J=6.6, 6.3 Hz, 2H N—CH2-), 3.5 (t, J=6.5, 6.3 Hz, 2H S—CH2-), 7.80-7.26 (m, 2H, Ar—H$_{6,7}$), 7.93 (d, J=8.1 Hz, 1H, Ar—H$_4$), 8.17 (d, J=8.1 Hz, 1H, Ar—H$_3$), 8.34-8.25 (m, 2H, Ar—H$_{5,8}$), 10.86 (br, 1H, —NH); $^{13}$C-NMR (75 MHz, CDCl3) δ (ppm): 24.56 (NCCC), 25.22 (NCC), 30.65 (SC), 54.49 (NC), 58.12 (CN), 117.74 (C$_3$), 121.89 (C$_4$), 123.69, 126.74, 127.67, 127.68 (C$_8$), 133.52 (C$_5$), 133.87 (C$_7$), 134.21 (C$_6$), 134.45 (C$_1$N), 149.85 (C$_2$N), 158.67 (CS), 183.03 (C$_{10}$O), 184.82 (C$_9$O).

Example 17

2-(2-morpholinoethylthio)-1H-anthra[1,2-d]imidazole-6,11-dione (f1-13)

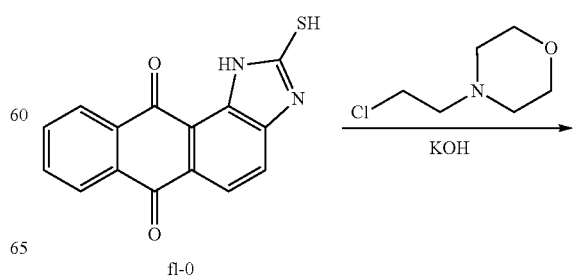

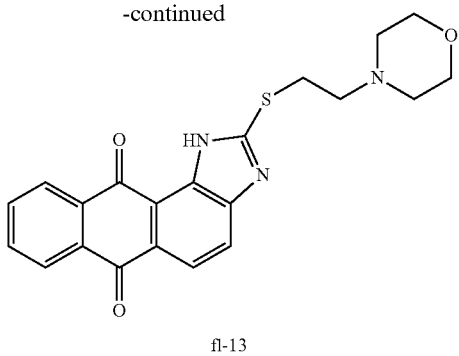

fl-13

Compound fl-0 (1.4 g, 5 mmole) was dissolved in 30 mL N,N-dimethylformamide, added thereto successively with 4-(2-chloroethyl)morpholine (1.39 g, 7.5 mmol) and KOH (1 equive, 10 mmol) under stirring for 12 hours at room temperature. After completion of reaction, the mixed solution was poured into ice-water (200 mL). Then, the mixture was filtered to collect the precipitate. The precipitate was recrystallized in ethanol to obtain a red compound fl-13.

Mol. Wt.: 393.11 ($C_{21}H_{19}N_3O_3S$); Rf: 0.8 (ethyl acetate: n-hexane=3:1); Yield: 54%; mp: 178° C. (EtOH); IR (KBr) cm$^{-1}$: 1654 (CO), 333.68 (CO); EI-MS m/z: 393 (2.88, M), 281 (10.16), 113 (100); $^1$H-NMR (300 MHz, CDCl$_3$) δ (ppm): 2.60 (t, J=6.6, 6.9 Hz, 4H, —N(CH$_2$)$_2$), 2.86 (t, J=6.6 Hz, 2H, —CH$_2$N), 3.55 (t, J=6.6 Hz, 2H, —SCH$_2$), 3.76 (dd, J=4.5, 4 Hz, 4H, —O(CH2)2), 7.93-7.74 (m, 2H, Ar—H$_{5,8}$), 8.03 (d, J=8.1 Hz, 1H, Ar—H$_4$), 8.17 (d, J=8.4 Hz, 1H, Ar—H$_3$), 8.34-8.24 (m, 2H, Ar—H$_{6,7}$), 11.2 (s, 1H, NH); $^{13}$C-NMR (75 MHz, CDCl3) δ (ppm): 30.07 (SC), 54.19 (NC)), 58.02 (CN), 66.87 (CO), 117.27 (C$_3$), 121.95 (C$_4$), 126.44, 126.78, 127.73, 133.42 (C$_8$), 133.94 (C$_5$), 134.06 (C$_7$), 134.19 (C$_6$), 134.39 (C$_1$N), 149.61 (C$_2$N), 158.11 (CS), 182.90 (C$_{10}$O), 184.97 (C$_9$O).

Example 18

2-(3-(piperidin-1-yl)propylthio)-1H-anthra[1,2-d]imidazole-6,11-dione (fl-14)

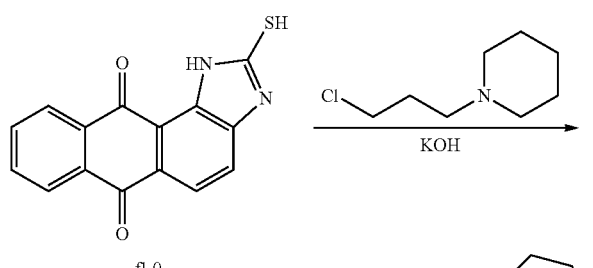

fl-14

Compound fl-0 (1.4 g, 5 mmole) was dissolved in 30 mL N,N-dimethylformamide, added thereto successively with 1-(3-chloropropyl)piperidine (1.53 g, 7.5 mmol) and KOH (1 equive, 10 mmol) under stirring for 11 hours at room temperature. After completion of reaction, the mixed solution was poured into ice-water (200 mL). Then, the mixture was filtered to collect the precipitate. The precipitate was recrystallized in ethanol to obtain a red compound fl-14.

Mol. Wt.: 405.51 ($C_{23}H_{23}N_3O_2S$); Rf: 0.8 (ethyl acetate: n-hexane=3:1); Yield: 41%; mp: 161.3° C. (EtOH); IR (KBr) cm$^{-1}$: 1628.3 (CO), 3355.5 (NH);

EI-MS m/z: 405 (3.08, M); $^1$H-NMR (300 MHz, CDCl$_3$) δ (ppm): 1.47-1.40 (m, 2H, —CH2-), 1.63-1.59 (m, 4H, —CH2-CH2-), 2.04 (m, 2H, —CH2-), 2.41 (m, 4H, —N(CH$_2$)$_2$), 2.50 (t, J=6.9, 7.2 Hz, 2H, —CH$_2$N), 3.45 (t, J=6.9, 7.2 Hz, 2H, —SCH$_2$), 7.79 (m, 2H, Ar—H$_{5,8}$), 7.94 (d, J=8.1 Hz, 1H, Ar—H$_4$), 8.17 (d, J=8.4 Hz, 1H, Ar—H$_3$), 8.29 (m, 2H, Ar—H$_{6,7}$), 10.2 (s, 1H, NH); $^{13}$C-NMR (75 MHz, CDCl3) δ (ppm): 29.99 (SCCCN), 30.67 (SC), 54.73 (NC), 57.70 (CN), 117.14 (C$_3$), 121.89 (C$_4$), 126.74, 126.69, 127.43, 133.43 (C$_8$), 133.86 (C$_5$), 134.07 (C$_7$), 134.28 (C$_6$), 134.50 (C$_1$N), 149.59 (C$_2$N), 158.31 (CS), 182.85 (C$_{10}$O), 185.03 (C$_9$O).

Example 19

2-(3-(dimethylamino)propylthio)-1H-anthra[1,2-d]imidazole-6,11-dione (fl-15)

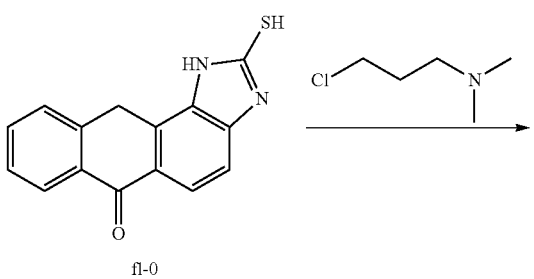

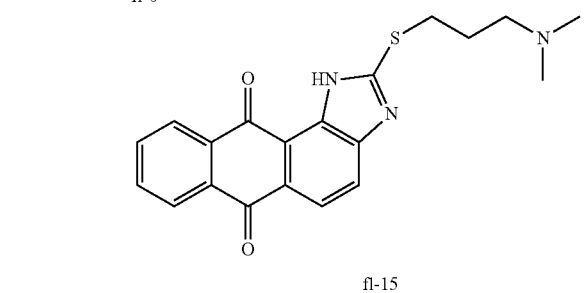

fl-15

Compound fl-0 (1.4 g, 5 mmole) was dissolved in 30 mL N,N-dimethylformamide, added thereto successively with 3-chloro-N,N-dimethylpropan-1-amine (1.41 g, 8.9 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a yellow compound fl-15.

Mol. Wt.: 365.44 ($C_{20}H_{19}N_3O_2S$); Rf: 0.8 (ethyl acetate: n-hexane=3:1); Yield: 55%; mp: 155.9° C. (EtOH); IR (KBr) cm$^{-1}$: 1667.4 (CO), 3357.2 (NH);

EI-MS m/z: 365 (1.03, M); $^1$H-NMR (300 MHz, CDCl$_3$) δ (ppm): 2.04 (t, J=6.3, 6.9 Hz, 2H, —CH2-), 2.37 (s, 6H, N—(CH3)2-), 2.63 (t, J=6.3, 6.0 Hz, 2H, —CH2-), 3.44 (t, J=6.3, 6.9 Hz 2H, —SCH$_2$), 2.51 (t, J=6.9 Hz, 2H, —CH$_2$N), 3.46 (t, J=6.9 Hz, 2H, —SCH$_2$), 7.79-7.26 (m, 2H, Ar—H$_{5,8}$), 7.87 (d, J=8.4 Hz, 1H, Ar—H$_4$), 8.13 (d, J=8.4 Hz, 1H, Ar—H$_3$), 8.33-8.25 (m, 2H, Ar—H$_{6,7}$); $^{13}$C-NMR (75 MHz, CDCl3) δ (ppm): 25.25 (SCCCN), 30.55 (SC), 44.95 (NC), 58.22 (CN), 117.22 (C$_3$), 121.89 (C$_4$), 123.67, 126.74, 127.68, 127.72, 133.52 (C$_8$), 133.82 (C$_5$), 134.23 (C$_{7,6}$), 134.45 (C$_1$N), 149.85, (C$_2$N), 158.62 (CS), 183.02 (C$_{10}$O), 184.82 (C$_9$O).

Example 20

2-(2-morpholino-2-oxoethylthio)-1H-anthra[1,2-d]imidazole-6,11-dione (f1-16)

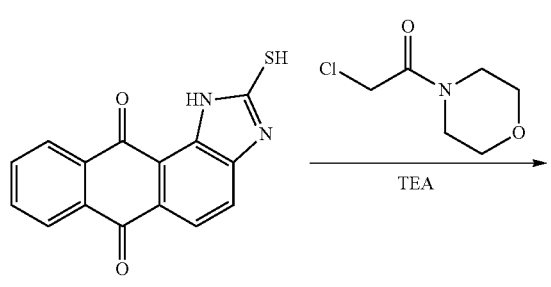

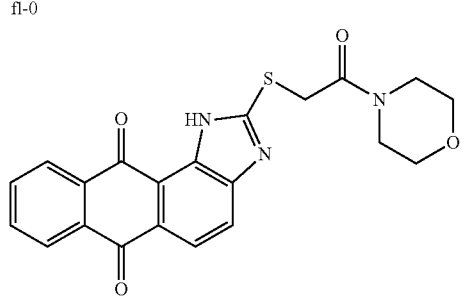

Compound f1-0 (1.4 g, 5 mmole) was dissolved in 30 mL N,N-dimethylformamide, added thereto successively with 2-chloro-1-morpholinoethanone (1.33 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a yellow compound f1-16.

Mol. Wt.: 407.44 (C$_{21}$H$_{17}$N$_3$O$_4$S); Rf: 0.8 (ethyl acetate: n-hexane=3:1); Yield: 53%; mp: 280.3° C. (EtOH); IR (KBr) cm$^{-1}$: 1646 (CO), 3245 (NH);

EI-MS m/z: 407 (13.54, M); $^1$H-NMR (300 MHz, CDCl$_3$) δ (ppm): 3.65 (m, 4H, —CH$_2$— —CH2-), 3.77-3.75 (m, 4H, —CH2- —CH2-), 4.18 (s, 2H, CO—CH$_2$-), 7.80 (m, 2H, Ar—H$_{5,8}$), 7.93 (d, J=8.4 Hz, 1H, Ar—H$_4$), 8.19 (d, J=8.4 Hz, 1H, Ar—H$_3$), 8.33 (m, 2H, Ar—H$_{6,2}$); $^{13}$C-NMR (75 MHz, CDCl$_3$) δ (ppm): 34.27 (SC), 47.62 (NC), 65.64 (CO), 118.02 (C$_3$), 121.91 (C$_4$), 123.98, 127.12, 127.52, 128.03, 133.58 (C$_8$), 133.74 (C$_5$), 133.91 (C$_2$), 134.67 (C$_6$), 134.35 (C$_1$N), 149.61 (C$_2$N), 157.03 (CS), 167.64 (C=O), 183.19 (C$_{10}$O), 184.55 (C$_9$O).

Example 21

2-(3-morpholino-3-oxopropylthio)-1H-anthra[1,2-d]imidazole-6,11-dione (f1-17)

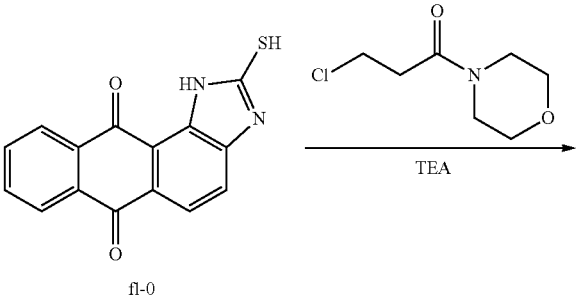

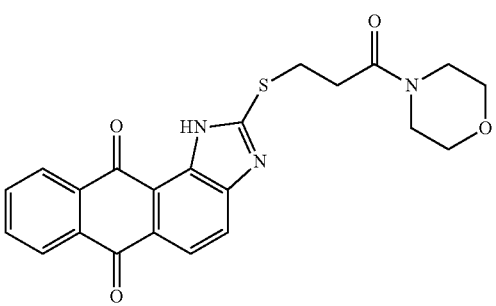

Compound f1-0 (1.4 g, 5 mmole) was dissolved in 30 mL N,N-dimethylformamide, added thereto successively with 3-chloro-1-morpholinoethanone (1.33 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f1-17.

Mol. Wt.: 421.46 (C$_{22}$H$_{19}$N$_3$O$_4$S); Rf: 0.8 (ethyl acetate: n-hexane=3:1); Yield: 56%; mp: 243.1° C. (EtOH); IR (KBr) cm$^{-1}$: 1644 (CO), 2920 (NH); EI-MS m/z: 421 (11.54, M); $^1$H-NMR (300 MHz, CDCl$_3$) δ (ppm): 2.98 (t, J=6.6, 6.3 Hz 2H, CO—CH2-), 3.50 (br, 2H, —SCH$_2$), 3.69 (m, 8H, —(CH$_2$)$_2$N), 7.81-7.80 (m, 2H, Ar—H$_{5,8}$), 7.92 (d, J=7.8 Hz, 1H, Ar—H$_4$), 8.18 (d, J=8.1 Hz, 1H, Ar—H$_3$), 8.32 (m, 2H, Ar—H$_{6,7}$), 11.2 (s, 1H, NH); $^{13}$C-NMR (75 MHz, CDCl$_3$) δ (ppm): 29.74, (SCCC=O), 34.22 (SC), 47.62 (NC), 65.62 (CO), 118.02 (C$_3$), 121.91 (C$_4$), 123.98, 127.02, 127.52, 128.03, 133.58 (C$_8$), 133.74 (C$_5$), 133.91 (C$_7$), 134.06 (C$_6$), 134.35 (C$_1$N), 149.61 (C$_2$N), 157.03 (CS), 168.04 (C=O), 183.19 (C$_{10}$O), 184.55 (C$_9$O).

Example 22

2-(6,11-dioxo-6,11-dihydro-1H-anthra[1,2-d]imidazol-2-ylthio)-N,N-diethylacetamide (f1-18)

Example 23

2-(allylthio)-1H-anthra[1,2-d]imidazole-6,11-dione (f1-19)

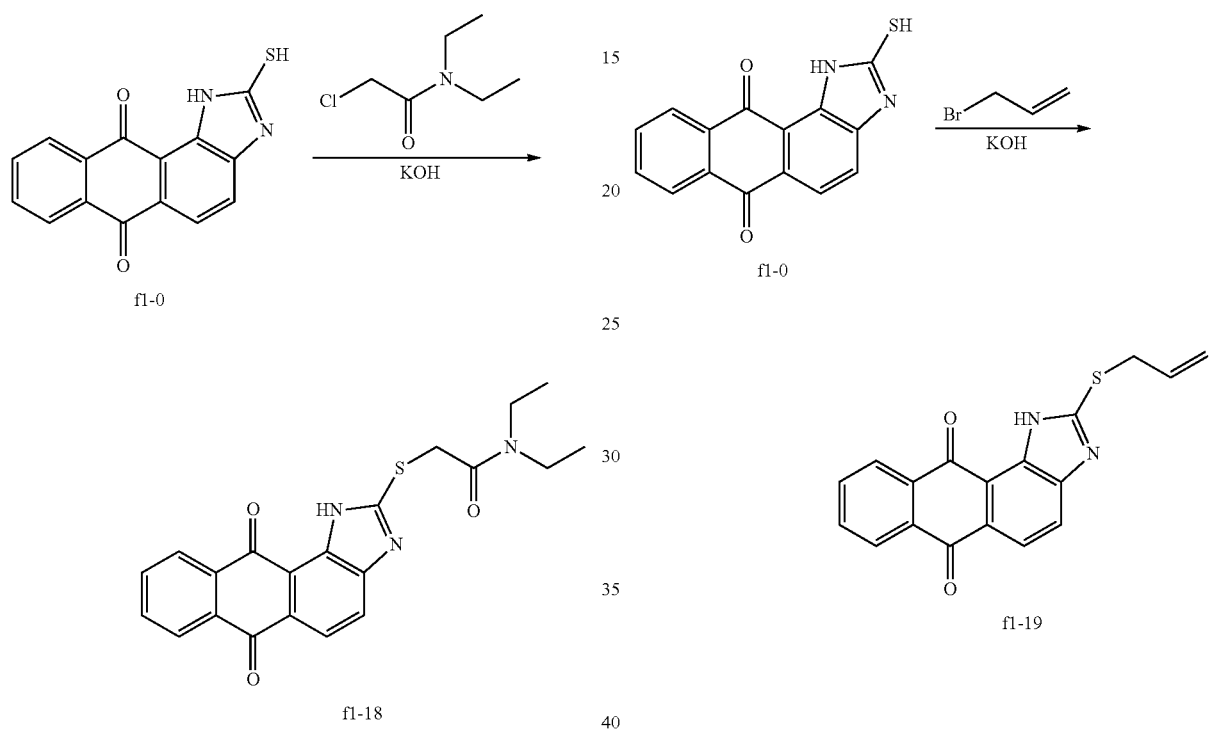

Compound f1-0 (1.4 g, 5 mmole) was dissolved in 30 mL N,N-dimethylformamide, added thereto successively with 2-chloro-N,N-diethylacetamide (1.23 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f1-18.

Mol. Wt.: 393.11 ($C_{21}H_{19}N_3O_3S$); Rf: 0.8 (ethyl acetate: n-hexane=3:1); Yield: 66%; mp: 219.6° C. (EtOH); IR (KBr) cm$^{-1}$: 1659 (CO), 3355 (NH);

EI-MS m/z: 393 (35.56, M), 394 (3.57, M+1); $^1$H-NMR (300 MHz, CDCl$_3$) δ (ppm): 1.21 (t, J=7.2 Hz, 3H, —CH3-), 1.32 (t, J=7.2 Hz, 3H, —CH3), 3.48 (q, J=7.2 Hz, 2H, —CH2-), 3.56 (q, J=7.2 Hz 2H, —CH$_2$), 7.78 (m, 2H, Ar—H$_{5,8}$), 7.92 (d, J=8.4 Hz, 1H, Ar—H$_4$), 8.18 (d, J=8.4 Hz, 1H, Ar—H$_3$), 8.32 (m, 2H, Ar—H$_{6,7}$); $^{13}$C-NMR (75 MHz, CDCl$_3$) δ (ppm): 13.13 (NCC), 14.79 (NCC), 33.52, (SCC=O), 41.43 (NC), 43.36 (NC), 117.93 (C$_3$), 122.00 (C$_4$), 123.83, 127.08, 127.61, 128.09, 133.55 (C$_8$), 133.66 (C$_5$), 133.66 (C$_7$), 133.92 (C$_6$), 134.15 (C$_1$N), 134.39 (C$_2$N), 149.27 (CS), (C=O), 183.19 (C$_{10}$O), 184.55 (C$_9$O).

Compound f1-0 (1.4 g, 5 mmole) was dissolved in 30 mL N,N-dimethylformamide, added thereto successively with 3-bromoprop-1-ene (1.78 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a yellow compound f1-19.

Mol. Wt.: 320.37 ($C_{18}H_{12}N_2O_{52}S$); Rf: 0.8 (ethyl acetate: n-hexane=3:1); Yield: 41%; mp: 303° C. (EtOH); IR (KBr) cm$^{-1}$: 1654 (CO), 3352 (NH);

EI-MS m/z: 320 (M); $^1$H-NMR (300 MHz, CDCl$_3$) δ (ppm): 4.06 (d, 2H, S—CH), 5.27 (d, J=10.2 Hz, 1H, C=CH$_2$), 5.46 (d, J=16.5 Hz, 1H, C=CH$_2$), 6.13-6.02 (m, 2H, —CH=CH$_2$), 7.79 (m, 2H, Ar—H$_{6,2}$), 7.94 (d, J=8.4 Hz, 1H, Ar—H$_4$), 8.17 (d, J=8.1 Hz, 1H, Ar—H$_3$), 8.33-8.24 (m, 2H, Ar—H$_{5,8}$), 10.91 (br, 1H, —NH); $^{13}$C-NMR (75 MHz, CDCl$_3$) δ (ppm): 27.12 (SC), 118.18 (CC), 121.98, 123.81, 126.79, 127.78 (CC), 133.48 (C$_8$), 133.85 (C$_5$), 134.12 (C$_2$), 134.28 (C$_6$), 134.62 (C$_2$N), 149.58 (C$_1$N), 157.68 (CS), 182.88 (C$_{10}$O), 185.18 (C$_9$O).

Example 24

3-(6,11-dioxo-6,11-dihydro-1H-anthra[1,2-d]imidazol-2-ylthio)-N,N-diethylpropanamide (f1-20)

Example 25

2-(2-oxo-2-(pyrrolidin-1-yl)ethylthio)-1H-anthra[1,2-d]imidazole-6,11-dione (f1-21)

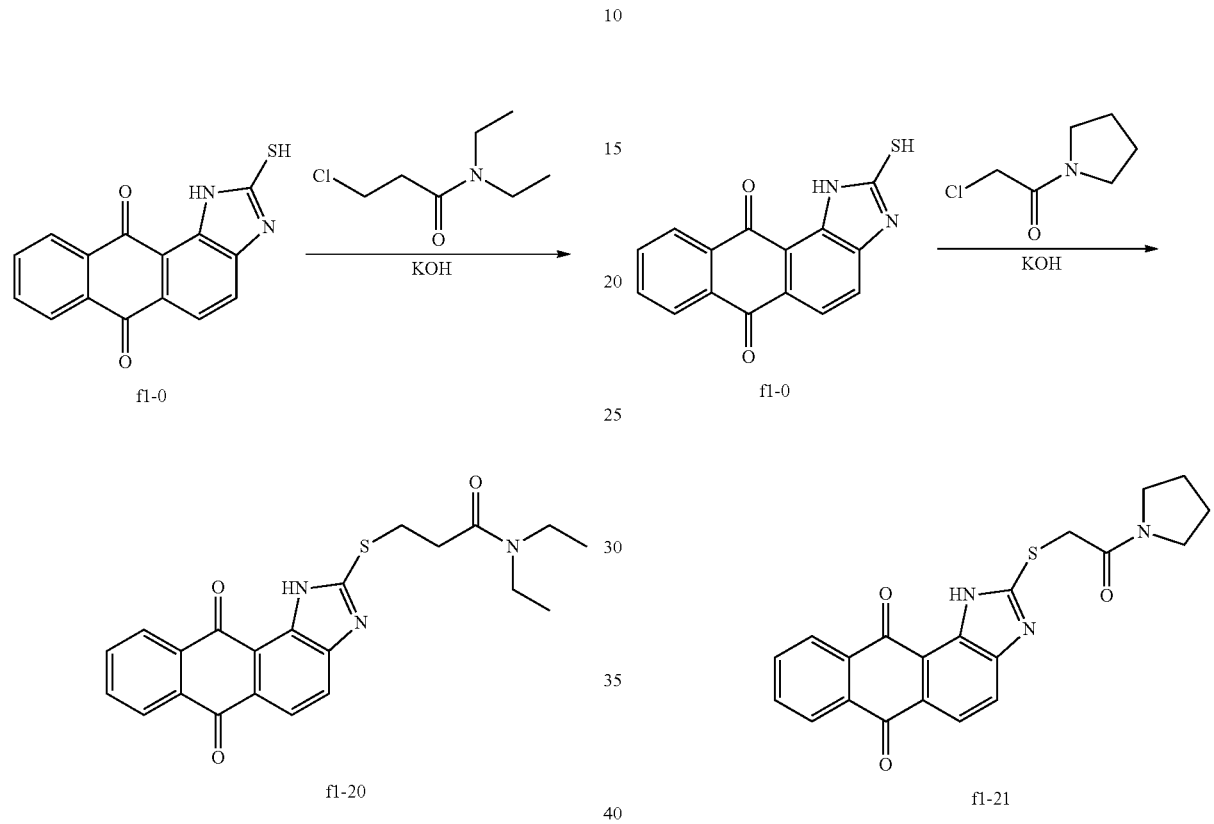

Compound f1-0 (1.4 g, 5 mmole) was dissolved in 30 mL N,N-dimethylformamide, added thereto successively with 3-chloro-N,N-diethylpropanamide (1.48 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f1-20.

Mol. Wt.: 407.13 ($C_{22}H_{21}N_3O_3S$); Rf: 0.8 (ethyl acetate: n-hexane=3:1); Yield: 61%; mp: 387.5° C. (EtOH); IR (KBr) $cm^{-1}$: 1559.0 (CO), 3355.1 (NH); EI-MS m/z: 407.1 (M); $^1$H-NMR (300 MHz, $CDCl_3$) δ (ppm): 1.16-1.11 (m, 6H, —($CH3$)$_2$-), 3.04 (t, J=6.3, 6.9 Hz 2H, —COCH2-), 3.31 (q, J=6.3, 6.9 Hz, 2H, N—CH2-), 2.42 (q, J=7.2, 6.9 Hz, 2H, N—CH2-), 3.67 (t, J=6.6, 6.3 Hz, 2H, S—$CH_2$), 7.80-7.25 (m, 2H, Ar—$H_{5,8}$), 7.89 (d, J=8.1 Hz, 1H, Ar—$H_4$), 8.15 (d, J=8.4 Hz, 1H, Ar—$H_3$), 8.26-8.23 (m, 2H, Ar—$H_{6,2}$), 11.19 (br, 1H, —NH); $^{13}$C-NMR (75 MHz, $CDCl_3$) δ (ppm): 13.34 (NCC), 14.46 (NCC), 30.97 (SC), 33.76 (SCC=O), 41.41 (NC), 42.11 (NC), 117.30 ($C_3$), 121.85 ($C_4$), 126.82, 126.93, 127.11, 133.45 ($C_8$), 133.89 ($C_5$), 134.10 ($C_2$), 134.45 ($C_6$), 134.76 ($C_1$N), 149.53, 158.48 ($C_2$N), 169.39 (CS), 170.26 (C=O), 182.91 ($C_{10}$O), 184.88 ($C_9$O).

Compound f1-0 (1.4 g, 5 mmole) was dissolved in 30 mL N,N-dimethylformamide, added thereto successively with 2-chloro-1-(pyrrolidin-1-yl)ethanone (1.48 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f1-21.

Mol. Wt.: 391.14 ($C_{21}H_{17}N_3O_3S$); Rf: 0.8 (ethyl acetate: n-hexane=3:1); Yield: 60%; mp: 346° C. (EtOH); IR (KBr) $cm^{-1}$1: 1662.4 (CO), 3279 (NH); EI-MS m/z: 391.1 (M); $^1$H-NMR (300 MHz, $CDCl_3$) δ (ppm): 2.21-2.93 (m, 4H, —CH2-CH2-), 3.66-3.63 (m, 4H, N—(CH2)2-), 3.99 (s, 2H, COCH2-), 7.76-7.25 (m, 2H, Ar—$H_{5,8}$), 7.91 (d, J=8.1 Hz, 1H, Ar—$H_4$), 8.16 (d, J=8.1 Hz, 1H, Ar—$H_3$), 8.29 (m, 2H, Ar—$H_{6,7}$) 13.10 (br, 1H, —NH); $^{13}$C-NMR (75 MHz, $CDCl_3$) δ (ppm): 24.65 (NCC), 26.36 (NCC), 34.07 (SC), 47.04 (NC), 47.62 (NC), 118.00 ($C_3$), 121.91 ($C_4$), 123.98, 127.11, 127.58 ($C_8$), 128.03 ($C_5$), 133.58 ($C_7$), 133.74 ($C_6$), 133.90 ($C_1N$), 134.17, 134.35, 149.61 ($C_2N$), 157.03 (CS), 167.61 (C=O), 183.91 ($C_{10}O$), 184.55 ($C_9O$).

Example 26

2-(3-oxo-3-(pyrrolidin-1-yl)propylthio)-1H-anthra[1,2-d]imidazole-6,11-dione (f1-22)

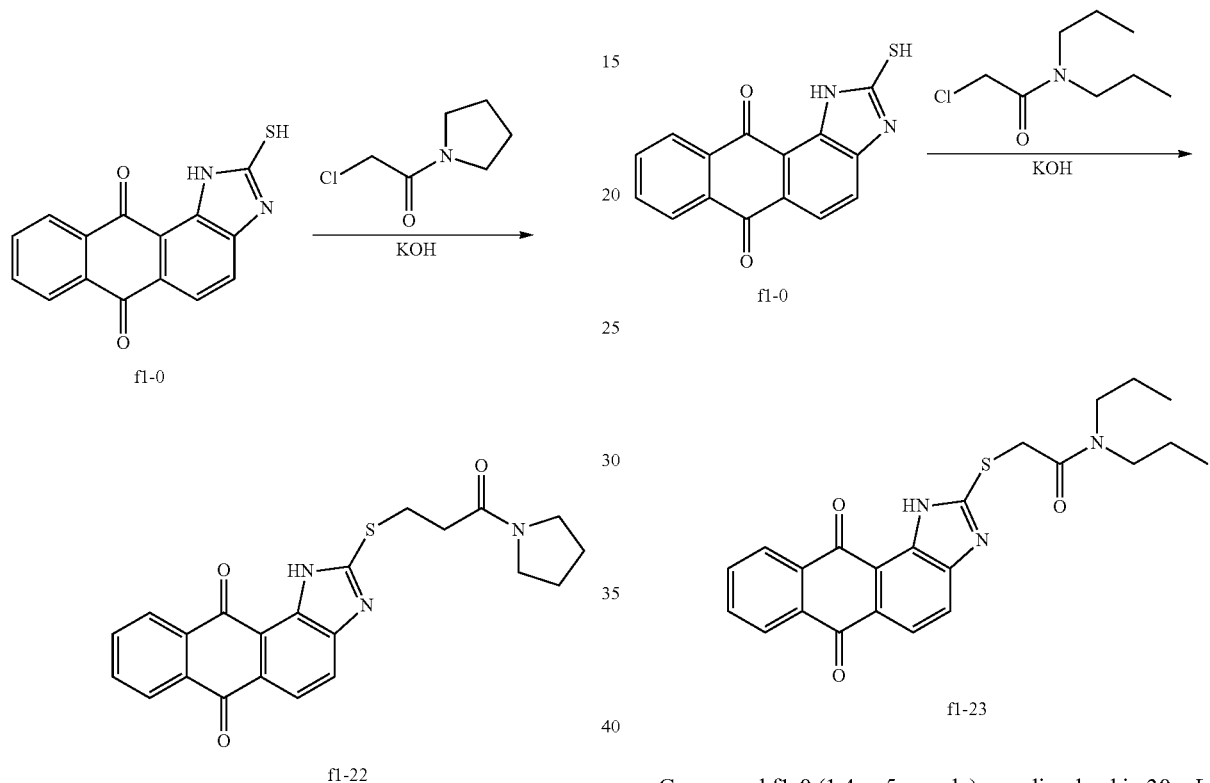

Compound f1-0 (1.4 g, 5 mmole) was dissolved in 30 mL N,N-dimethylformamide, added thereto successively with 3-chloro-1-(pyrrolidin-1-yl)propan-1-one (1.45 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f1-22.

Mol. Wt.: 405.47 ($C_{22}H_{19}N_3O_3S$); Rf: 0.8 (ethyl acetate: n-hexane=3:1); Yield: 54%; mp: 244.6° C. (EtOH); IR (KBr) $cm^{-1}$: 1662 (CO), 3376 (NH); EI-MS m/z: 405.1 (M); $^1$H-NMR (300 MHz, $CDCl_3$) δ (ppm): 1.99-1.81 (m, 2H, —CH2-CH2-), 2.91 (t, J=6.9 Hz, 2H, —COCH2-), 3.36 (t, J=6.5 Hz 2H, N—CH2-), 3.44 (t, J=6.5 Hz 2H, —$NCH_2$), 3.67 (t, J=6.3 Hz, 2H, $SCH_2$—), 7.82-7.25 (m, 2H, Ar—$H_{5,8}$), 7.91 (d, J=8.4 Hz, 1H, Ar—$H_4$), 8.16 (d, J=8.4 Hz, 1H, Ar—$H_3$), 8.32-8.23 (m, 2H, Ar—$H_{6,7}$), 11.50 (br, 1H, —NH); $^{13}$C-NMR (75 MHz, $CDCl_3$) δ (ppm): 25.74 (NCC), 26.22 (NCC), 29.90 (SC), 32.654 (SCCC=ON), 40.98 (NC), 46.13 (NC), 117.39 ($C_3$), 121.86 ($C_4$), 123.69, 126.87, 127.68 ($C_8$), 130.15 ($C_5$), 133.51 ($C_7$), 133.92 ($C_6$), 134.48 ($C_1N$), 134.95, 134.48, 149.66 ($C_2N$), 158.43 (CS), 164.66 (C=O), 184.02 ($C_{10}O$), 184.90 ($C_9O$).

Example 27

2-(6,11-dioxo-6,11-dihydro-1H-anthra[1,2-d]imidazol-2-ylthio)-N,N-dipropylacetamide (f1-23)

Compound f1-0 (1.4 g, 5 mmole) was dissolved in 30 mL N,N-dimethylformamide, added thereto successively with 2-chloro-N,N-dipropylacetamide (1.55 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f1-23.

Mol. Wt.: 421.51 ($C_{23}H_{23}N_3O_3S$); Rf: 0.8 (ethyl acetate: n-hexane=3:1); Yield: 55%; mp: 193.6° C. (EtOH); IR (KBr) $cm^{-1}$: 1654.5 (CO), 3356 (NH);

EI-MS m/z: 421.1 (M); $^1$H-NMR (300 MHz, $CDCl_3$) δ (ppm): 0.90 (t, J=7.2 Hz 3H, —$CH_3$—), 0.98 (t, J=7.2 Hz, 3H, —CH3-), 1.74-1.56 (m, 4H, —CH2-CH2), 3.37 (t, J=7.5 Hz 4H, —$NCH_2$), 3.43 (t, J=7.5 Hz, 2H, —$CH_2N$), 4.12 (s, 2H, —$SCH_2$), 7.77-7.69 (m, 2H, Ar—$H_{5,8}$), 7.91 (d, J=8.4 Hz, 1H, Ar—$H_4$), 8.17 (d, J=8.4 Hz, 1H, Ar—$H_3$), 8.26-8.24 (m, 2H, Ar—$H_{6,7}$), 12.74 (br, 1H, —NH); $^{13}$C-NMR (75 MHz, CDCl3) δ (ppm): 11.50 (NCCC), 20.96 (NCC), 22.70 (NCC), 24.70 (SC), 48.57 (NC), 50.77 (NC), 117.82 ($C_3$), 121.85 ($C_4$), 123.83, 126.99, 127.55 ($C_8$), 127.95 ($C_5$), 133.49 ($C_7$), 133.70 ($C_6$), 133.87 ($C_1N$), 134.09, 134.33, 149.52 ($C_2N$), 157.26 (CS), 168.87 (C=O), 184.06 ($C_{10}O$), 184.48 ($C_9O$).

Example 28

S-6,11-dioxo-6,11-dihydro-1H-anthra[1,2-d]imidazol-2-yl 2-nitrobenzothioate (f2-1)

Example 29

S-6,11-dioxo-6,11-dihydro-1H-anthra[1,2-d]imidazol-2-yl morpholine-4-carbothioate (f2-2)

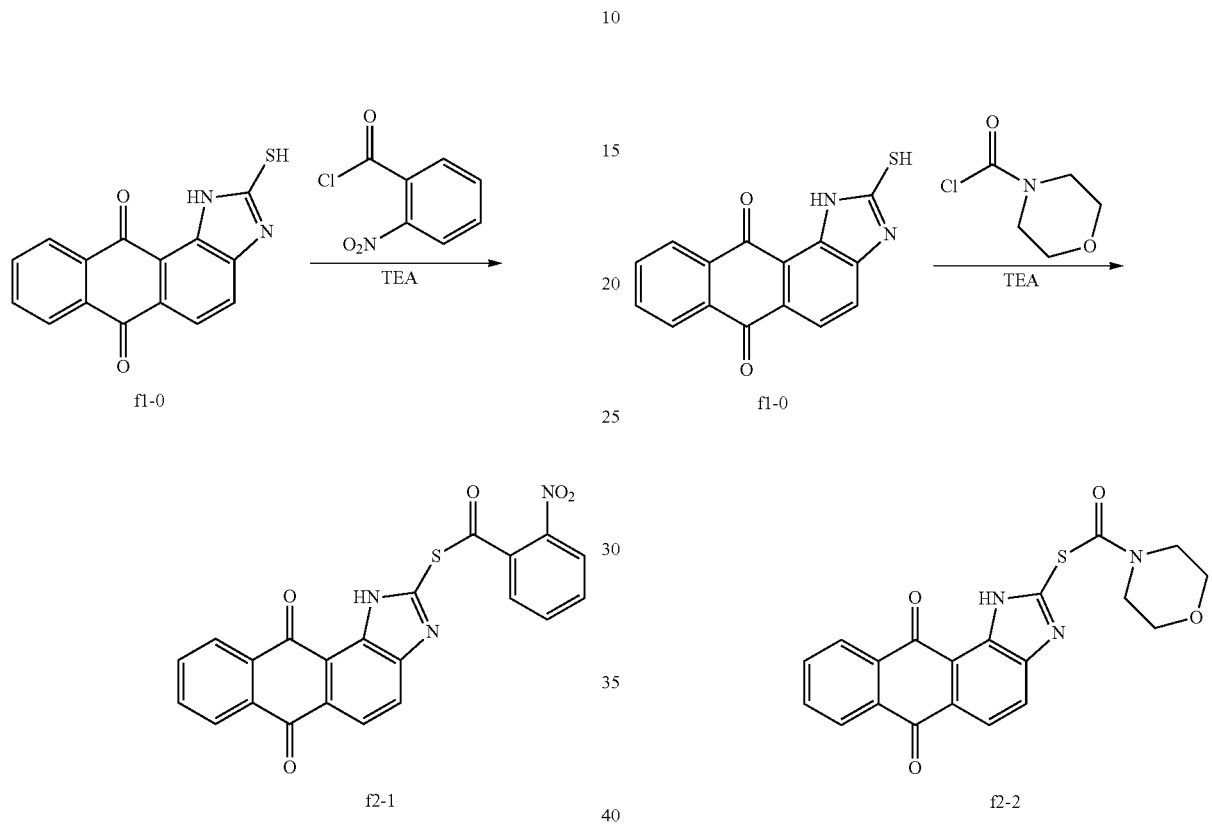

Compound f1-0 (1.4 g, 5 mmole) was dissolved in 30 mL N,N-dimethylformamide, added thereto successively with 2-nitrobenzoyl chloride (1.32 g, 7.12 mmol) and TEA (1.45 ml, 6 mmol) under stirring for 14 hours at room temperature. After completion of reaction, the mixed solution was poured into ice-water (200 mL). Then, the mixture was filtered to collect the precipitate. The precipitate was recrystallized in ethanol to obtain a gray compound f2-1.

Mol. Wt.: 429.4 ($C_{22}H_{11}N_3O_5S$); Rf: 0.8 (ethyl acetate:n-hexane=3:1); Yield: 39%; mp: 280.3° C. (EtOH); IR (KBr) cm$^{-1}$: 1702 (CO), 366 (NH); EI-MS m/z: 384 (M-NO$_2$), 150 (10.62, M); $^1$H-NMR (300 MHz, CDCl$_3$) δ (ppm): 7.63-7.61 (m, 2H, Ar'—$H_{3,4}$), 7.90-7.85 (m, 3H, Ar—$H_{6,7}$, Ar'—$H_4$), 8.39-8.30 (m, 3H, Ar—$H_{5,8}$), 8.46 (d, J=8.4 Hz 1H, Ar'—$H_3$), 8.67 (d, J=8.4 Hz 1H, Ar'—$H_2$), 7.05 (d, J=8.4 Hz 1H, Ar'—$H_5$); $^{13}$C-NMR (75 MHz, CDCl3) δ (ppm): 124.27, 126.11, 127.23, 128.04, 130.42, 131.37, 133.25, 133.78, 134.38, 134.59, 134.80, 135.20 ($C_1N$), 135.93 ($C_2N$), 166.60 (CS), 173.07 (C=O), 181.81 ($C_{10}O$), 184.13 ($C_9O$).

Compound f1-0 (1.4 g, 5 mmole) was dissolved in 30 mL N,N-dimethylformamide, added thereto successively with morpholine-4-carbonyl chloride (1.1 g, 7.12 mmol) and TEA (1.45 ml, 6 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a gray compound f2-2.

Mol. Wt.: 393.41 ($C_{20}H_{15}N_3O_4S$); Rf: 0.8 (ethyl acetate: n-hexane=3:1); Yield: 43%; mp: 240° C. (EtOH); IR (KBr) cm$^{-1}$: 1685 (CO), 3375 (NH); EI-MS m/z: 393 (12.5, M); $^1$H-NMR (300 MHz, CDCl$_3$) δ (ppm): 3.8-3.64 (m, 8H, N—(CH2)$_2$O—(CH2)$_2$), 7.63-7.60 (m, 2H, Ar—$H_{5,8}$), 8.03 (d, J=8.7 Hz, 1H, Ar—$H_4$), 8.23 (d, J=6.9 Hz, 1H, Ar—$H_3$), 8.33 (m, 2H, Ar—$H_{6,7}$), 12.92 (br, 1H, —NH); $^{13}$C-NMR (75 MHz, CDCl$_3$) δ (ppm): 47.24 (CO), 47.64 ((CO), 65.04 (NC), 65.64 (NC), 118.04 ($C_3$), 121.91 ($C_4$), 123.94, 127.04, 127.42, 128.03, 133.54 ($C_8$), 133.74 ($C_5$), 133.94 ($C_7$), 134.06 ($C_6$), 134.34 ($C_1N$), 149.60 ($C_2N$), 157.03 (CS), 168.04 (C=O), 183.19 ($C_{10}O$), 184.55 ($C_9O$).

Example 30

S-6,11-dioxo-6,11-dihydro-1H-anthra[1,2-d]imidazol-2-yl 4-methylpiperazine-1-carbothioate (f2-3)

Compound f1-0 (1.4 g, 5 mmole) was dissolved in 30 mL N,N-dimethylformamide, added thereto successively with 4-methylpiperazine-1-carbonyl chloride (1.42 g, 7.12 mmol) and TEA (1.45 ml, 6 mmol) under stirring for 12 hours at room temperature. After completion of reaction, the mixed solution was poured into ice-water (200 mL). Then, the mixture was filtered to collect the precipitate. The precipitate was recrystallized in ethanol to obtain a gray compound f2-3.

Mol. Wt.: 406.45 ($C_{21}H_{18}N_4O_3S$); Rf: 0.8 (ethyl acetate: n-hexane=3:1); Yield: 46%; Mp: 234° C. (EtOH); IR (KBr) $cm^{-1}$: 1647 (CO), 358 (NH); EI-MS m/z: 406 (17.91, M); $^1$H-NMR (300 MHz, CDCl$_3$) δ (ppm): 2.35 (s, 3H, NCH3-), 2.51 (m, 4H, N(CH2)$_2$-), 3.81-3.64 (br, 4H, (CH2)$_2$-N), 7.80-7.75 (m, 2H, Ar—H$_{5,8}$), 7.99 (d, J=8.4 Hz, 1H, Ar—H$_4$), 8.20 (d, J=8.4 Hz, 1H, Ar—H$_3$), 8.34-8.21 (m, 2H, Ar—H$_{6,7}$); $^{13}$C-NMR (75 MHz, CDCl3) δ (ppm): 40.66 (NC), 47.04 (NC), 47.64 (NC), 56.04 (NC), 56.64 (NC), 118.04 (C$_3$), 121.94 (C$_4$), 123.94, 127.04, 127.46, 128.03 (C$_8$), 133.54 (C$_5$), 133.70 (C$_7$), 133.90 (C$_6$), 134.34 (C$_1$N), 149.60 (C$_2$N), 157.03 (C S), 168.04 (C=O), 183.19 (C$_{10}$O), 184.50 (C$_9$O).

Example 31

S-6,11-dioxo-6,11-dihydro-1H-anthra[1,2-d]imidazol-2-yl 3-phenylpropanethioate (f2-4)

Compound f1-0 (1.4 g, 5 mmole) was dissolved in 30 mL N,N-dimethylformamide, added thereto successively with 3-phenylpropanoyl chloride (1.21 g, 7.16 mmol) and TEA (1.45 ml, 6 mmol) under stirring for 11 hours at room temperature. After completion of reaction, the mixed solution was poured into ice-water (200 mL). Then, the mixture was filtered to collect the precipitate. The precipitate was recrystallized in ethanol to obtain a gray compound f2-4.

Mol. Wt.: 412.46 ($C_{24}H_{16}N_2O_3S$); Rf: 0.8 (ethyl acetate: n-hexane=3:1); Yield: 41%; mp: 238° C. (EtOH); IR (KBr) $cm^{-1}$: 1659 (CO), 2920 (NH); EI-MS m/z: 412 (0.5, M); $^1$H-NMR (300 MHz, CDCl$_3$) δ (ppm): 3.18 (t, J=7.5, 7.8 Hz 2H, COCH2-), 2.97 (t, J=7.2, 7.8 Hz 4H, SCH2-), 7.31 (d, J=4.5 5H, Ar'—H$_{3,4,5,6}$), 7.85-7.83 (m, 2H, Ar—H$_{5,8}$), 8.17 (d, J=8.4 Hz, 1H, Ar—H$_4$), 8.4 (d, J=8.4 Hz, 1H, Ar—H$_3$), 8.34-8.27 (m, 2H, Ar—H$_{6,7}$); $^{13}$C-NMR (75 MHz, CDCl$_3$) δ (ppm): 30.81 (C-Ph), 44.96 (C=OC), 124.27, 126.19, 127.19, 128.04, 130.49, 131.74, 133.25, 133.79, 134.38, 134.59, 134.88, 135.20, 135.93 (C$_1$N), 150.60 (C$_2$N), 156.67 (CS), 181.81 (C=O), 184.13 (C$_{10}$O), 189.93 (C$_9$O).

Example 32

S-6,11-dioxo-6,11-dihydro-1H-anthra[1,2-d]imidazol-2-yl 2,5-bis(trifluoromethyl)benzothioate (f2-5)

Example 33

S-6,11-dioxo-6,11-dihydro-1H-anthra[1,2-d]imidazol-2-yl 2,5-dimethylfuran-3-carbothioate (f2-6)

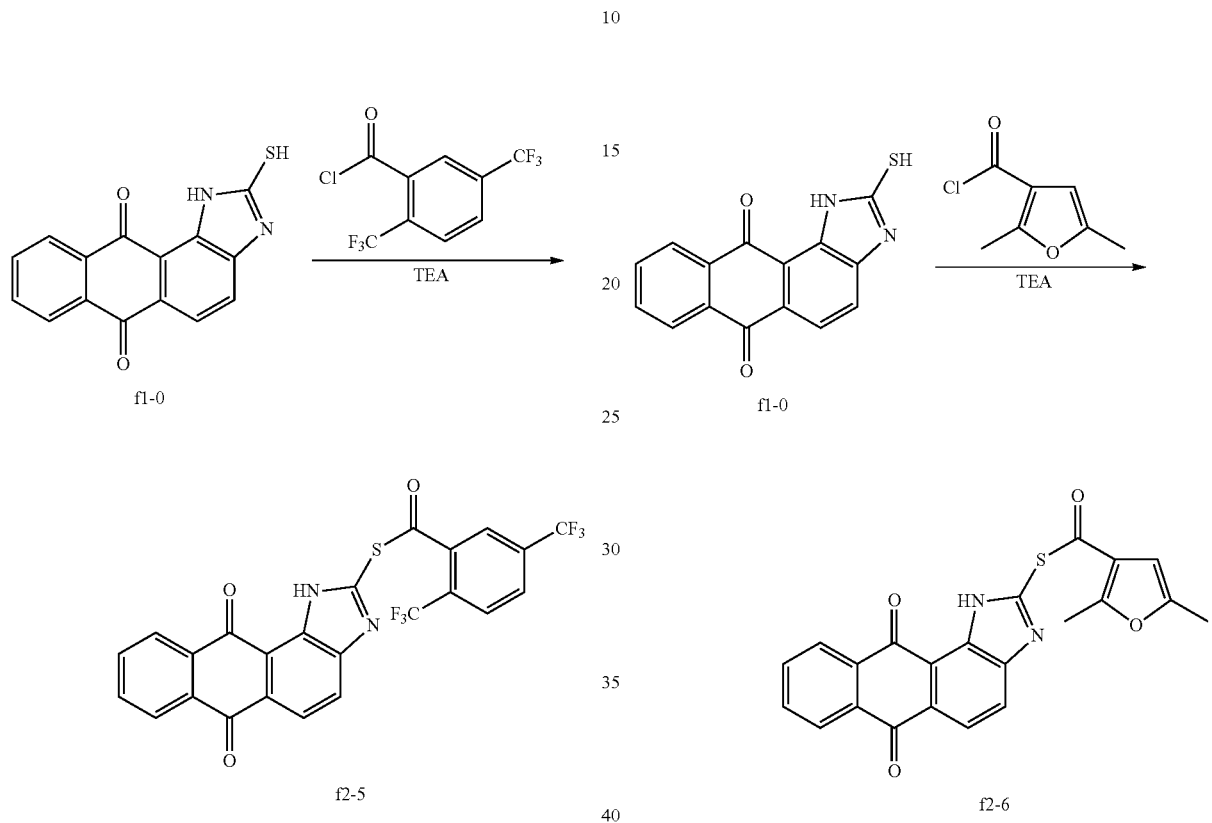

Compound f1-0 (1.4 g, 5 mmole) was dissolved in 30 mL N,N-dimethylformamide, added thereto successively with 2,5-bis(trifluoromethyl)benzoyl chloride (1.94 g, 7.0 mmol) and TEA (1.45 ml, 6 mmol) under stirring for 13 hours at room temperature. After completion of reaction, the mixed solution was poured into ice-water (200 mL). Then, the mixture was filtered to collect the precipitate. The precipitate was separated by column chromatography with eluent (ethyl acetate:dichloromethane=1:3) to obtain a compound f2-5.

Mol. Wt.: 520.40 ($C_{24}H_{10}N_2O_3F_2S$); Rf: 0.8 (ethyl acetate: n-hexane=3:1); Yield: 30%; mp: 345° C. (EtOH); IR (KBr) cm$^{-1}$: 1731 (CO), 3356 (NH); EI-MS m/z: 520 (23.42, M); $^1$H-NMR (300 MHz, CDCl$_3$) δ (ppm): 7.81 (s, 1H, Ar'—H$_2$), 7.86-7.84 (m, 2H, Ar'—H$_{4,5}$), 7.93 (s, 2H, Ar—H$_{5,8}$), 8.27 (d, J=8.4 Hz 1H, Ar'—H$_3$), 8.51 (d, J=8.4 Hz 1H, Ar'—H$_2$), 8.37-8.31 (m, 2H, Ar'—H$_{6,7}$), 11.07 ((br, 1H, —NH); $^{13}$C-NMR (75 MHz, CDCl3) δ (ppm): 114.87, 119.95, 124.27, 126.10, 127.23, 128.04, 130.42, 131.74, 133.25, 133.79, 134.38, 134.59, 134.80, 135.20 (C$_1$N), 135.98 (C$_2$N), 166.60 (CS), 173.07 (C=O), 181.81 (C$_{10}$O), 184.13 (C$_9$O).

Compound f1-0 (1.4 g, 5 mmole) was dissolved in 30 mL N,N-dimethylformamide, added thereto successively with 2,5-dimethylfuran-3-carbonyl chloride (1.11 g, 7.0 mmol) and TEA (1.45 ml, 6 mmol) under stirring for 9 hours at room temperature. After completion of reaction, the mixed solution was poured into ice-water (200 mL). Then, the mixture was filtered to collect the precipitate. The precipitate was separated by column chromatography with eluent (ethyl acetate: dichloromethane=1:3) to obtain a compound f2-6.

Mol. Wt.: 402.42 ($C_{22}H_{14}N_2O_4S$); Rf: 0.8 (ethyl acetate: n-hexane=3:1); Yield: 29%; mp: >400° C. (EtOH); IR (KBr) cm$^{-1}$: 1654 (CO), 3354 (NH); EI-MS m/z: 402 (18.67, M); $^1$H-NMR (300 MHz, CDCl$_3$) δ (ppm): 2.32 (s, 2H, CH$_3$—), 2.67 (s, 2H, CH$_3$—) 6.37 (s, 2H, Ar'$_2$H), 7.83-7.80 (m, 2H, Ar—H$_{4,5}$), 8.06 (d, J=8.4 Hz 1H, Ar—H$_3$), 8.25 (d, J=8.4 Hz 1H, Ar—H$_2$), 8.36-8.34 (m, 2H, Ar—H$_{6,7}$), 12.84 ((br, 1H, —NH); $^{13}$C-NMR (75 MHz, CDCl$_3$) δ (ppm): 10.81 (C—Ar), 13.96 (C—Ar), 104.87, 119.95, 124.27, 126.19, 127.23, 128.04, 130.49, 131.37, 133.25, 133.79, 134.38, 134.59, 134.80, 135.20 (C$_1$N), 135.93 (C$_2$N), 150.60, 156.67, (CS), 181.81 (C=O), 184.13 (C$_{10}$O), 184.13 (C$_9$O).

Example 34

S-6,11-dioxo-6,11-dihydro-1H-anthra[1,2-d]imidazol-2-yl pyrrolidine-1-carbothioate (f2-7)

Example 35

S-6,11-dioxo-6,11-dihydro-1H-anthra[1,2-d]imidazol-2-yl piperidine-1-carbothioate (f2-8)

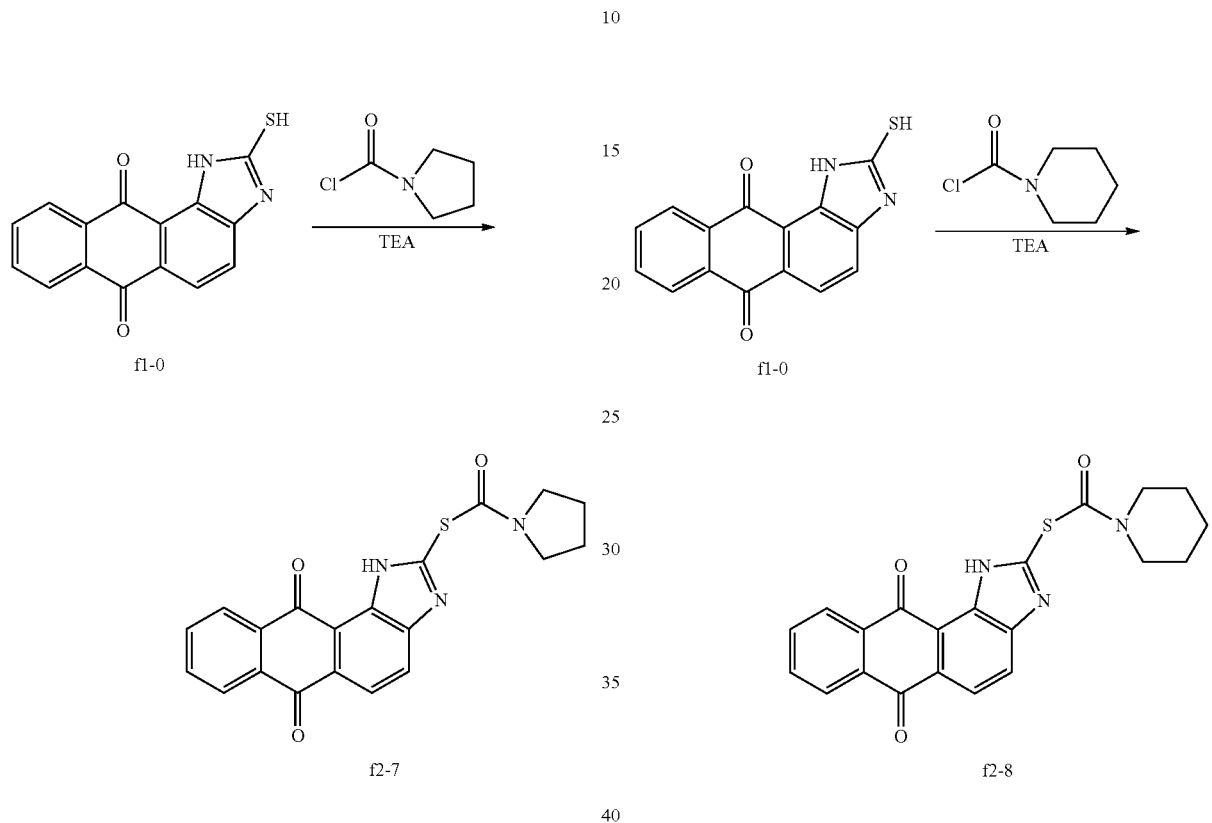

Compound f1-0 (1.4 g, 5 mmole) was dissolved in 30 mL N,N-dimethylformamide, added thereto successively with pyrrolidine-1-carbonyl chloride (0.94 g, 7.0 mmol) and TEA (1.45 ml, 6 mmol) under stirring for 11 hours at room temperature. After completion of reaction, the mixed solution was poured into ice-water (200 mL). Then, the mixture was filtered to collect the precipitate. The precipitate was recrystallized in ethanol to obtain a brown compound f2-7.

Mol. Wt.: 377.42 ($C_{20}H_{15}N_3O_3S$); Rf: 0.8 (ethyl acetate: n-hexane=3:1); Yield: 52%; mp: 229° C. (EtOH); IR (KBr) $cm^{-1}$: 1651 (CO), 3308 (NH); EI-MS m/z: 377 (46.79, M); $^1$H-NMR (300 MHz, $CDCl_3$) δ (ppm): 1.71 (s, 4H, $CH_2$—$CH_2$), 3.72-3.55 (m, 4H, N—$CH_2$—$CH_2$), 6.37 (s, 2H, $Ar'_2$H), 7.79-7.76 (m, 2H, Ar—$H_{5,8}$), 7.98 (d, J=8.4 Hz 1H, Ar—$H_3$), 8.18 (d, J=8.4 Hz 1H, Ar—$H_4$), 8.32-8.27 (m, 2H, Ar'—$H_{6,7}$), 12.91 ((br, 1H, —NH); $^{13}$C-NMR (75 MHz, CDCl3) δ (ppm): 24.45 (NCC), 26.34 (NCC), 47.04 (NC), 47.64 (NC), 118.00 ($C_3$), 121.91 ($C_4$), 123.98, 127.11, 127.58, 128.03, 133.53 ($C_8$), 133.74 ($C_5$), 133.90 ($C_2$), 134.16 ($C_6$), 134.35 ($C_1$N), 149.61 ($C_2$N), 157.03 (CS), 167.30 (C=O), 183.91 ($C_{10}$O), 184.55 ($C_9$O).

Compound f1-0 (1.4 g, 5 mmole) was dissolved in 30 mL N,N-dimethylformamide, added thereto successively with piperidine-1-carbonyl chloride (1.03 g, 7.0 mmol) and TEA (1.45 ml, 6 mmol) under stirring for 11 hours at room temperature. After completion of reaction, the mixed solution was poured into ice-water (200 mL). Then, the mixture was filtered to collect the precipitate. The precipitate was recrystallized in ethanol to obtain a brown compound f2-8.

Mol. Wt.: 391.44 ($C_{21}H_{17}N_3O_3S$); Rf: 0.8 (ethyl acetate: n-hexane=3:1); Yield: 53%; mp: 243° C. (EtOH); IR (KBr) $cm^{-1}$: 1647 (CO); EI-MS m/z: 391 (18.06, M); $^1$H-NMR (300 MHz, $CDCl_3$) δ (ppm): 1.61 (s, 4H, $CH_2$—), 2.11-1.99 (m, 4H, $CH_2$—$CH_2$), 3.55 (t, J=6.3, 6.6 Hz 2H, $NCH_2$—), 3.73-3.69 (t, J=6.6 Hz 2H, $NCH_2$—), 7.80-7.78 (m, 2H, Ar—$H_{5,8}$), 7.99 (d, J=8.1 Hz 1H, Ar—$H_3$), 8.20 (d, J=8.4 Hz 1H, Ar—$H_4$), 8.31 (m, 2H, Ar'—$H_{6,2}$), 13.16 ((br, 1H, —NH); $^{13}$C-NMR (75 MHz, CDCl3) δ (ppm): 24.73 (NCC), 25.84 (NCC), 48.3 (NC), 53.29 (NC), 118.18, 121.97 ($C_8$), 126.93 ($C_5$), 127.69 ($C_2$), 128.48 ($C_6$), 133.63 ($C_1$N), 134.07, 134.15 ($C_6$), 133.42 ($C_2$N), 153.76 (CS), 167.60 (C=O), 180.64 ($C_{10}$O), 183.146 ($C_9$O).

Example 36

S-6,11-dioxo-6,11-dihydro-1H-anthra[1,2-d]imidazol-2-yl diethylcarbamothioate (f2-9)

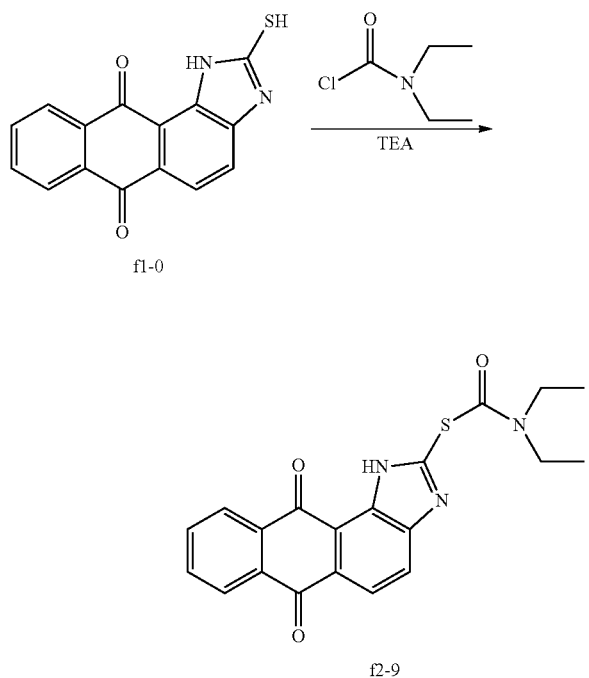

Compound f1-0 (1.4 g, 5 mmole) was dissolved in 30 mL N,N-dimethylformamide, added thereto successively with diethylcarbamic chloride (1.03 g, 7.0 mmol) and TEA (1.45 ml, 6 mmol) under stirring for 11 hours at room temperature. After completion of reaction, the mixed solution was poured into ice-water (200 mL). Then, the mixture was filtered to collect the precipitate. The precipitate was recrystallized in ethanol to obtain a brown compound f2-9.

Mol. Wt.: 379.09 ($C_{20}H_{17}N_3O_3S$); Rf: 0.8 (ethyl acetate: n-hexane=3:1); Yield: 53%; mp: 215° C. (EtOH); IR (KBr) cm$^{-1}$: 1644 (CO); EI-MS m/z: 379 (M); $^1$H-NMR (300 MHz, CDCl$_3$) δ (ppm): 1.27 (t, J=6.9, 7.2 Hz 3H, CH$_3$—), 1.34 (t, J=6.9, 7.2 Hz 3H, CH$_3$—), 3.52-3.45 (m, 2H, NCH$_2$—), 3.59-3.55 (m, 2H, NCH$_2$—), 7.82-7.55 (m, 2H, Ar—H$_{5,8}$), 7.99 (d, J=8.1 Hz 1H, Ar—H$_3$), 8.19 (d, J=8.4 Hz 1H, Ar—H$_4$), 8.33-8.29 (m, 2H, Ar'—H$_{6,7}$), 12.99 ((br, 1H, —NH); $^{13}$C-NMR (75 MHz, CDCl3) δ (ppm): 13.34 (NCC), 14.06 (NCC), 43.26 (NC), 118.09 (C$_3$), 121.85 (C$_4$), 123.62, 126.87, 127.66, 128.41, 132.21 (C$_8$), 133.58 (C$_5$), 134.05 (C$_7$), 134.12 (C$_6$), 134.41 (C$_1$N), 148.13 (C$_2$N), 152.11 (CS), 162.11 (C═O), 183.08 (C$_{10}$O), 184.48 (C$_9$O).

Example 37

2-(2-N-ethylthio)-1H-anthra[1,2-d]imidazole-6,11-dione (f3-1)

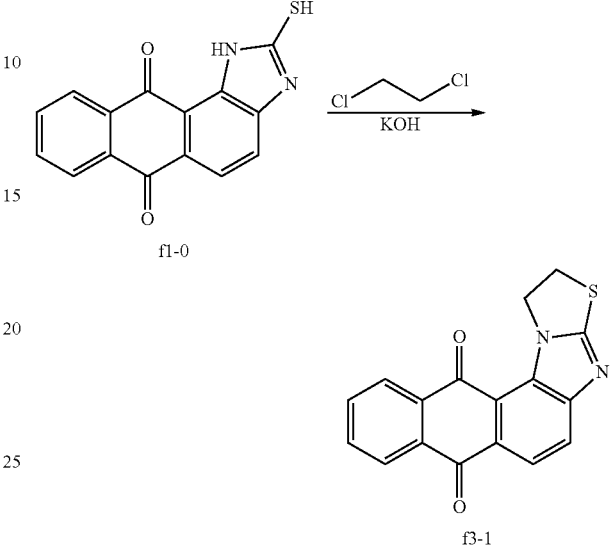

Compound f1-0 (1.4 g, 5 mmole) was dissolved in 30 mL N,N-dimethylformamide, added thereto successively with 1,2-dichloroethane (0.74 g, 7.5 mmol) and KOH (1 equive, 10 mmol) under stirring for 10 hours at room temperature. After completion of reaction, the mixed solution was poured into ice-water (200 mL). Then, the mixture was filtered to collect the precipitate. The precipitate was recrystallized in ethanol to obtain a brown compound f3-1.

Mol. Wt.: 306.34 (C17H10N2O2S); Rf: 0.6 (ethyl acetate: dichloromethane=1:6); Yield: 39%; mp: 242° C. (EtOH); IR (KBr) cm$^{-1}$: 1630 (CO), 3432 (NH); EI-MSm/z: 306 (16.05, M), 307 (100, M+1), 308 (25.53, M+2), 305 (24.38, M−1), 280 (2.08); HRMS (ESI-TOF) m/z: calcd for C17H10N2O2 [M]: 306.0464, (100, M);
$^1$H-NMR (300 MHz, CDCl3) δ (ppm): 3.95 (t, J=7.5, 7.2 Hz, 2H, S—CH$_2$—), 5.19 (t, J=7.5, 6.9 Hz, 2H, N—CH$_2$—), 7.77 (m, 2H, Ar—H$_{6,7}$), 8.2 (d, J=8.1 Hz, 1H, Ar—H$_4$), 8.19 (d, J=8.1 Hz, 1H, Ar—H$_3$), 8.27 (m, 2H, Ar—H$_{5,8}$); $^{13}$C-NMR (75 MHz, CDCl3) δ (ppm): 34.21 (SC), 50.86 (NC), 107.96 (C$_3$), 118.84 (C$_4$), 122.55, 124.40, 126.91, 127.25, 128.53 (C$_8$), 133.45 (C$_5$), 133.99 (C$_7$), 134.24 (C$_6$), 155.67 (C$_1$N), 165.96 (C$_2$N), 166.67 (CS), 183.11 (C$_{10}$O), 184.06 (C$_9$O).

Example 38

Figure 2A:
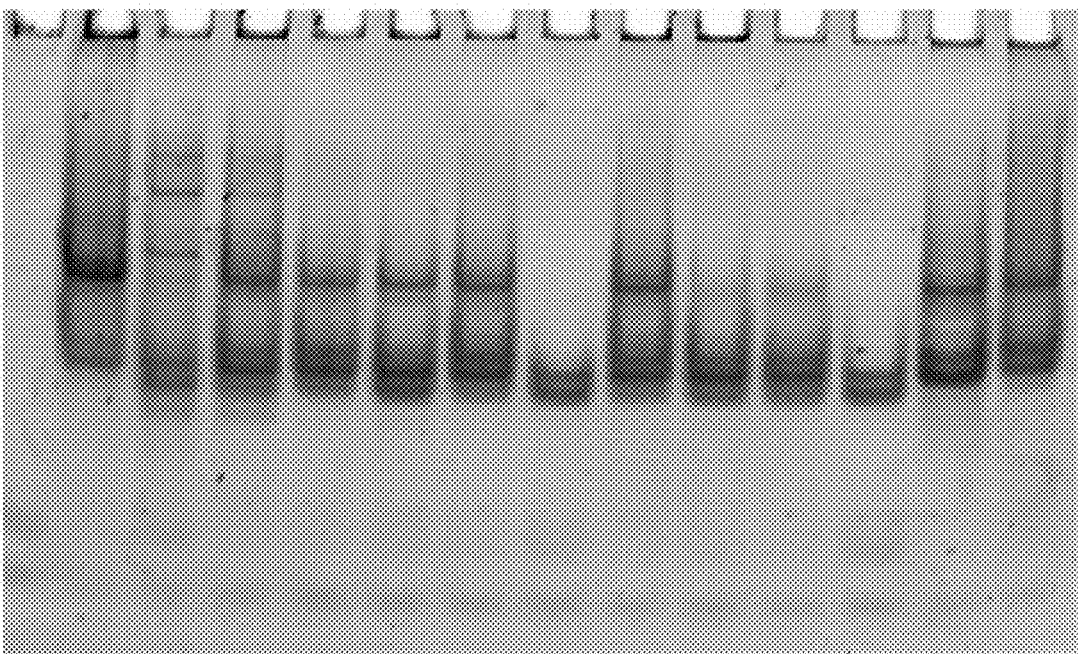
FIG. 2A depicts the result of the compound f1-0 to f1-11 in TRAP assay.
Figure 2B:
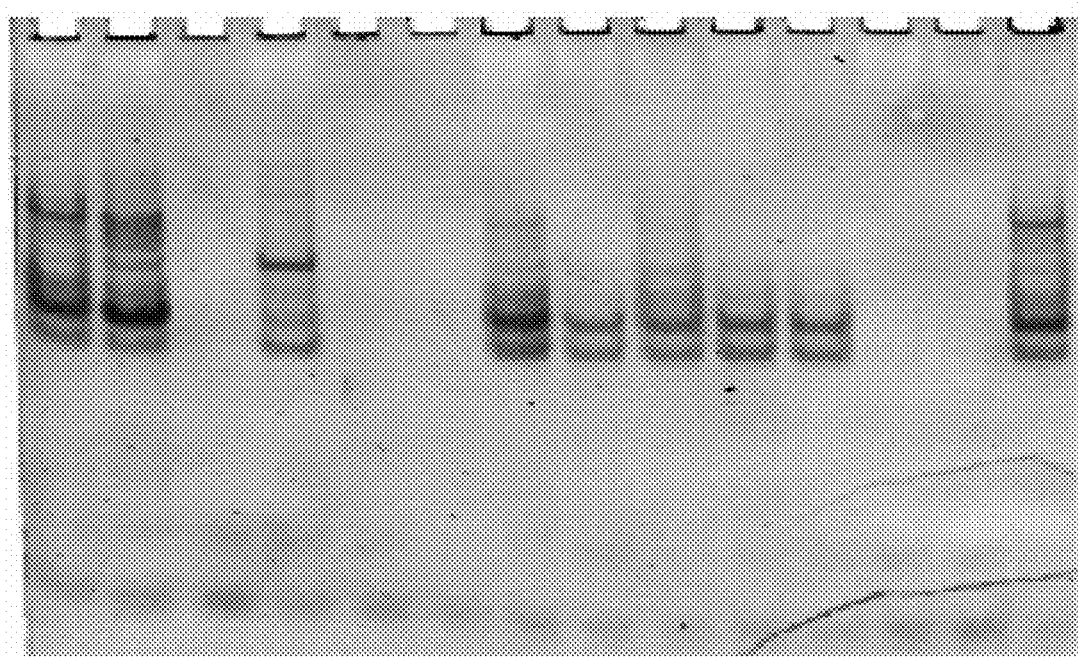
FIG. 2B depicts the result of the compound f1-12 to f1-23 in TRAP assay.
Figure 2C:
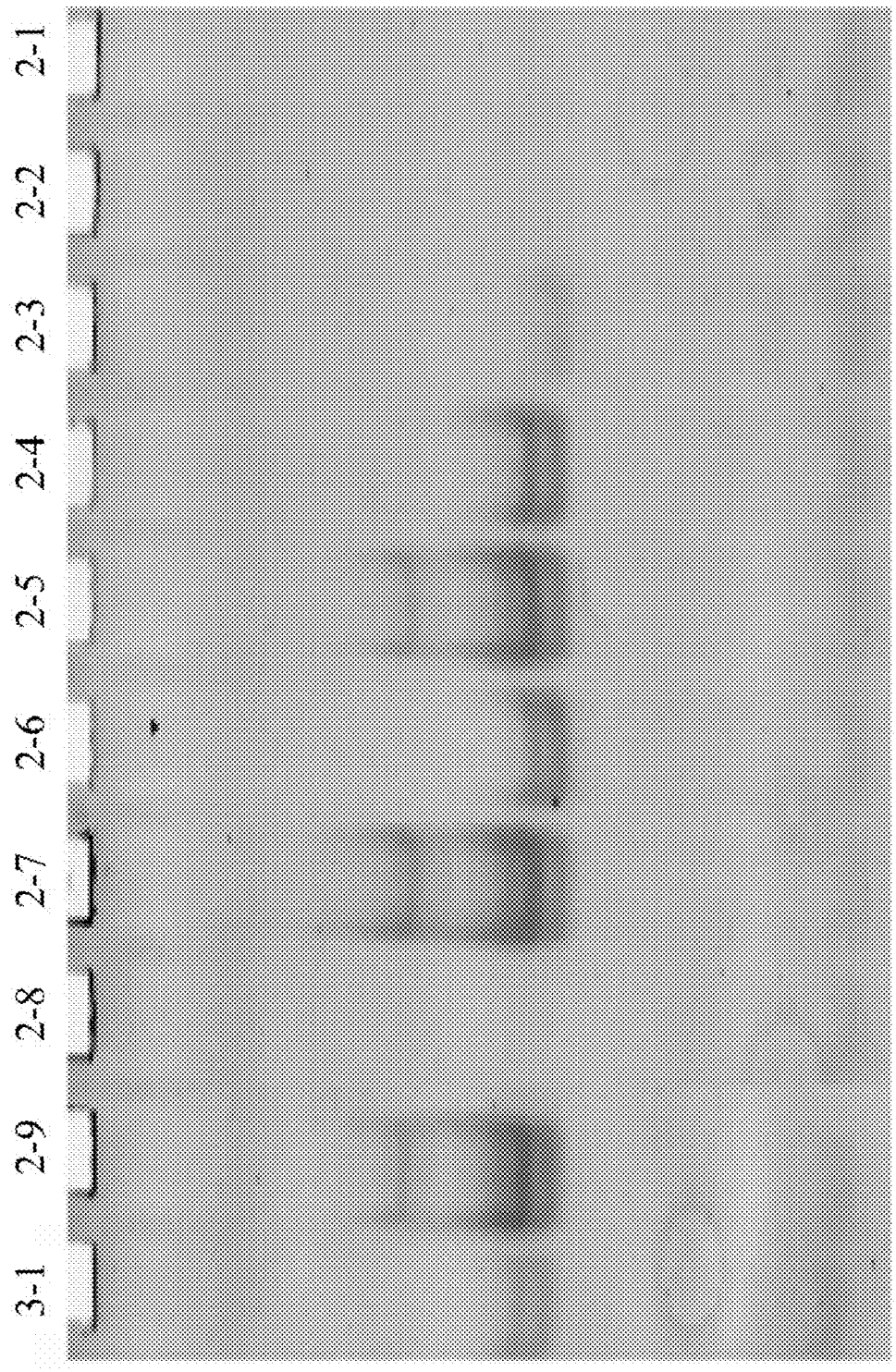
FIG. 2C depicts the result of the compound f2-1 to f2-9 and f3-1 in TRAP assay. P represents positive control, N represents negative control.
Figure 3A:
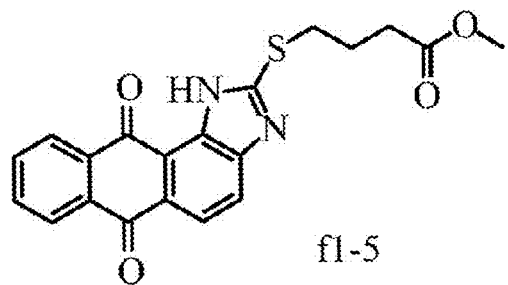
FIG. 3A to FIG. 3B depict the structure of the compounds possess the inhibition effect of telomerease in TRAP assay.
Figure 3A:
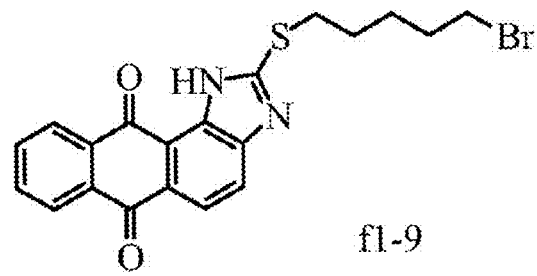
Figure 3A:
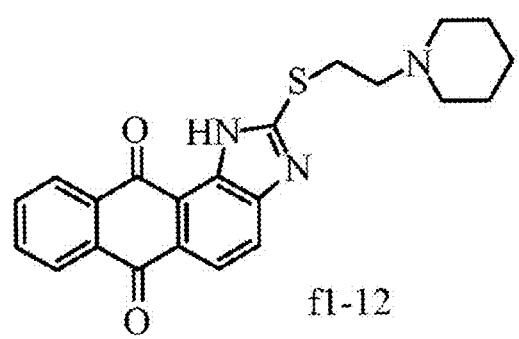
Figure 3A:
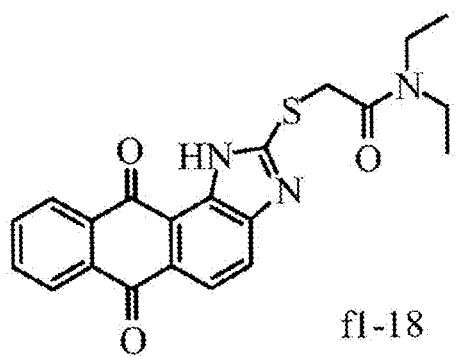
Figure 3A:
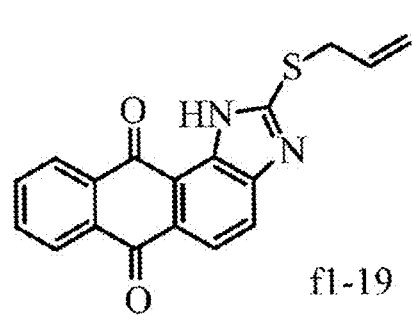
Figure 3A:
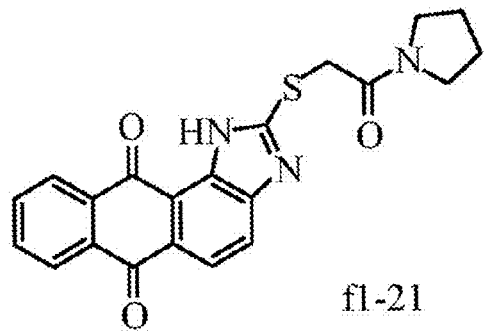
Figure 3B:
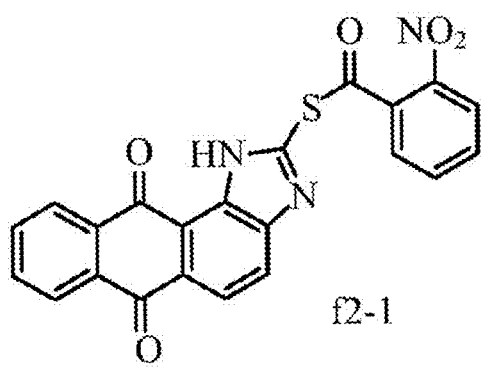
Figure 3B:
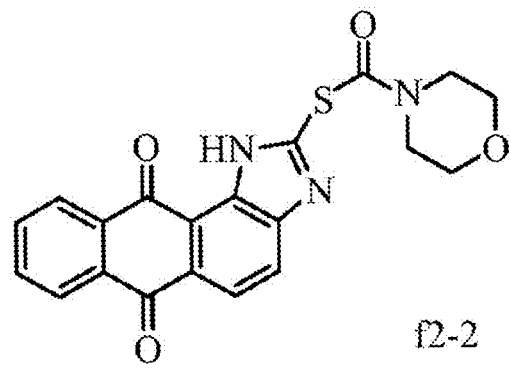
Figure 3B:
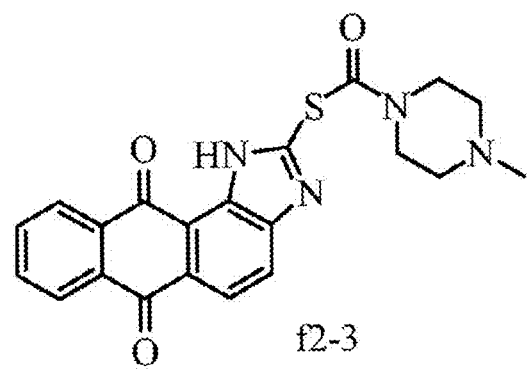
Figure 3B:
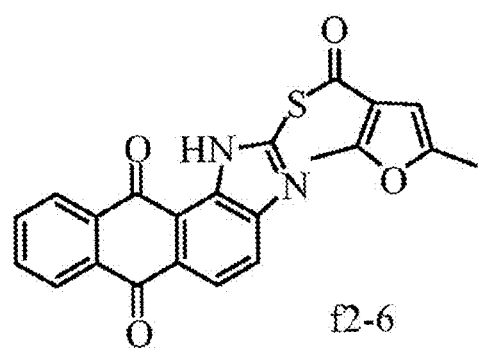
Figure 3B:
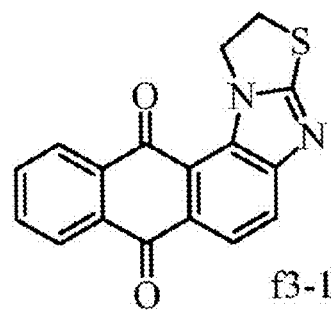

Result of Screening Telomerase Inhibitor by Telomere Repeat Amplification Protocol (TRAP) Assay In the TRAP assay, if a compound can stabilize the G-quadruplex structure such that telomerase can not act on telomere, then the effect of inhibiting the telomerase can be achieved. In the FIG. 2A to FIG. 2C, DMSO treatment represents as the positive control group (P); while a negative control group (N) used 5 μl of 0.1 mg/ml RNase A (CLONTECH) in the assay. It could be observed that a number of telomeric fragments were detected in the positive control group (P), while none was detected in the negative control group (N). 10 μM was selected as the concentration used to screen compounds. Results also shown in FIG. 3A to FIG. 3C indicated that 11 compounds f1-5, f1-9, f1-12, f1-18, f1-19, f1-21, f2-1, f2-2, f2-3, f2-6, and f3-1 exhibited inhibition effect against telomerase.

Example 39

Results of MTT Assay

Figure 4A:
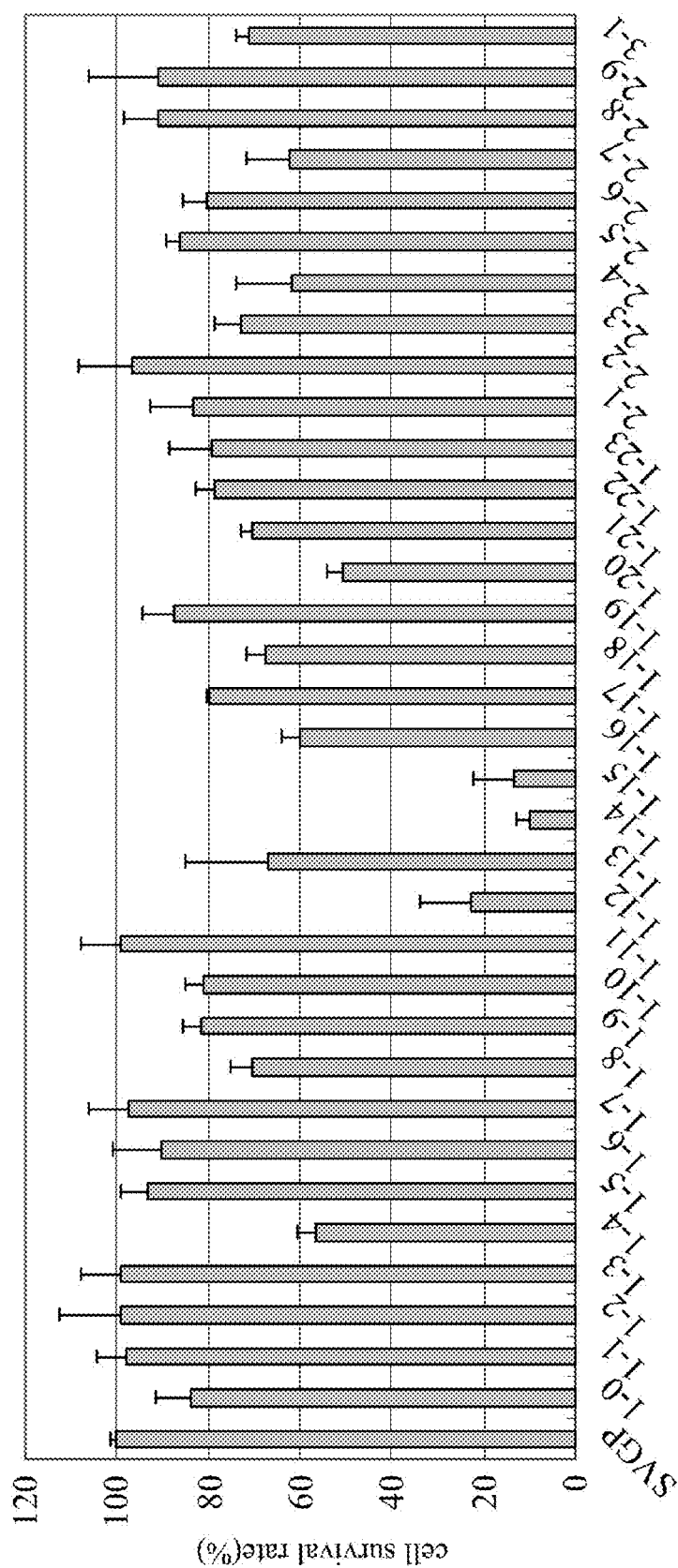
FIG. 4A depicts the cell survival rate of the compounds of the invention by SVGP p12 cell screening system.
Figure 4B:
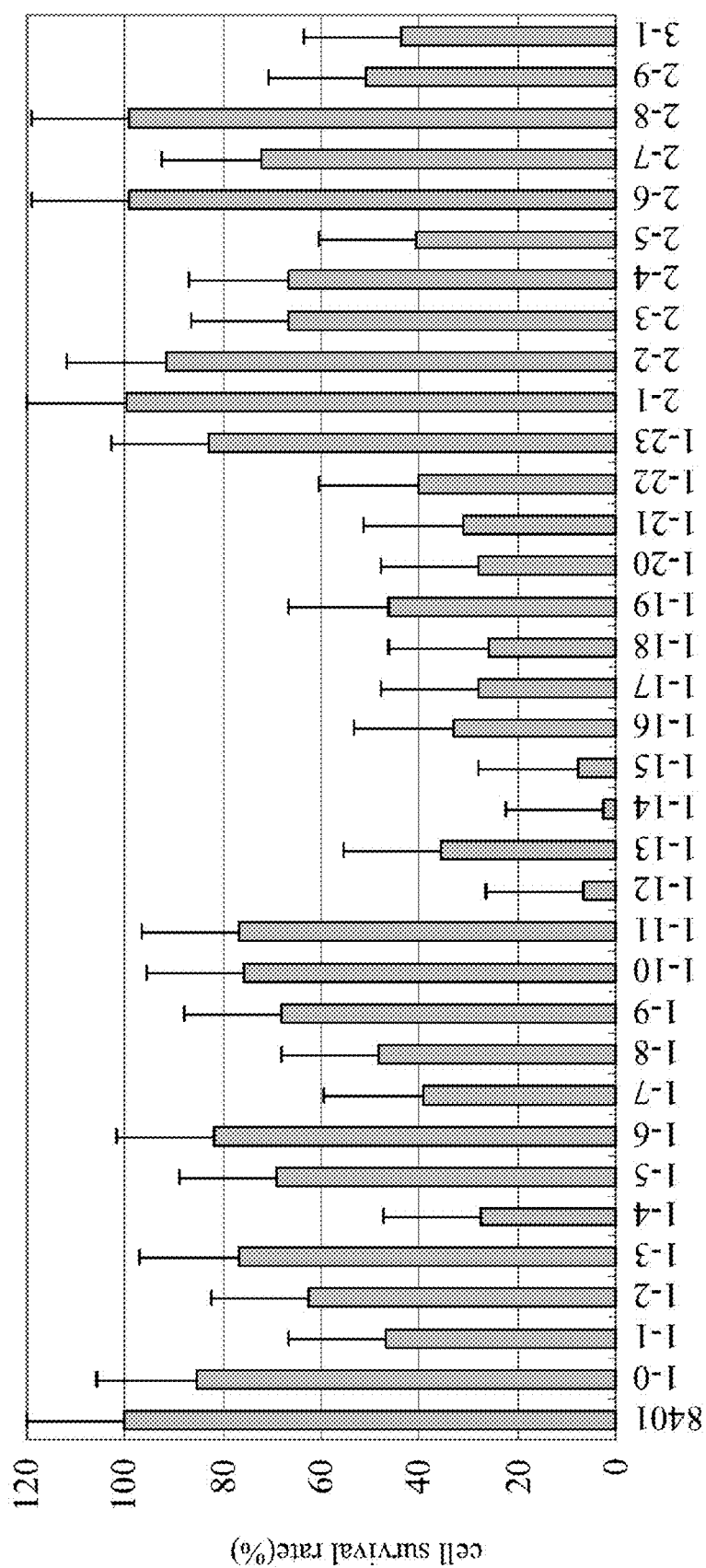
FIG. 4B depicts the cell survival rate of the compounds of the invention by GBM 8401 cell screening system.
Figure 4C:
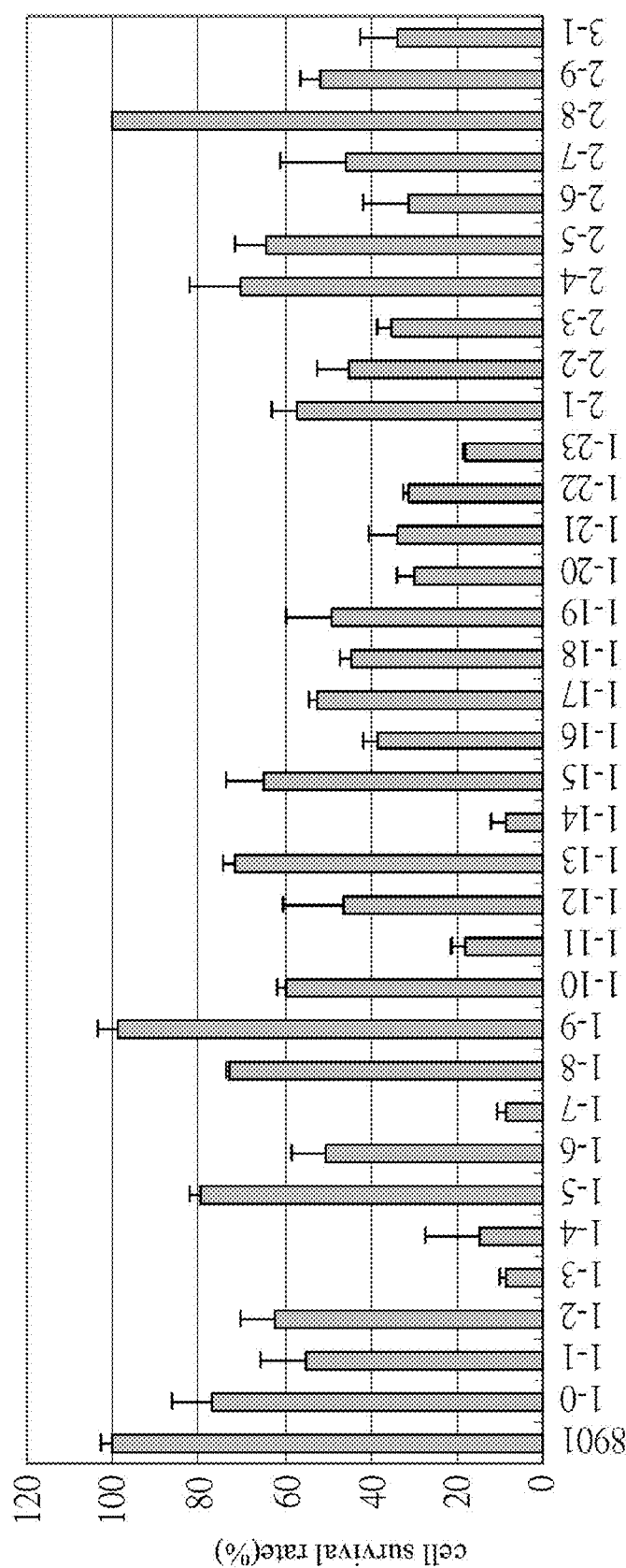
FIG. 4C depicts the cell survival rate of the compounds of the invention by GBM 8901 cell screening system. The X axis represents the code of compounds for treatment; "SVGP", "8401" and "8901" represents the control group.

Three cell lines, SVGP p12 (nomal cell), GBM8401 (tumor cell), and GBM8901 (tumor cell), were used to evalute the cell toxicity of each compound. Cell without compound treatment was used as the control group, while cell treated with compound was used as the test group. By comparing these two groups, the result of cell survival rate in MTT assay could be used to evaluate the cell toxicity of each compound (FIG. 4A to 4C).

39-1. The Compounds have the Inhibition Effect on the Growth of Tumor Cells GBM8401 or GBM8901 (Survival Rate Less than 80%):

27 Compounds f1-1 to f1-5, f1-7 to f1-22, f2-3 to f2-5, f2-7, f2-9 and f3-1 exhibited inhibitory effect against tumor cell GBM8401; 27 compounds f1-0 to f1-4, f1-6 to f1-8, f1-10 to f1-23, f2-1 to f2-7, f2-9 and f3-1 exhibited inhibitory effect against tumor cell GBM8901.

39-2. The Compounds without Cell Toxicity for Normal Cell SVGP p12 (Survival Rate Higher than 80%):

Compounds f1-0 to f1-3, f1-5 to f1-7, f1-9 to f1-11, f1-17, f1-19, f1-22 to f1-23, f2-1 to f2-2, f2-5 to f2-6, and f2-8 to f2-9 without cell toxicity for normal cell SVGP p12.

Figure 5A:
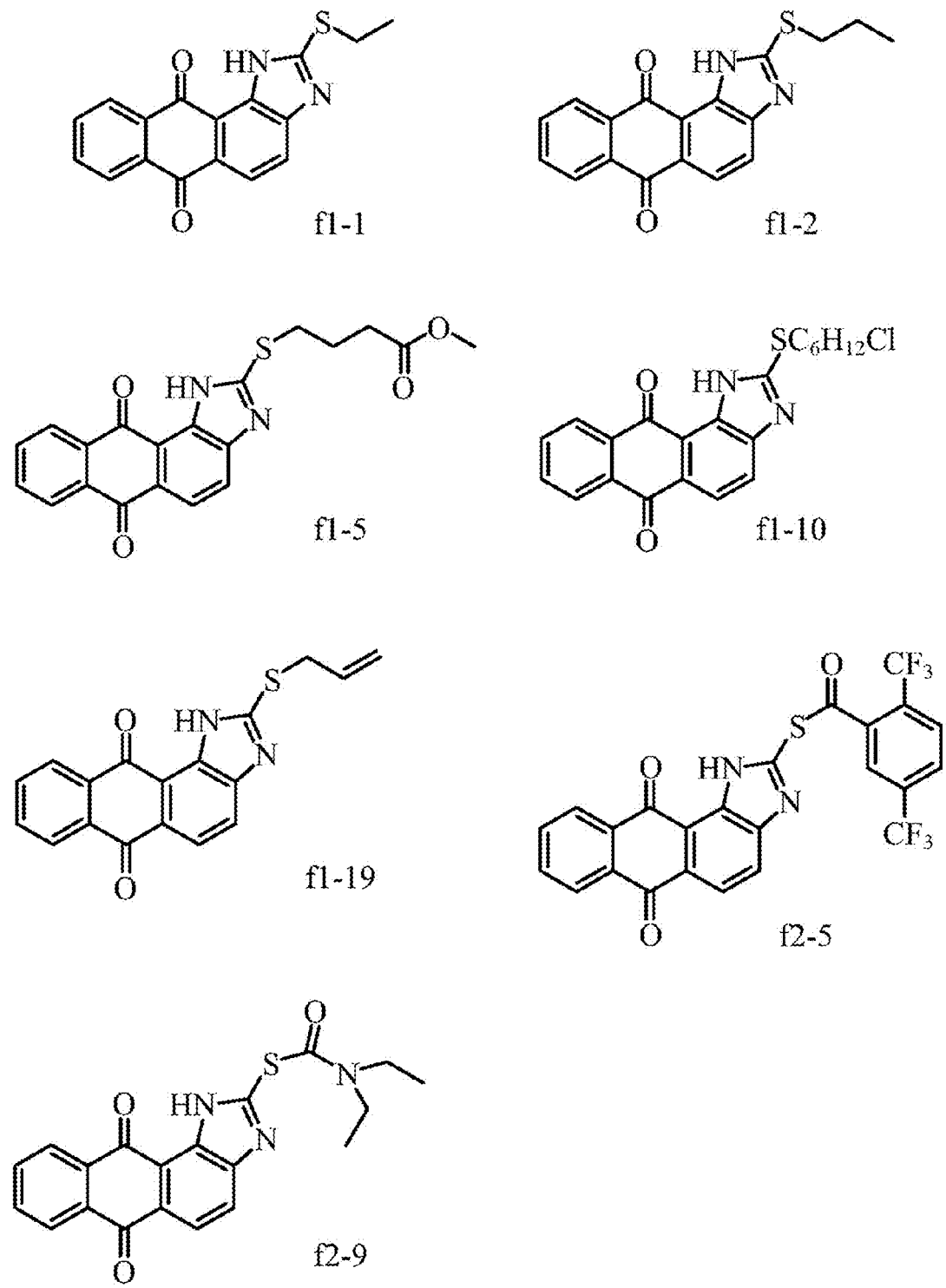
FIG. 5A depicts the compounds possess the inhibition effect of cancer cell (tumor cell) GBM8401 and GBM8901 in MTT assay.

39-3. The Compounds with a Survival Rate Higher than 80% for Normal Cell SVG p12, and can also Inhibit the Growth of Both Tumor Cells GBM8401 and GBM8901 (Survival Rate Less than 80%):

There were 7 Compounds f1-1, f1-2, f1-5, f1-10, f1-19, f2-5, and f2-9 in this category (FIG. 5A).

Figure 5B:
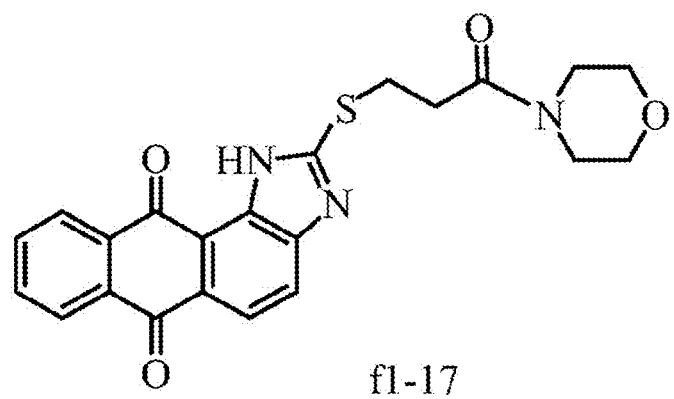
FIG. 5B depicts the compounds possess the inhibition effect of cancer cell GBM8401 in MTT assay.
Figure 5B:
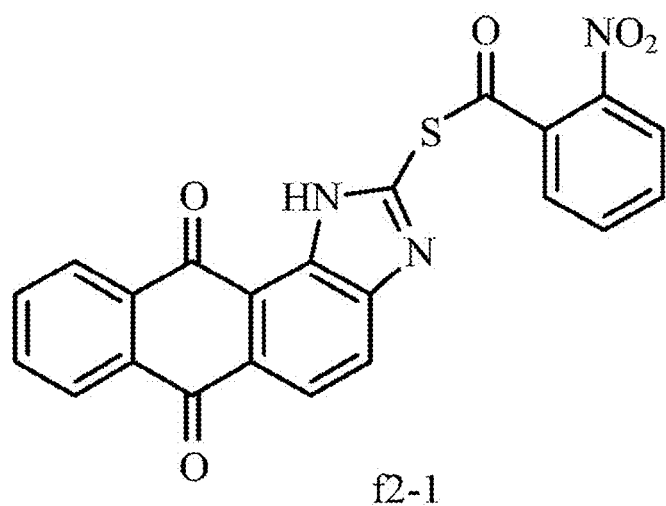
Figure 5B:
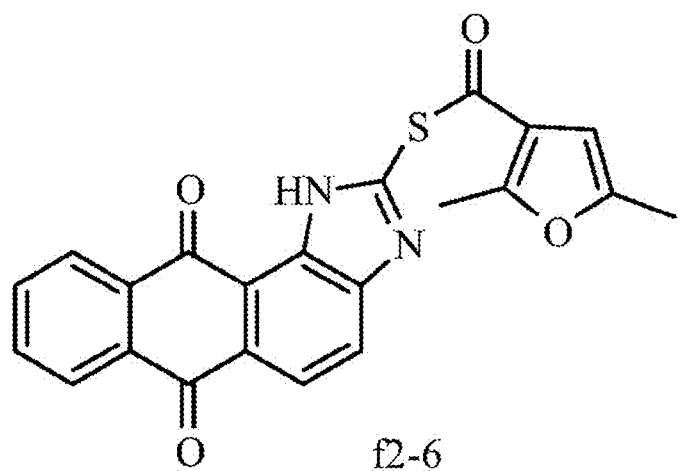

39-4. The Compounds with a Survival Rate Higher than 80% for Normal Cell SVG p12, and can Only Inhibit the Growth of Tumor Cell GBM8401 (Survival Rate Less than 80%):

There were 3 compounds f1-17, f2-1 and f2-6 in this category (FIG. 5B).

Figure 5C:
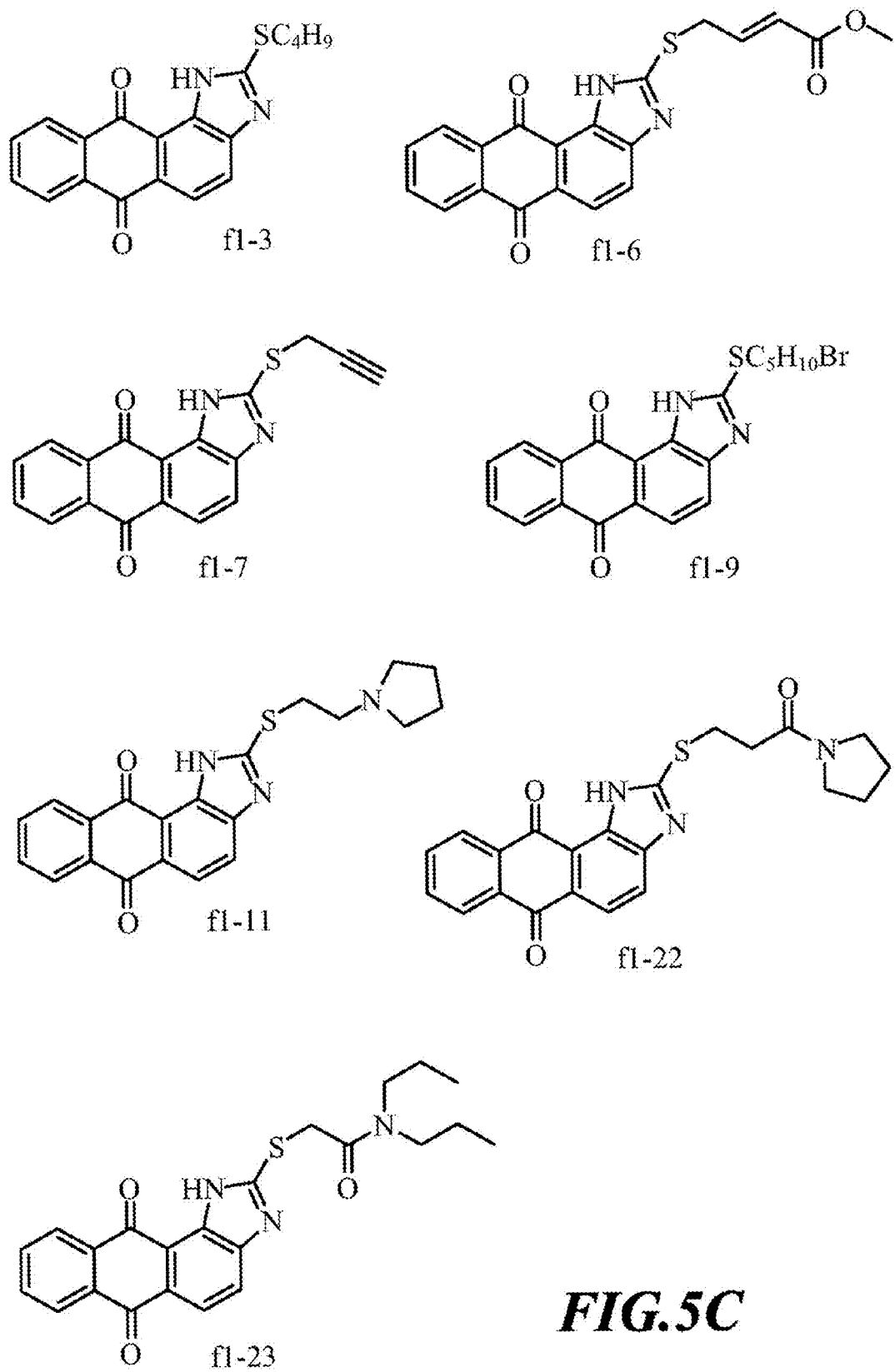
FIG. 5C depicts the compounds possess the inhibition effect of cancer cell GBM8901 in MTT assay.

39-5. The Compounds with a Survival Rate Higher than 80% for Normal Cell SVG p12, and can Only Inhibit the Growth of Tumor Cell GBM8901 (Survival Rate Less than 80%):

There were 7 compounds f1-3, f1-6, f1-7, f1-9, f1-11, f1-22 and f1-23 in this category (FIG. 5C).

39-6. The Compounds with a Survival Rate about 80% for Normal Cell SVG p12, and can Promote the Rapid Proliferation (or Growth) of Tumor Cell GBM8901 (Survival Rate Higher than 98%).

Figure 5D:
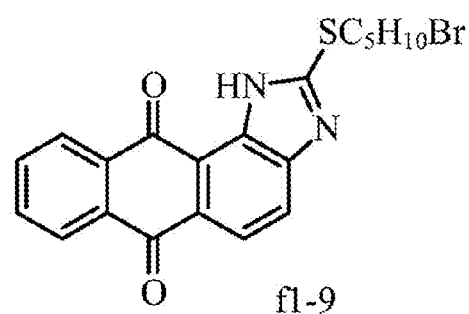
FIG. 5D depicts the compound f1-9 allowes normal cell SVG p12 for a survival rate of about 80%, and rapid proliferation (growth) of cancer cell GBM8901 up to a survival rate of higher than 98% in MTT assay.

There was one compound f1-9 in this category, which indicated that said compound could allow rapid growth, maturation, and then apoptosis of said tumor cell without cell toxcity on normal cell (FIG. 5D).

39-7. The Compounds with a Survival Rate about 80% for Normal Cell SVG p12, and can Promote the Rapid Proliferation (or Growth) of Tumor Cell GBM8401 (Survival Rate Higher than 98%).

Figure 5E:
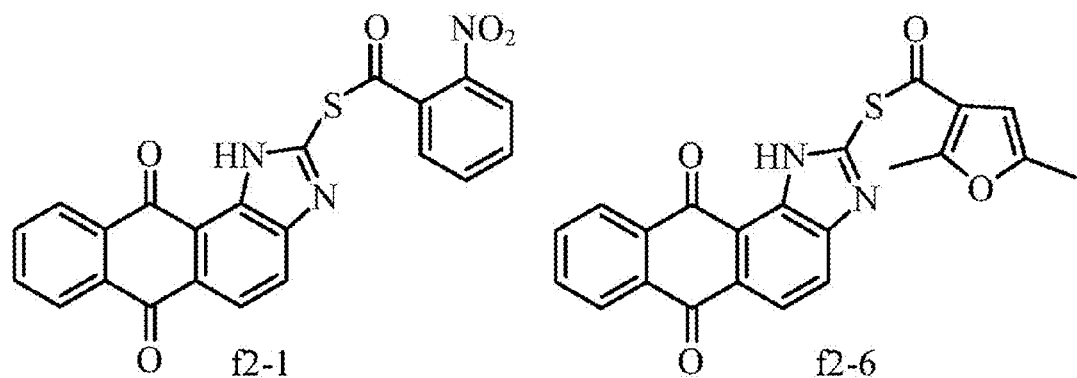
FIG. 5E depicts the compounds f2-1 and f2-6 allow normal cell SVG p12 for a survival rate of about 80%, and rapid proliferation (growth) of cancer cell GBM8401 up to a survival rate of higher than 98% in MTT assay.
Figure 6A:
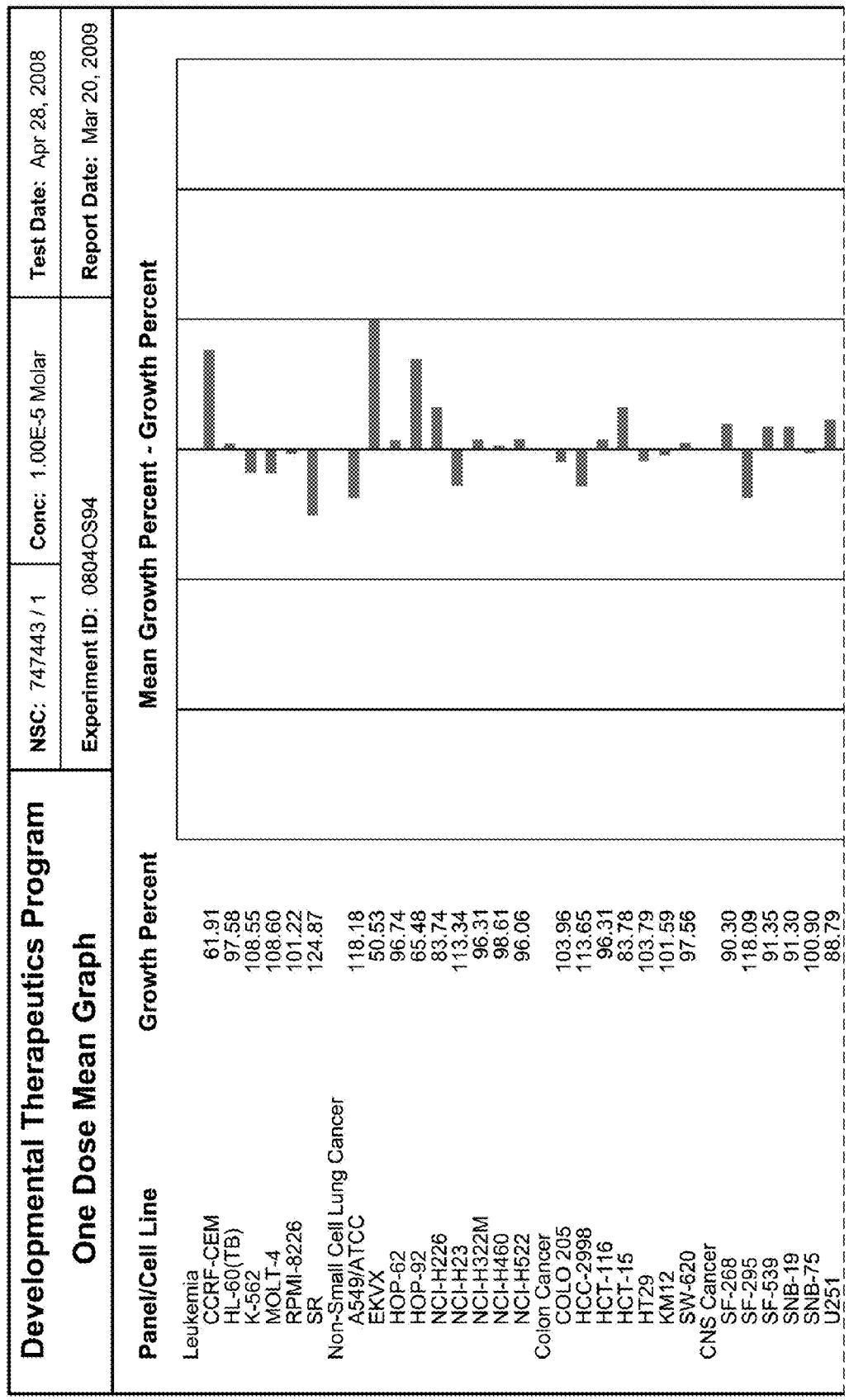
FIG. 6 to FIG. 11 depict the NCI result of compouns f1-0, f1-1, f1-2, f1-11, f1-15 and f3-1, respectively.
Figure 6B:
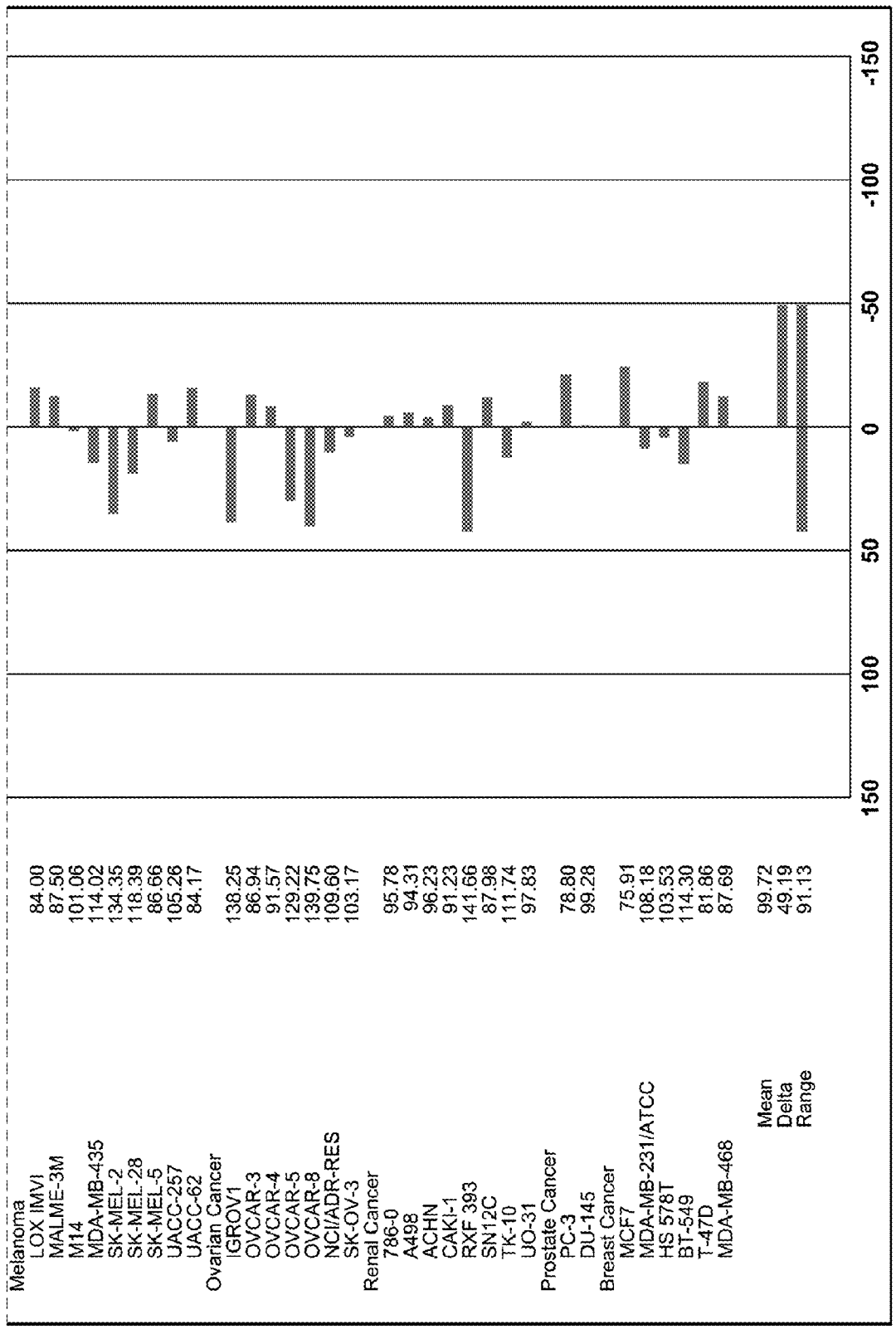
Figure 7A:
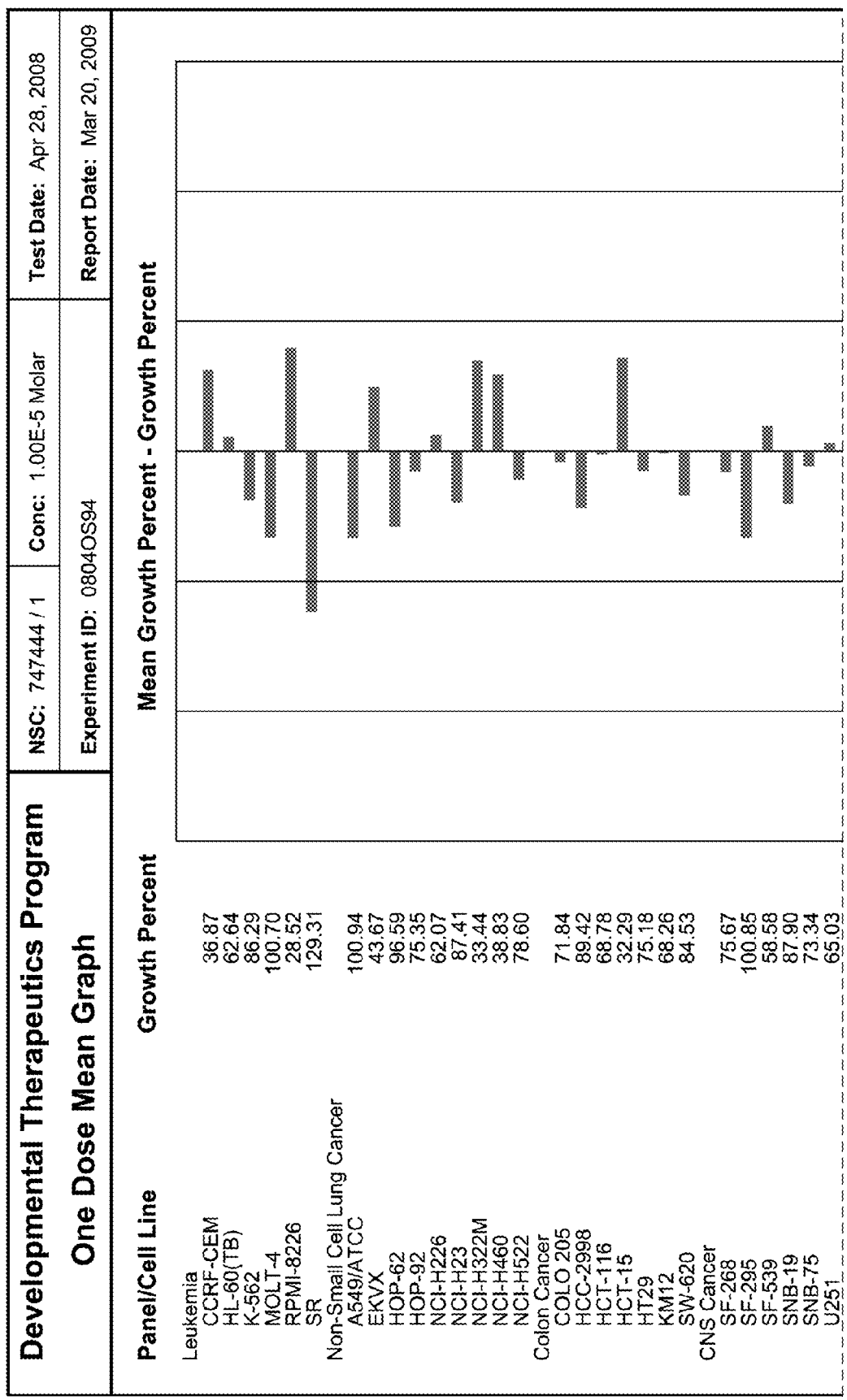
Figure 7B:
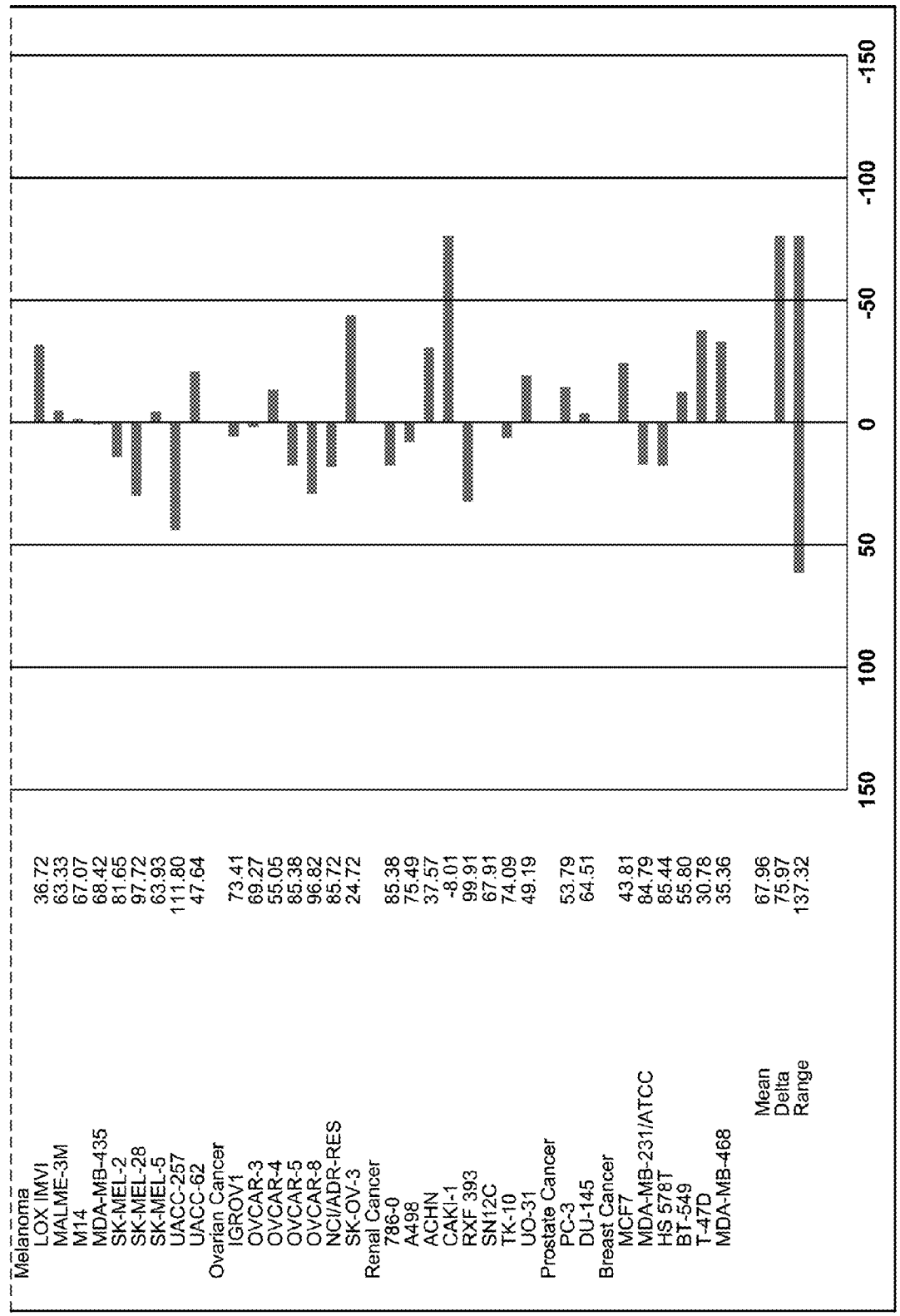
Figure 8A:
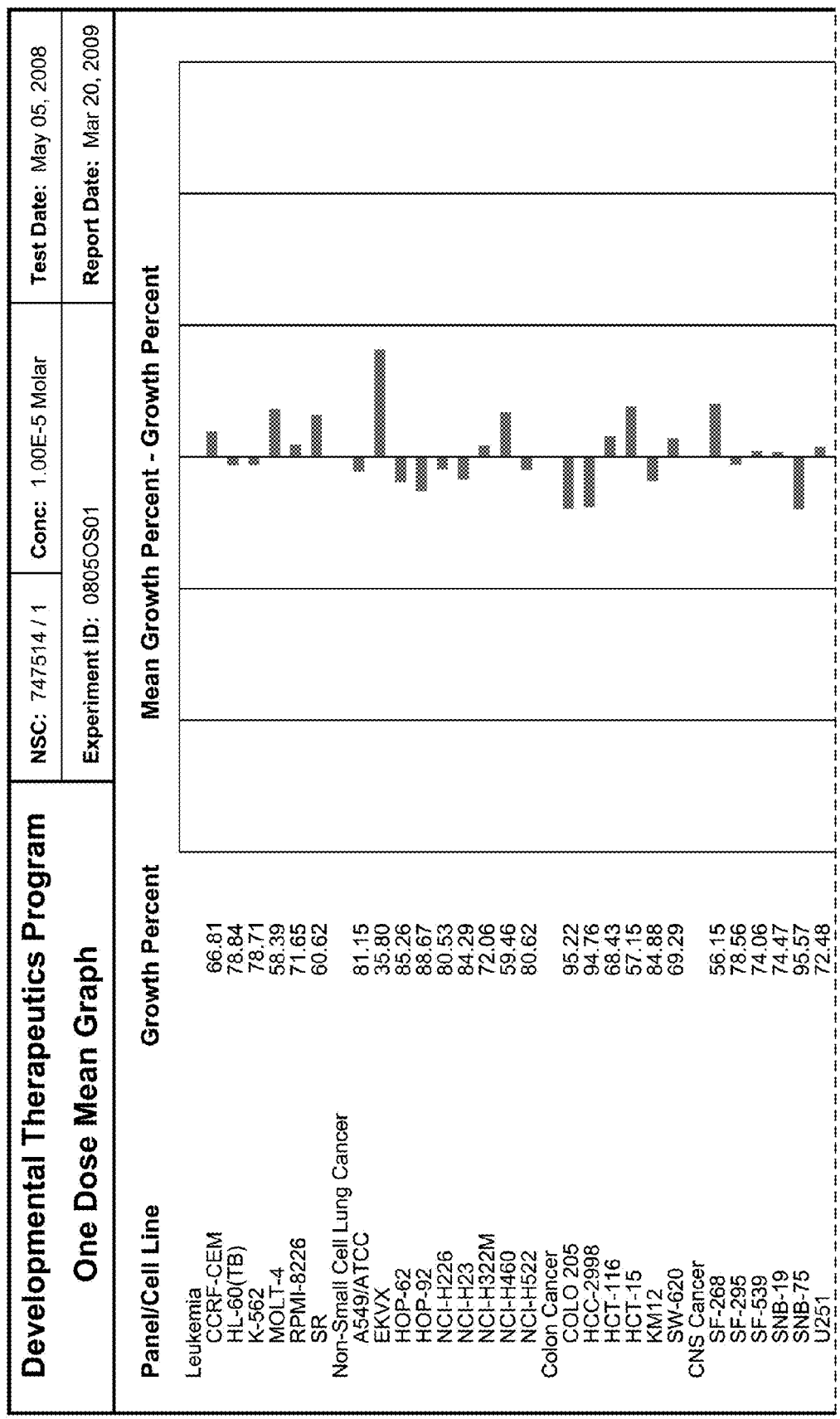
Figure 8B:
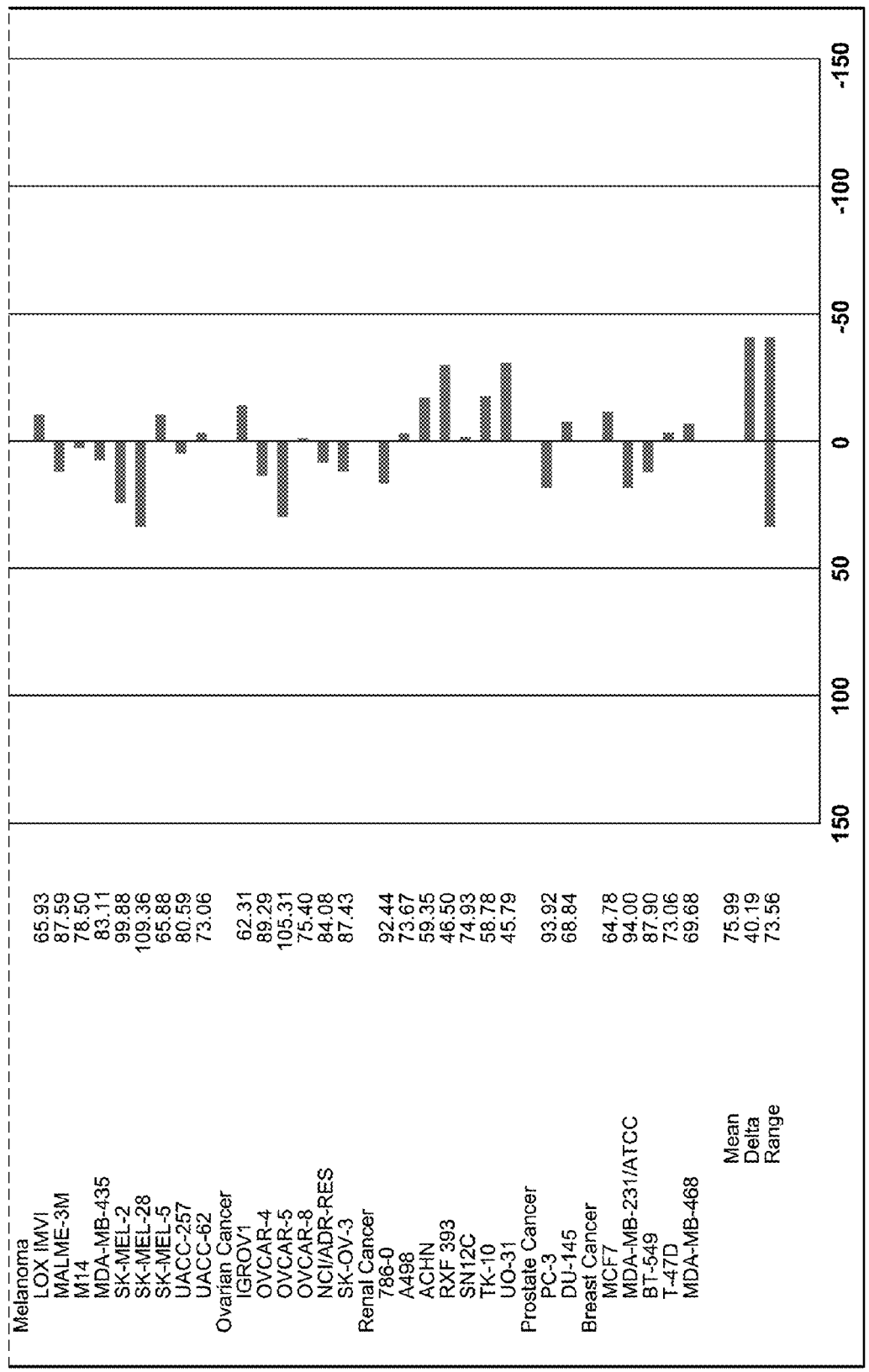
Figure 9A:
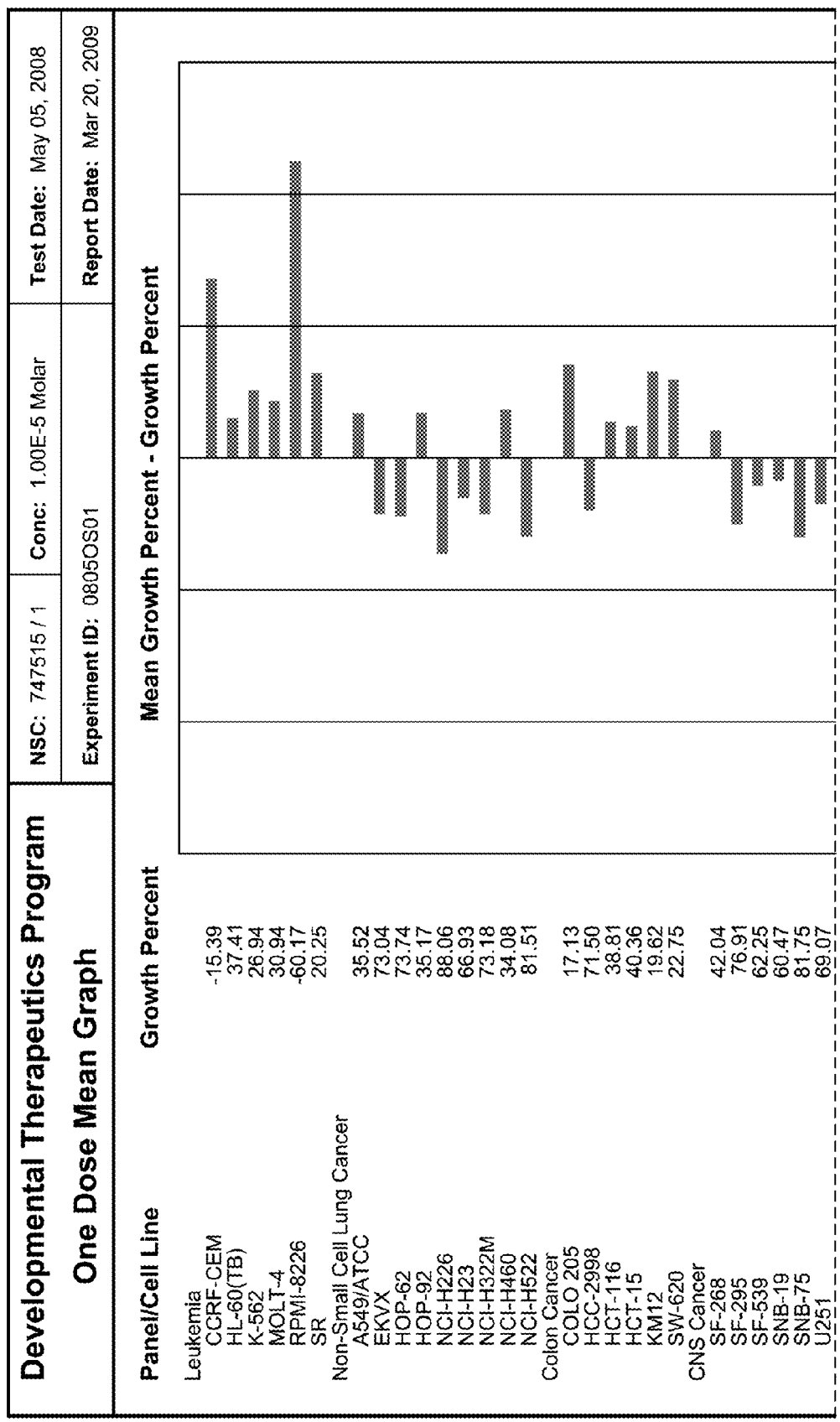
Figure 9B:
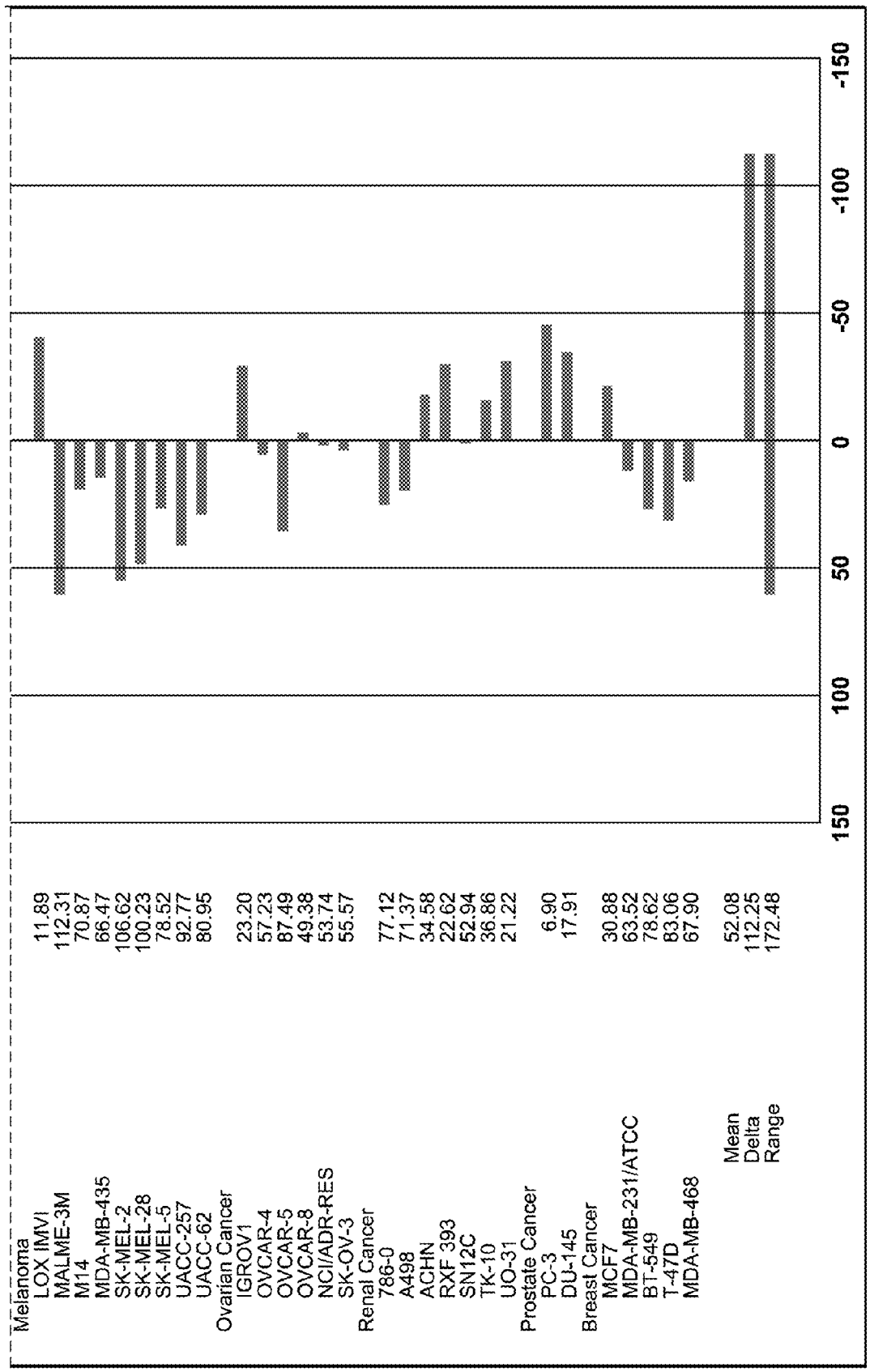
Figure 10A:
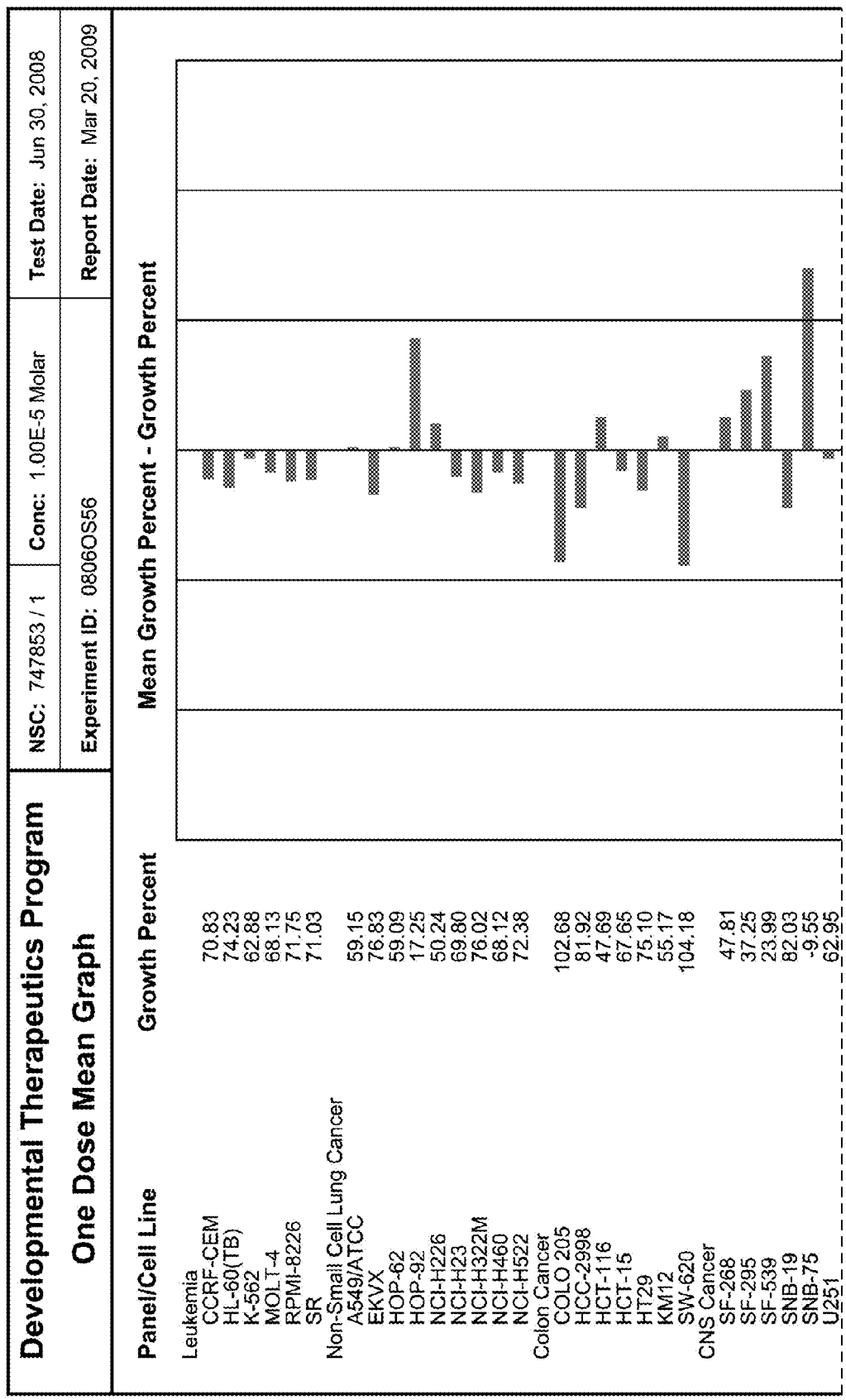
Figure 10B:
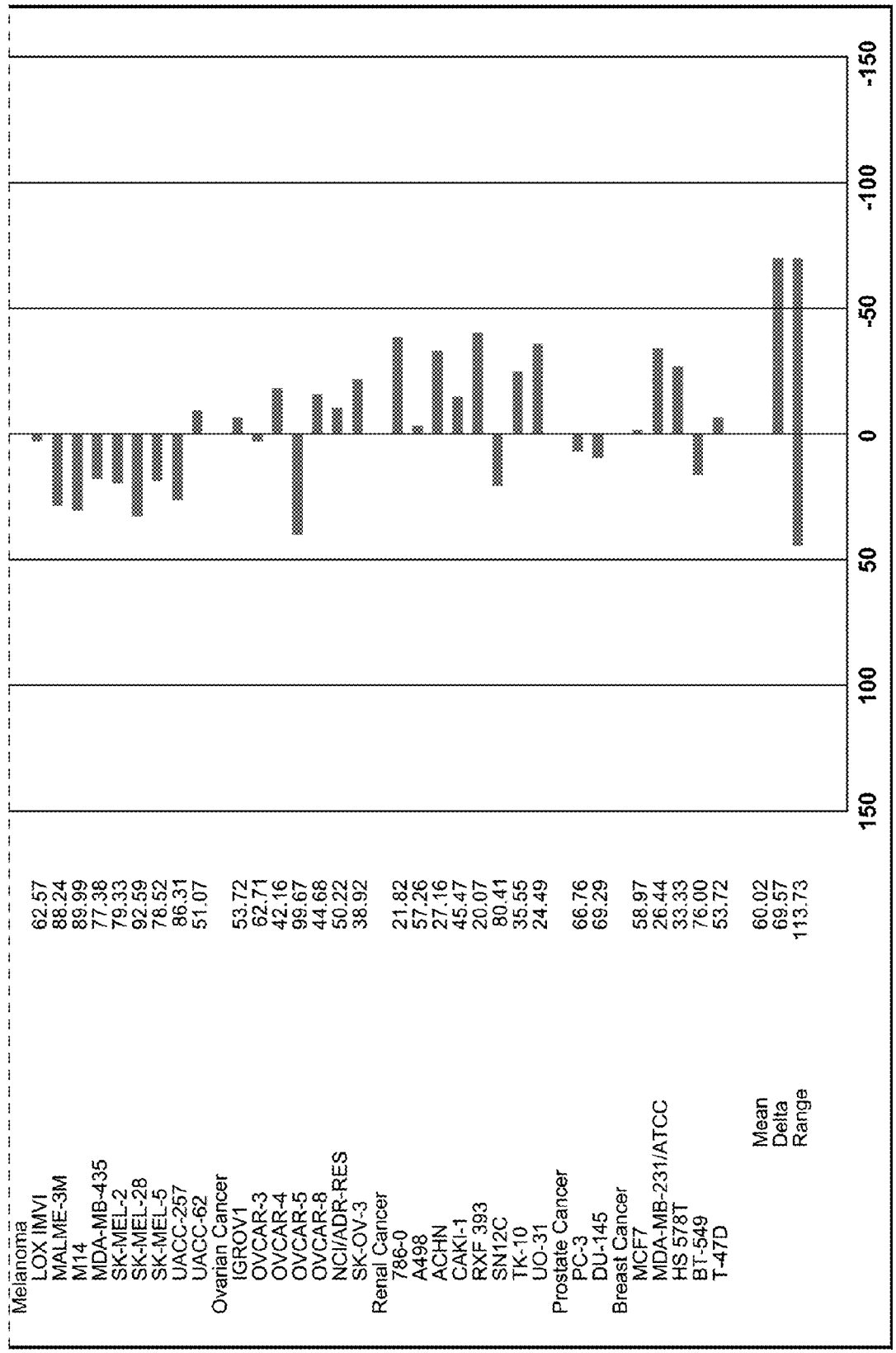
Figure 11A:
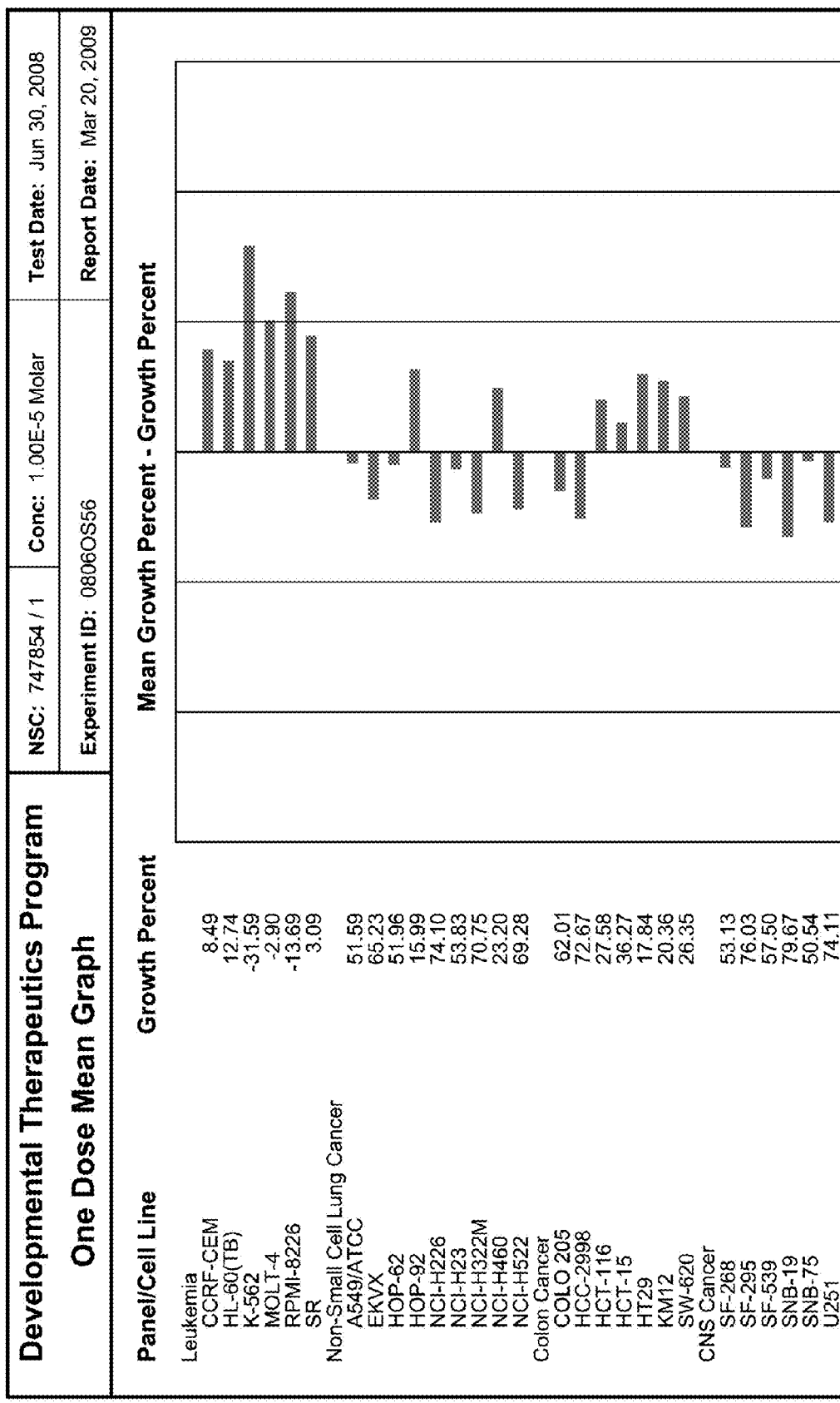
Figure 11B:
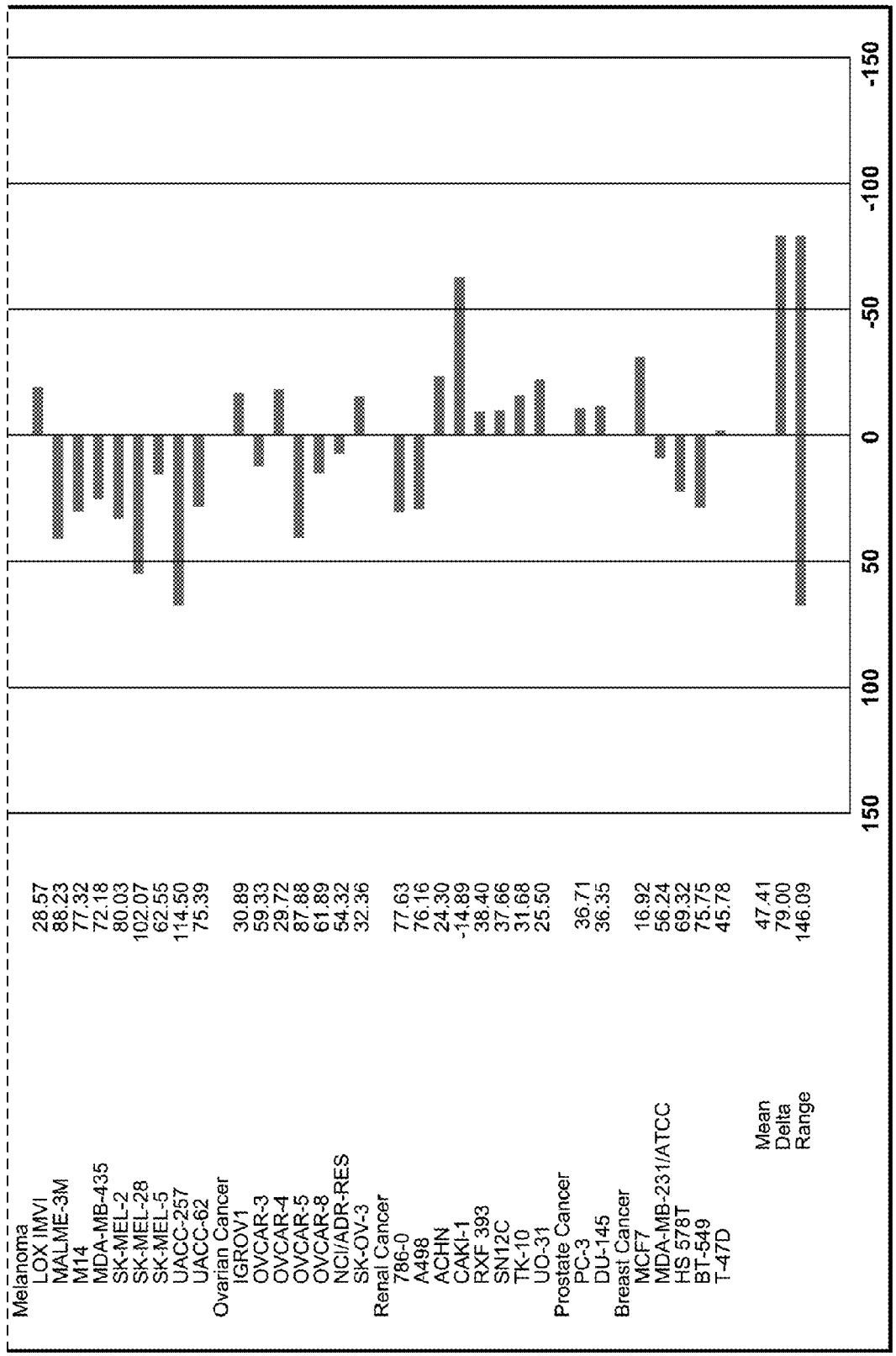

There were 2 compounds f2-1 and f2-6 in this category, which indicated that said compounds could allow rapid growth, maturation, and then apoptosis of said tumor cell without cell toxcity on normal cell (FIG. 5E).

The Substituents of Formula I:

The inventive compound is represented by structural formula I:

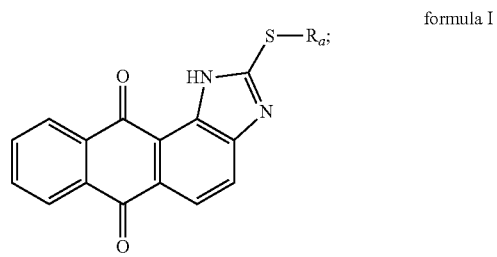

formula I wherein
when $R_a$ is defined as $R_1$ in Table 1, then the structure formula of the compounds f1-0 to f1-23 can be obtained;
when $R_a$ is represented by formula II:

formula II formula II, said $R_2$ is represented in Table 1 (f2-1 to f2-9), then the structure formula of the compounds f2-1 to f2-9 can be obtained;
wherein the compounds f3-1 is represented as formula III in Table 1.

TABLE 1

Result of compounds f1-0 to f3-1 in screening using MTT assay (concentration: 10 μM)

| | | Cell survival rate (%) | | |
|---|---|---|---|---|
| No. | $R_1$ | SVG p12 | GBM8401 | GBM8901 |
| f1-0 | H | 82 ± 5 | 86 ± 25 | 78 ± 13 |
| f1-1 | $CH_2CH_3$ | 98 ± 8 | 42 ± 20 | 58 ± 7 |
| f1-2 | $CH_2CH_2CH_3$ | 99 ± 10 | 62 ± 18 | 62 ± 7 |
| f1-3 | $CH_2CH_2CH_2CH_3$ | 98 ± 7 | 78 ± 16 | 10 ± 4 |
| f1-4 | 1,2-methylphenyl | 58 ± 5 | 25 ± 10 | 18 ± 8 |
| f1-5 | $CH_2CH_2CH_2COOCH_3$ | 92 ± 5 | 70 ± 10 | 80 ± 2 |
| f1-6 | $CH_2CH=CHCOOCH_3$ | 90 ± 6 | 82 ± 7 | 44 ± 5 |
| f1-7 | $CH_2CCH$ | 98 ± 2 | 38 ± 10 | 7 ± 2 |
| f1-8 | $CH_2CH_2CH_2CH_2Cl$ | 66 ± 3 | 43 ± 10 | 65 ± 10 |
| f1-9 | $CH_2CH_2CH_2CH_2Br$ | 80 ± 1 | 62 ± 19 | 98 ± 5 |
| f1-10 | $CH_2CH_2CH_2CH_2CH_2CH_2Cl$ | 81 ± 1 | 78 ± 5 | 60 ± 2 |
| f1-11 | ![pyrrolidine] | 98 ± 1 | 78 ± 10 | 18 ± 2 |
| f1-12 | ![piperidine] | 22 ± 8 | 6 ± 13 | 42 ± 8 |
| f1-13 | ![morpholine] | 62 ± 8 | 38 ± 9 | 68 ± 2 |

TABLE 1-continued

Result of compounds f1-0 to f3-1 in screening using MTT assay
(concentration: 10 µM)

| No. | R | SVG p12 | GBM8401 | GBM8901 |
|---|---|---|---|---|
| f1-14 | 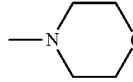 | 12 ± 1 | 6 ± 10 | 10 ± 2 |
| f1-15 | 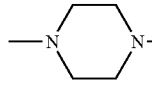 | 11 ± 6 | 8 ± 11 | 63 ± 4 |
| f1-16 | 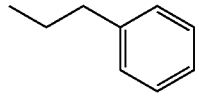 | 60 ± 1 | 30 ± 9 | 39 ± 2 |
| f1-17 | 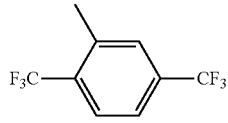 | 80 ± 0 | 23 ± 10 | 48 ± 1 |
| f1-18 | 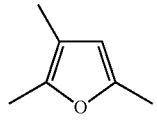 | 65 ± 3 | 23 ± 13 | 42 ± 3 |
| f1-19 | $CH_2C$=$CH_2$ | 89 ± 5 | 42 ± 18 | 50 ± 6 |
| f1-20 | 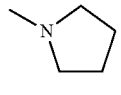 | 46 ± 2 | 28 ± 11 | 30 ± 2 |
| f1-21 | 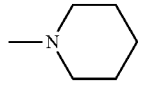 | 63 ± 1 | 30 ± 10 | 38 ± 5 |
| f1-22 | 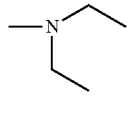 | 80 ± 3 | 40 ± 15 | 28 ± 2 |
| f1-23 | 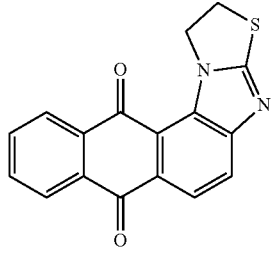 | 80 ± 7 | 82 ± 15 | 18 ± 0 |

| No. | $R_2$ | SVG p12 | GBM8401 | GBM8901 |
|---|---|---|---|---|
| f2-1 | NO₂ (o-nitrophenylmethyl) | 83 ± 4 | 100 ± 16 | 58 ± 3 |
| f2-2 | morpholinomethyl | 96 ± 7 | 92 ± 11 | 43 ± 2 |
| f2-3 | piperazinylmethyl | 62 ± 3 | 62 ± 11 | 38 ± 2 |
| f2-4 | phenethyl | 61 ± 2 | 62 ± 15 | 72 ± 6 |
| f2-5 | 2-methyl-4,α,α,α-CF₃-phenyl | 82 ± 1 | 40 ± 13 | 68 ± 6 |
| f2-6 | trimethylfuryl | 80 ± 2 | 99 ± 15 | 38 ± 7 |
| f2-7 | pyrrolidinylmethyl | 62 ± 5 | 72 ± 18 | 42 ± 7 |
| f2-8 | piperidinylmethyl | 92 ± 3 | 99 ± 25 | 100 ± 0 |
| f2-9 | diethylaminomethyl | 90 ± 8 | 46 ± 13 | 50 ± 0 |
| f3-1 | Formula III | 62 ± 1 | 42 ± 16 | 37 ± 4 |

Example 40

The Cytotoxicity Result of National Cancer Institute's Anticancer Drug Screen The screening system in United State National Cancer Institute (NCI) consists of 60 kinds of different human cancer cells, which can be used to assay the growth-inhibiting ability or cell toxicity of a compound against various cancer and tumor at a certain concentration.

NCI had selected 6 compounds f1-0, f1-1, f3-1, f1-11, f1-2 and f1-15 as test compounds (Table 2). Results were shown in Table 3 and FIG. 6 to FIG. 11. Among these compounds, compound f1-1 was effective against renal cancer cell strain CAKI-1, and could achieve an inhibition effect on the growth of said cancer cell up to −8.01. Compound f1-11 could achieve inhibiting effects against leukemia cell line CCRF-CEM and RPMI-8226, up to −15.39 and −60.17, respectively. Compound f1-2 was effective against central nervous system cancer cell line SNB-75, and could achieve an effect of inhibiting said cancer cell growth up to −9.55. Compound f1-15 was effective against leukemia (blood cancer) cell line K-562, MOLT-4, and RPMI-8226, and could achieve effects of inhibiting said cancer cells growth up to −31.59, −2.90 and −13.69, respectively. Further, compound f1-15 was effective also against renal cancer cell line CAKI-1, and could achieve an effect of inhibiting said cancer cell growth up to −14.89. In addition, in the assay against human multiple drug-resistant breast cancer cell NCI/ADR-RES, compounds f1-0, f1-1, f3-1, f1-11 and f1-15 were found to have drug-resistance against adriamycin (ADR).

TABLE 2

The list of tested comopunds in NCI's screen (One Dose Mean Graph)

| No | Formula | Compound info. | Code | NSC no. |
|---|---|---|---|---|
| 1 | | 2-Mercapto-1(3)H-anthra[1,2-d]imidazole-6,11-dione<br>Chemical Formula: $C_{15}H_8N_2O_2S$<br>Molecular Weight: 280.0306 | f1-0 | 747443<br>(FIG. 5) |
| 2 | | 2-(Ethylthio)-1H-anthra[1,2-d]imidazole-6,11-dione<br>Chemical Formula: $C_{17}H_{12}N_2O_2S$<br>Molecular Weight: 308.35 | f1-1 | 747444<br>(FIG. 6) |
| 3 | | 2-(2-N-ethyl thio)-1H-anthra[1,2-d]imidazole-6,11-dione<br>Chemical Formula: $C_{17}H_{10}N_2O_2S$<br>Molecular Weight: 306.34 | f3-1 | 747514<br>(FIG. 7) |
| 4 | | 2-(2-(Piperidin-1-yl)ethylthio)-1H-anthra[1,2-d]imidazole-6,11-dione<br>Chemical Formula: $C_{21}H_{19}N_3O_3S$<br>Molecular Weight: 377.19 | f1-11 | 747515<br>(FIG. 8) |
| 5 | | 2-(propylthio)-1H-anthra[1,2-d]imidazole-6,11-dione<br>Chemical Formula: $C_{18}H_{14}N_2O_2S$<br>Molecular Weight: 322.07 | f1-2 | 747853<br>(FIG. 9) |

TABLE 2-continued

The list of tested comopunds in NCI's screen (One Dose Mean Graph)

| No | Formula | Compound info. | Code | NSC no. |
|---|---|---|---|---|
| 6 | (structure) | 2-(3-dimethylamino)propylthio)-1H-anthra[1,2-d]imidazole-6,11-dione<br>Chemical Formula: $C_{20}H_{19}N_3O_2S$<br>Molecular Weight: 365.44 | f1-15 | 747854 (FIG. 10) |

*The tested concentration of compounds is 1.00E−5 Molar.

TABLE 3

Cytotoxicity of selected compounds f1-0, f1-1, f3-1, f1-11, f1-2 & f1-15 ($10^{-5}$M) in the NCI drug screen

| | Compound/Growth Percent[a] | | | | | |
|---|---|---|---|---|---|---|
| Panel/Cell Line | f1-0<br>747443 | f1-1<br>747444 | f3-1<br>747514 | f1-11<br>747515 | f1-2<br>747853 | f1-15<br>747854 |
| Leukemia | | | | | | |
| CCRF-CEM | 61.91 | 36.87 | 66.81 | −15.39 | 70.83 | 8.49 |
| HL-60(TB) | 97.58 | 62.64 | 78.84 | 37.41 | 74.23 | 12.74 |
| K-562 | 108.55 | 86.29 | 78.71 | 26.94 | 62.88 | −31.59 |
| MOLT-4 | 108.60 | 100.70 | 58.39 | 30.94 | 68.13 | −2.90 |
| RPMI-8226 | 101.22 | 28.52 | 71.65 | −60.17 | 71.75 | −13.69 |
| SR | 124.87 | 129.31 | 60.62 | 20.25 | 71.03 | 3.09 |
| Non-Small Cell Lung Cancer | | | | | | |
| A549/ATCC | 118.18 | 100.94 | 81.15 | 35.52 | 59.15 | 51.59 |
| EKVX | 50.53 | 43.67 | 35.80 | 73.04 | 76.83 | 65.23 |
| HOP-62 | 96.74 | 96.59 | 85.26 | 73.74 | 59.09 | 51.96 |
| HOP-92 | 65.48 | 75.35 | 88.67 | 35.17 | 17.25 | 15.99 |
| NCI-H226 | 83.74 | 62.07 | 80.53 | 88.06 | 50.24 | 74.10 |
| NCI-H23 | 113.34 | 87.41 | 84.29 | 66.93 | 69.80 | 53.83 |
| NCI-H322M | 96.31 | 33.44 | 72.06 | 73.18 | 76.02 | 70.75 |
| NCI-H460 | 98.61 | 38.83 | 59.46 | 34.08 | 68.12 | 23.20 |
| NCI-H522 | 96.06 | 78.60 | 80.62 | 81.51 | 72.38 | 69.28 |
| Colon Cancer | | | | | | |
| COLO 205 | 103.96 | 71.84 | 95.22 | 17.13 | 102.68 | 62.01 |
| HCC-2998 | 113.65 | 89.42 | 94.76 | 71.50 | 81.92 | 72.67 |
| HCT-116 | 96.31 | 68.78 | 68.43 | 38.81 | 47.69 | 27.58 |
| HCT-15 | 83.78 | 32.29 | 57.15 | 40.36 | 67.65 | 36.27 |
| HT29 | 103.79 | 75.18 | — | — | 75.10 | 17.84 |
| KM12 | 101.59 | 68.26 | 84.88 | 19.62 | 55.17 | 20.36 |
| SW-620 | 97.56 | 84.53 | 69.29 | 22.75 | 104.18 | 26.35 |
| CNS Cancer | | | | | | |
| SF-268 | 90.30 | 75.67 | 56.15 | 42.04 | 47.81 | 53.13 |
| SF-295 | 118.09 | 100.85 | 78.56 | 76.91 | 37.25 | 76.03 |
| SF-539 | 91.35 | 58.58 | 74.06 | 62.25 | 23.99 | 57.50 |
| SNB-19 | 91.30 | 87.90 | 74.47 | 60.47 | 82.03 | 79.67 |
| SNB-75 | 100.90 | 73.34 | 95.57 | 81.75 | −9.55 | 50.54 |
| U251 | 88.79 | 65.03 | 72.48 | 69.07 | 62.95 | 74.11 |
| Melanoma | | | | | | |
| LOX IMVI | 84.00 | 36.72 | 65.93 | 11.89 | 62.57 | 28.57 |
| MALME-3M | 87.50 | 63.33 | 87.59 | 112.31 | 88.24 | 88.23 |
| M14 | 101.06 | 67.07 | 78.50 | 70.87 | 89.99 | 77.32 |
| MDA-MB-435 | 114.02 | 68.42 | 83.11 | 66.47 | 77.38 | 72.18 |
| SK-MEL-2 | 134.35 | 81.65 | 99.88 | 106.62 | 79.33 | 80.03 |
| SK-MEL-28 | 118.39 | 97.72 | 109.36 | 100.23 | 92.59 | 102.07 |
| SK-MEL-5 | 86.66 | 63.93 | 65.88 | 78.52 | 78.52 | 62.55 |
| UACC-257 | 105.26 | 111.80 | 80.59 | 92.77 | 86.31 | 114.50 |
| UACC-62 | 84.17 | 47.64 | 73.06 | 80.95 | 51.07 | 75.39 |

TABLE 3-continued

Cytotoxicity of selected compounds f1-0, f1-1, f3-1, f1-11, f1-2 & f1-15 ($10^{-5}$M) in the NCI drug screen

| | Compound/Growth Percent[a] | | | | | |
|---|---|---|---|---|---|---|
| Panel/Cell Line | f1-0 747443 | f1-1 747444 | f3-1 747514 | f1-11 747515 | f1-2 747853 | f1-15 747854 |
| Ovarian Cancer | | | | | | |
| IGROV1 | 138.25 | 73.41 | 62.31 | 23.20 | 53.72 | 30.89 |
| OVCAR-3 | 86.94 | 69.27 | — | — | 62.71 | 59.33 |
| OVCAR-4 | 91.57 | 55.05 | 89.29 | 57.23 | 42.16 | 29.72 |
| OVCAR-5 | 129.22 | 85.38 | 105.31 | 87.49 | 99.67 | 87.88 |
| OVCAR-8 | 139.75 | 96.82 | 75.40 | 49.38 | 44.68 | 61.89 |
| NCI/ADR-RES | 109.60 | 85.72 | 84.08 | 53.74 | 50.22 | 54.32 |
| SK-OV-3 | 103.17 | 24.72 | 87.43 | 55.57 | 38.92 | 32.36 |
| Renal Cancer | | | | | | |
| 786-0 | 95.78 | 85.38 | 92.44 | 77.12 | 21.82 | 77.63 |
| A498 | 94.31 | 75.49 | 73.67 | 71.37 | 57.26 | 76.16 |
| ACHN | 96.23 | 37.57 | 59.35 | 34.58 | 27.16 | 24.30 |
| CAKI-1 | 91.23 | −8.01 | — | — | 45.47 | −14.89 |
| RXF 393 | 141.66 | 99.91 | 46.50 | 22.62 | 20.07 | 38.40 |
| SN12C | 87.98 | 67.91 | 74.93 | 52.94 | 80.41 | 37.66 |
| TK-10 | 111.74 | 74.09 | 58.78 | 36.86 | 35.55 | 31.68 |
| UO-31 | 97.83 | 49.19 | 45.79 | 21.22 | 24.49 | 25.50 |
| Prostate Cancer | | | | | | |
| PC-3 | 78.80 | 53.79 | 93.92 | 6.90 | 66.76 | 36.71 |
| DU-145 | 99.28 | 64.51 | 68.84 | 17.91 | 69.29 | 36.35 |
| Breast Cancer | | | | | | |
| MCF7 | 75.91 | 43.81 | 64.78 | 30.88 | 58.97 | 16.92 |
| MDA-MB-231/ATCC | 108.18 | 84.79 | 94.00 | 63.52 | 26.44 | 56.24 |
| HS 578T | 103.53 | 85.44 | — | — | 33.33 | 69.32 |
| BT-549 | 114.30 | 55.80 | 87.90 | 78.62 | 76.00 | 75.75 |
| T-47D | 81.86 | 30.78 | 73.06 | 83.06 | 53.72 | 45.78 |
| MDA-MB-468 | 87.69 | 35.36 | 69.68 | 67.90 | — | — |
| Mean | 99.72 | 67.96 | 75.99 | 52.08 | 60.02 | 47.41 |
| Delta | 49.19 | 75.97 | 40.19 | 112.25 | 69.57 | 79.00 |
| Range | 91.13 | 137.32 | 73.56 | 172.48 | 113.73 | 146.09 |

[a]Data obtained from NCI in vitro 60-cell Drug Screen program at 1.00E−5 Molar concentration.
"—" represent "not test".

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A thio-substituted[1,2-d]anthra[1,2-d]imidazole-6,11-dione derivative is selected from the group consisting of 2-mercapto-(1H)-anthra-[1,2-d]-imidazole-6,11-dione, 2-(ethylthio)-1H-anthra-[1,2-d]-imidazole-6,11-dione, 2-(propylthio)-1H-anthra[1,2-d]-imidazole-6,11-dione, 2-(butylthio)-1H-anthra-[1,2-d]-imidazole-6,11-dione, 2-(2-methylbenzylthio)-1H-anthra-[1,2-d]-imidazole-6,11-dione, methyl-(6,11-dioxo-6,11-dihydro-1H-anthra-[1,2-d]-imidazol-2-ylthio)-butanoate, (E)-methyl-4-(6,11-dioxo-6,11-dihydro-/H-anthra-[1,2-d]imidazol-2-ylthio)-but-2-enoate, 2-(prop-2-ynylthio)-/H-anthra-[1,2-d]-imidazole-6,11-dione, 2-(4-chlorobutylthio)-1H-anthra-[1,2-d]-imidazole-6,11-dione, 2-(5-bromopentylthio)-1H-anthra-[1,2-d]-imidazole-6,11-dione, 2-(6-chlorohexylthio)-1H-anthra[1,2-d]-imidazole-6,11-dione, 2-(2-(piperidin-1-yl)-ethylthio)-1H-anthra-[1,2-d]-imidazole-6,11-dione, 2-(2-morpholinoethylthio)-1H-anthra[1,2-d]-imidazole-6,11-dione, 2-(3-(piperidin-1-yl)propylthio)-1H-anthra-[1,2-d]-imidazole-6,11-dione, 2-(3-(dimethylamino)propylthio)-1H-anthra-[1,2-d]-imidazole-6,11-dione, 2-(2-morpholino-2-oxoethylthio)-1H-anthra-[1,2-d]-imidazole-6,11-dione, 2-(3-morpholino-3-oxopropylthio)-1H-anthra-[1,2-d]-imidazole-6,11-dione, 2-(6,11-dioxo-6,11-dihydro-1H-anthra-[1,2-d]-imidazol-2-ylthio)-N,N-diethylacetamide, 2-(allylthio)-1H-anthra-[1,2-d]-imidazole-6,11-dione, 3-(6,11-dioxo-6,11-dihydro-1H-anthra-[1,2-d]-imidazol-2-ylthio)-N,N-diethylpropanamide, 2-(2-oxo-2-(pyrrolidin-1-yl)-ethylthio)-1H-anthra-[1,2-d]-imidazole-6,11-dione, 2-(3-oxo-3-(pyrrolidin-1-yl)-propylthio)-1H-anthra-[1,2-d]-imidazole-6,11-dione, 2-(6,11-dioxo-6,11-dihydro-1H-anthra-[1,2-d]-imidazol-2-ylthio)-N,N-dipropylacetamide, S-6,11-dioxo-6,11-dihydro-1H-anthra-[1,2-d]-imidazol-2-yl-2-nitrobenzothioate, S-6,11-dioxo-6,11-dihydro-1H-anthra-[1,2-d]-imidazol-2-yl-morpholine-4-carbothioate, S-6,11-dioxo-6,11-dihydro-1H-anthra-[1,2-d]-imidazol-2-yl-4-methylpiperazine-1-carbothioate, S-6,11-dioxo-6,11-dihydro-1H-anthra-[1,2-d]-imidazol-2-yl-3-phenylpropanethioate, S-6,11-dioxo-6,11-dihydro-1H-anthra-[1,2-d]-imidazol-2-yl-2,5-bis(trifluoromethyl) benzothioate, S-6,11-dioxo-6,11-dihydro-1H-anthra[1,2-d]-imidazol-2-yl-2,5-dimethylfuran-3-carbothioate, S-6,11-dioxo-6,11-dihydro-1H-anthra-[1,2-d]-imidazol-2-yl-pyrrolidine-1-carbothioate, S-6,11-dioxo-6,11-dihydro-1H-anthra-[1,2-d]-imidazol-2-yl-piperidine-1-carbothioate, S-6,11-dioxo-6,11-dihydro-1H-anthra-[1,2-d]-imidazol-2-yl-diethylcarbamothioate, and 2-(2-n-ethylthio)-1H-anthra-[1,2-d]-imidazole-6,11-dione.

2. A method for preparing the thio-substituted[1,2-d]anthra[1,2-d]imidazole-6,11-dione derivative as recited in claim 1, comprising the following steps:

A. cyclizing step:

dissolving 1,2-diaminoanthraquinone in N-N-dimethylformamide, adding thereto with carbon disulfide, and then with triethylamine under stirring; after completion of reaction, cooling down the mixed solution, filtering to collect the precipitate, and finally, rinsing the precipitate with ethanol to obtain compound 2-mercapto-(1H)-anthra-[1,2-d]-imidazole-6,11-dione;

B. alkylation reaction:

dissolving 2-mercapto-(1H)-anthra-[1,2-d]-imidazole-6,11-dione in N-N-dimethylformamide, adding thereto with alkyl halide, and then with potassium hydroxide (KOH); after completion of reaction, cooling down the mixed solution, filtering to collect the precipitate, and finally, recrystallizing the precipitate in ethanol to obtain 2-(ethylthio)-1H-anthra-[1,2-d]-imidazole-6,11-dione, 2-(propylthio)-1H-anthra-[1,2-d]-imidazole-6,11-dione, 2-(butylthio)-1H-anthra-[1,2-d]-imidazole-6,11-dione, 2-(2-methylbenzylthio)-1H-anthra-[1,2-d]-imidazole-6,11-dione, methyl-(6,11-dioxo-6,11-dihydro-1H-anthra-[1,2-d]-imidazol-2-ylthio)-butanoate, (E)-methyl-4-(6,11-dioxo-6,11-dihydro-1H-anthra-[1,2-d]imidazol-2-ylthio)-but-2-enoate, 2-(prop-2-ynylthio)-1H-anthra-[1,2-d]-imidazole-6,11-dione, 2-(4-chlorobutylthio)-1H-anthra-[1,2-d]-imidazole-6,11-dione, 2-(5-bromopentylthio)-1H-1-anthra-[1,2-d]-imidazole-6,11-dione, 2-(6-chlorohexylthio)-1H-anthra-[1,2-d]-imidazole-6,11-dione, 2-(2-(piperidin-1-yl)-ethylthio)-1H-anthra-[1,2-d]-imidazole-6,11-dione, 2-(2-morpholinoethylthio)-1H-anthra-[1,2-d]-imidazole-6,11-dione, 2-(3-(piperidin-1-yl)propylthio)-1H-anthra-[1,2-d]-imidazole-6,11-dione, 2-(3-(dimethylamino)propylthio)-1H-anthra-[1,2-d]-imidazole-6,11-dione, 2-(2-morpholino-2-oxoethylthio)-1H-anthra-[1,2-d]-imidazole-6,11-dione, 2-(3-morpholino-3-oxopropylthio)-1H-anthra-[1,2-d]-imidazole-6,11-dione, 2-(6,11-dioxo-6,11-dihydro-1H-anthra-[1,2-d]-imidazol-2-ylthio)-N,N-diethylacetamide, 2-(allylthio)-1H-anthra-[1,2-d]-imidazole-6,11-dione, 3-(6,11-dioxo-6,11-dihydro-1H-anthra-[1,2-d]-imidazol-2-ylthio)-N,N-diethylpropanamide, 2-(2-oxo-2-(pyrrolidin-1-yl)-ethylthio)-1H-anthra-[1,2-d]-imidazole-6,11-dione, 2-(3-oxo-3-(pyrrolidin-1-yl)-propylthio)-1H-anthra-[1,2-d]-imidazole-6,11-dione, and 2-(6,11-dioxo-6,11-dihydro-1H-anthra-[1,2-d]-imidazol-2-ylthio)-N,N-dipropylacetamide;

dissolving 2-mercapto-1H-anthra-[1,2-d]-imidazole-6,11-dione in N-N-dimethylformamide, adding thereto with acyl chloride, and then with triethylamine; after completion of reaction, cooling down the mixed solution, filtering to collect the precipitate, and finally, recrystallizing the precipitate in ethanol to obtain S-6,11-dioxo-6,11-dihydro-1H-anthra-[1,2-d]-imidazol-2-yl-2-nitrobenzothioate, S-6,11-dioxo-6,11-dihydro-1H-anthra-[1,2-d]-imidazol-2-yl-morpholine-4-carbothioate, S-6,11-dioxo-6,11-dihydro-1H-anthra-[1,2-d]-imidazol-2-yl-4-methylpiperazine-1-carbothioate, S-6,11-dioxo-6,11-dihydro-1H-anthra-[1,2-d]-imidazol-2-yl-3-phenylpropanethioate, S-6,11-dioxo-6,11-dihydro-1H-anthra-[1,2-d]-imidazol-2-yl-2,5-bis(trifluoromethyl) benzothioate, S-6,11-dioxo-6,11-dihydro-1H-anthra-[1,2-d]-imidazol-2-yl-2,5-dimethylfuran-3-carbothioate, S-6,11-dioxo-6,11-dihydro-1H-anthra-[1,2-d]-imidazol-2-yl-pyrrolidine-1-carbothioate, S-6,11-dioxo-6,11-dihydro-1H-anthra-[1,2-d]-imidazol-2-yl-piperidine-1-carbothioate, and S-6,11-dioxo-6,11-dihydro-1H-anthra-[1,2-d]-imidazol-2-yl-diethylcarbamothioate;

dissolving 2-mercapto-1H-anthra-[1,2-d]-imidazole-6,11-dione in N-N-dimethylformamide, adding thereto with 1,2-dichloroethane, and then with potassium hydroxide (KOH); after completion of reaction, cooling down the mixed solution, filtering to collect the precipitate, and finally, recrystallizing the precipitate in ethanol to obtain 2-(2-n-ethylthio)-1H-anthra-[1,2-d]-imidazole-6,11-dione.

3. A compound as recited in claim 1, wherein said compound is selected from the group consisting of compounds 2-(ethylthio)-1H-anthra-[1,2-d]-imidazole-6,11-dione, 2-(5-bromopentylthio)-1H-anthra-[1,2-d]-imidazole-6,11-dione, 2-(2-(piperidin-1-yl)-ethylthio)-1H-anthra-[1,2-d]-imidazole-6,11-dione, 2-(6,11-dioxo-6,11-dihydro-1H-anthra-[1,2-d]-imidazol-2-ylthio)-N,N-diethylacetamide, 2-(allylthio)-1H-anthra-[1,2-d]-imidazole-6,11-dione, 2-(2-oxo-2-(pyrrolidin-1-yl)-ethylthio)-1H-anthra-[1,2-d]-imidazole-6,11-dione, S-6,11-dioxo-6,11-dihydro-1H-anthra-[1,2-d]-imidazol-2-yl-2-nitrobenzothioate, S-6,11-dioxo-6,11-dihydro-1H-anthra-[1,2-d]-imidazol-2-yl-morpholine-4-carbothioate, S-6,11-dioxo-6,11-dihydro-1H-anthra-[1,2-d]-imidazol-2-yl-4-methylpiperazine-1-carbothioate, S-6,11-dioxo-6,11-dihydro-1H-anthra-[1,2-d]-imidazol-2-yl-2,5-dimethylfuran-3-carbothioate, and 2-(2-n-ethylthio)-1H-anthra-[1,2-d]-imidazole-6,11-dione.

4. A compound as recited in claim 1, wherein said compound is selected from the group consisting of compounds 2-(ethylthio)-1H-anthra-[1,2-d]-imidazole-6,11-dione, 2-(propylthio)-1H-anthra-[1,2-d]-imidazole-6,11-dione, 2-(butylthio)-1H-anthra-[1,2-d]-imidazole-6,11-dione, 2-(2-methylbenzylthio)-1H-anthra-[1,2-d]-imidazole-6,11-dione, methyl-(6,11-dioxo-6,11-dihydro-1H-anthra-[1,2-d]-imidazol-2-ylthio)-butanoate, 2-(prop-2-ynylthio)-1H-anthra-[1,2-d]-imidazole-6,11-dione, 2-(4-chlorobutylthio)-1H-anthra-[1,2-d]-imidazole-6,11-dione, 2-(5-bromopentylthio)-1H-anthra-[1,2-d]-imidazole-6,11-dione, 2-(6-chlorohexylthio)-1H-anthra-[1,2-d]-imidazole-6,11-dione, 2-(2-(piperidin-1-yl)-ethylthio)-1H-anthra-[1,2-d]-imidazole-6,11-dione, 2-(2-(piperidin-1-yl)-ethylthio)-1H-anthra-[1,2-d]-imidazole-6,11-dione, 2-(2-morpholinoethylthio)-1H-anthra-[1,2-d]-imidazole-6,11-dione, 2-(3-(piperidin-1-yl)propylthio)-1H-anthra-[1,2-d]-imidazole-6,11-dione, 2-(3-(dimethylamino)propylthio)-1H-anthra-[1, 2-d]-imidazole-6,11-dione, 2-(2-morpholino-2-oxoethylthio)-1H-anthra-[1,2-d]-imidazole-6,11-dione, 2-(3-morpholino-3-oxopropylthio)-1H-anthra-[1,2-d]-imidazole-6,11-dione, 2-(6,11-dioxo-6,11-dihydro-1H-anthra-[1,2-d]-imidazol-2-ylthio)-N,N-diethylacetamide, 2-(allylthio)-1H-anthra-[1,2-d]-imidazole-6,11-dione, 3-(6,11-dioxo-6,11-dihydro-1H-anthra-[1,2-d]-imidazol-2-ylthio)-N,N-diethylpropanamide, 2-(2-oxo-2-(pyrrolidin-1-yl)-ethylthio)-1H-anthra-[1,2-d]-imidazole-6,11-dione, 2-(3-oxo-3-(pyrrolidin-1-yl)-propylthio)-1H-anthra-[1,2-d]-imidazole-6,11-dione, S-6,11-dioxo-6,11-dihydro-1H-anthra-[1,2-d]-imidazol-2-yl-morpholine-4-carbothioate, S-6,11-dioxo-6,11-dihydro-1H-anthra-[1,2-d]-imidazol-2-yl-4-methylpiperazine-1-carbothioate, S-6,11-dioxo-6,11-dihydro-1H-anthra-[1,2-d]-imidazol-2-yl-3-phenylpropanethioate, S-6,11-dioxo-6,11-dihydro-1H-anthra-[1,2-d]-imidazol-2-yl-pyrrolidine-1-carbothioate, S-6,11-dioxo-6,11-dihydro-1H-anthra-[1,2-d]-imidazol-2-yl-diethylcarbamothioate and 2-(2-n-ethylthio)-1H-anthra-[1,2-d]-imidazole-6,11-dione.

5. A compound as recited in claim 1, wherein said compound is selected from the group consisting of compounds 2-mercapto-1(3)-H-anthra-[1,2-d]-imidazole-6,11-dione, 2-(ethylthio)-1H-anthra-[1,2-d]-imidazole-6,11-dione, 2-(propylthio)-1H-anthra-[1,2-d]-imidazole-6,11-dione, 2-(butylthio)-1H-anthra-[1,2-d]-imidazole-6,11-dione, 2-(2-methylbenzylthio)-1H-anthra-[1,2-d]-imidazole-6,11-dione, (E)-methyl-4-(6,11-dioxo-6,11-dihydro-1H-anthra-[1,2-d]-imidazol-2-ylthio)-but-2-enoate, 2-(prop-2-ynylthio)-1H-anthra-[1,2-d]-imidazole-6,11-dione, 2-(4-chlorobutylthio)-1H-anthra-[1,2-d]-imidazole-6,11-dione, 2-(6-chlorohexylthio)-1H-anthra-[1,2-d]-imidazole-6,11-dione, 2-(2-(piperidin-1-yl)-ethylthio)-1H-anthra-[1,2-d]-imidazole-6,11-dione, 2-(2-(piperidin-1-yl)-ethylthio)-1H-anthra-[1,2-d]-imidazole-6,11-dione, 2-(2-morpholinoethylthio)-1H-anthra-[1,2-d]-imidazole-6,11-dione, 2-(3-(piperidin-1-yl)propylthio)-1H-anthra-[1,2-d]-imidazole-6,11-dione, 2-(3-(dimethylamino)propylthio)-1H-anthra-[1,2-d]-imidazole-6,11-dione, 2-(2-morpholino-2-oxoethylthio)-1H-anthra-[1,2-d]-imidazole-6,11-dione, 2-(3-morpholino-3-oxopropylthio)-1H-anthra-[1,2-d]-imidazole-6,11-dione, 2-(6,11-dioxo-6,11-dihydro-1H-anthra-[1,2-d]-imidazol-2-ylthio)-N,N-diethylacetamide, 2-(allylthio)-1H-anthra-[1,2-d]-imidazole-6,11-dione, 3-(6,11-dioxo-6,11-dihydro-1H-anthra-[1,2-d]-imidazol-2-ylthio)-N,N-diethylpropanamide, 2-(2-oxo-2-(pyrrolidin-1-yl)-ethylthio)-1H-anthra-[1,2-d]-imidazole-6,11-dione, 2-(3-oxo-3-(pyrrolidin-1-yl)-propylthio)-1H-anthra-[1,2-d]-imidazole-6,11-dione, 2-(6,11-dioxo-6,11-dihydro-1H-anthra-[1,2-d]-imidazol-2-ylthio)-N,N-dipropylacetamide, S-6,11-dioxo-6,11-dihydro-1H-anthra-[1,2-d]-imidazol-2-yl-2-nitrobenzothioate, S-6,11-dioxo-6,11-dihydro-1H-anthra-[1,2-d]-imidazol-2-yl-morpholine-4-carbothioate, S-6,11-dioxo-6,11-dihydro-1H-anthra-[1,2-d]-imidazol-2-yl-4-methylpiperazine-1-carbothioate, S-6,11-dioxo-6,11-dihydro-1H-anthra-[1,2-d]-imidazol-2-yl-3-phenylpropanethioate, S-6,11-dioxo-6,11-dihydro-1H-anthra-[1,2-d]-imidazol-2-yl-2,5-bis(trifluoromethyl)benzothioate, S-6,11-dioxo-6,11-dihydro-1H-anthra-[1,2-d]-imidazol-2-yl-2,5-dimethylfuran-3-carbothioate, S-6,11-dioxo-6,11-dihydro-1H-anthra-[1,2-d]-imidazol-2-yl-diethylcarbamothioate and 2-(2-n-ethylthio)-1H-anthra-[1,2-d]-imidazole-6,11-dione.

6. A compound as recited in claim 1, wherein said compound is selected from the group consisting of compounds 2-(ethylthio)-1H-anthra-[1,2-a]-imidazole-6,11-dione, 2-(propylthio)-1H-anthra-[1,2-d]-imidazole-6,11-dione, methyl-(6,11-dioxo-6,11-dihydro-1H-anthra-[1,2-d]-imidazol-2-ylthio)-butanoate, 2-(6-chlorohexylthio)-1H-anthra-[1,2-d]-imidazole-6,11-dione, 2-(allylthio)-1H-anthra-[1,2-a]-imidazole-6,11-dione, S-6,11-dioxo-6,11-dihydro-1H-anthra-[1,2-d]-imidazol-2-yl-2,5-bis(trifluoromethyl)benzothioate, and S-6,11-dioxo-6,11-dihydro-1H-anthra-[1,2-d]-imidazol-2-yl-diethylcarbamothioate.

7. A compound as recited in claim 1, wherein said compound is selected from the group consisting of compounds 2-mercapto-1(3)-H-anthra-[1,2-d]-imidazole-6,11-dione, 2-(ethylthio)-1H-anthra-[1,2-d]-imidazole-6,11-dione, 2-(propylthio)-1H-anthra-[1,2-d]-imidazole-6,11-dione, 2-(butylthio)-1H-anthra-[1,2-d]-imidazole-6,11-dione, methyl-(6,11-dioxo-6,11-dihydro-1H-anthra-[1,2-d]-imidazol-2-ylthio)-butanoate, (E)-methyl-4-(6,11-dioxo-6,11-dihydro-1H-anthra-[1,2-d]imidazol-2-ylthio)-but-2-enoate, 2-(prop-2-ynylthio)-1H-anthra-[1,2-d]-imidazole-6,11-dione, 2-(5-bromopentylthio)-1H-anthra-[1,2-d]-imidazole-6,11-dione, 2-(6-chlorohexylthio)-1H-anthra-[1,2-d]-imidazole-6,11-dione, 2-(2-piperidin-1-yl)-ethylthio)-1H-anthra-[1,2-d]-imidazole-6,11-dione, 2-(3-morpholino-3-oxopropylthio)-1H-anthra-[1,2-a]-imidazole-6,11-dione, 2-(allylthio)-1H-anthra-[1,2-d]-imidazole-6,11-dione, 2-(3-oxo-3-(pyrrolidin-1-yl)-propylthio)-1H-anthra-[1,2-d]-imidazole-6,11-dione, 2-(6,11-dioxo-6,11-dihydro-1H-anthra-[1,2-d]-imidazol-2-ylthio)-N,N-dipropylacetamide, S-6,11-dioxo-6,11-dihydro-1H-anthra-[1,2-d]-imidazol-2-yl-2-nitrobenzothioate, S-6,11-dioxo-6,11-dihydro-1H-anthra-[1,2-d]-imidazol-2-yl-morpholine-4-carbothioate, S-6,11-dioxo-6,11-dihydro-1H-anthra-[1,2-a]-imidazol-2-yl-2,5-bis(trifluoromethyl)benzothioate, S-6,11-dioxo-6,11-dihydro-1H-anthra-[1,2-a]-imidazol-2-yl-2,5-dimethylfuran-3-carbothioate, S-6,11-dioxo-6,11-dihydro-1H-anthra-[1,2-d]-imidazol-2-yl-piperidine-1-carbothioate, and S-6,11-dioxo-6,11-dihydro-1H-anthra-[1,2-d]-imidazol-2-yl-diethylcarbamothioate.

8. A compound as recited in claim 1, wherein said compound is selected from the group consisting of compounds 2-(3-morpholino-3-oxopropylthio)-1H-anthra-[1,2-d]-imidazole-6,11-dione, S-6,11-dioxo-6,11-dihydro-1H-anthra-[1,2-d]-imidazol-2-yl-2-nitrobenzothioate, and S-6,11-dioxo-6,11-dihydro-1H-anthra-[1,2-d]-imidazol-2-yl-2,5-dimethylfuran-3-carbothioate.

9. A compound as recited in claim 1, wherein said compound is selected from the group consisting of compounds 2-(butylthio)-1H-anthra-[1,2-d]-imidazole-6,11-dione, (E)-methyl-4-(6,11-dioxo-6,11-dihydro-1H-anthra-[1,2-d]imidazol-2-ylthio)-but-2-enoate, 2-(prop-2-ynylthio)-1H-anthra[1,2-d]-imidazole-6,11-dione, 2-(5-bromopentylthio)-1H-anthra-[1,2-d]-imidazole-6,11-dione, 2-(2-(piperidin-1-yl)-ethylthio)-1H-anthra-[1,2-d]-imidazole-6,11-dione, 2-(3-oxo-3-(pyrrolidin-1-yl)-propylthio)-1H-anthra-[1,2-d]-imidazole-6,11-dione, and 2-(6,11-dioxo-6,11-dihydro-1H-anthra[1,2-d]-imidazol-2-ylthio)-N,N-dipropylacetamide.

10. A compound as recited in claim 1, wherein said compound is 2-(5-bromopentylthio)-1H-anthra-[1,2-d]-imidazole-6,11-dione.

11. A compound as recited in claim 1, wherein said compound is selected from the group consisting of compounds S-6,11-dioxo-6,11-dihydro-1H-anthra-[1,2-d]-imidazol-2-yl-2-nitrobenzothioate and S-6,11-dioxo-6,11-dihydro-1H-anthra-[1,2-d]-imidazol-2-yl-2,5-dimethylfuran-3-carbothioate.

12. A compound as recited in claim 1, wherein said compound is selected from the group consisting of compounds 2-(ethylthio)-1H-anthra-[1,2-d]-imidazole-6,11-dione and 2-(3-(dimethylamino)propylthio)-1H-anthra-[1,2-d]-imidazole-6,11-dione.

13. A compound as recited in claim 1, wherein said compound comprises at least one compound selected from the group consisting of compounds 2-(2-(piperidin-1-yl)-ethylthio)-1H-anthra-[1,2-d]-imidazole-6,11-dione and 2-(3-(dimethylamino)propylthio)-1H-anthra-[1,2-d]-imidazole-6,11-dione.

14. A compound as recited in claim 1, wherein said compound is 2-(propylthio)-1H-anthra-[1,2-d]-imidazole-6,11-dione.

15. A compound as recited in claim 1, wherein said compound is selected from the group consisting of compounds 2-mercapto-1(3)-H-anthra-[1,2-d]-imidazole-6,11-dione, 2-(ethylthio)-1H-anthra-[1,2-d]-imidazole-6,11-dione, 2-(2-n-ethylthio)-1H-anthra-[1,2-d]-imidazole-6,11-dione, 2-(2-(piperidin-1-yl)-ethylthio)-1H-anthra-[1,2-d]-imidazole-6,11-dione and 2-(3-(dimethylamino)propylthio)-1H-anthra-[1,2-d]-imidazole-6,11-dione.

16. A method of administering an effective amount of the compound of claim 3 to inhibit telomerase.

17. A method of administering an effective amount of the compound of claim 4 to inhibit the growth of tumor cell GBM8401.

18. A method of administering an effective amount of the compound of claim 5 to inhibit the growth of tumor cell GBM8901.

19. A method of administering an effective amount of the compound of claim 6 to inhibit the growth of both tumor cells GBM 8401 and GBM8901.

20. A method of administering an effective amount of the compound of claim 8 to inhibit the growth of tumor cell GBM8401.

21. A method of administering an effective amount of the compound of claim 9 to inhibit the growth of tumor cell GBM 8901.

22. A method of treating renal cancer in a patient with an effective amount of the compound of claim 12.

23. A method of treating leukemia in a patient with an effective amount of the compound of claim 13.

* * * * *